(12) United States Patent
Muller et al.

(10) Patent No.: US 8,222,249 B2
(45) Date of Patent: Jul. 17, 2012

(54) ISOINDOLINE COMPOUNDS AND METHODS OF THEIR USE

(75) Inventors: George W. Muller, San Diego, CA (US); Alexander L. Ruchelman, Cream Ridge, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/359,369

(22) Filed: Jan. 26, 2012

(65) Prior Publication Data

US 2012/0122865 A1 May 17, 2012

Related U.S. Application Data

(63) Continuation of application No. 12/608,953, filed on Oct. 29, 2009, now Pat. No. 8,129,375.

(60) Provisional application No. 61/109,475, filed on Oct. 29, 2008.

(51) Int. Cl.
*A61K 31/5377* (2006.01)
*A61K 31/496* (2006.01)
*C07D 413/14* (2006.01)
*C07D 401/14* (2006.01)

(52) U.S. Cl. ............... 514/235.2; 514/253.09; 544/130; 544/364

(58) Field of Classification Search ............... 514/235.2, 514/318, 316, 253.09, 307, 266.22; 546/194, 546/187, 147; 544/130, 364, 287
See application file for complete search history.

(56) References Cited

U.S. PATENT DOCUMENTS

2009/0142297 A1* 6/2009 Muller et al. ................ 424/85.2
* cited by examiner

*Primary Examiner* — Kamal Saeed
*Assistant Examiner* — Kristin Bianchi
(74) *Attorney, Agent, or Firm* — Jones Day

(57) ABSTRACT

Provided herein are isoindoline compounds, pharmaceutical compositions comprising one or more of such compounds, and methods of their use for treating, preventing, or managing various diseases.

13 Claims, No Drawings

ND METHODS
ISOINDOLINE COMPOUNDS AND METHODS OF THEIR USE

This application is a continuation application of U.S. application Ser. No. 12/608,953, filed Oct. 29, 2009 now U.S. Pat. No. 8,129,375, which claims priority to U.S. Provisional Application No. 61/109,475, filed Oct. 29, 2008, the entireties of which are incorporated herein by reference.

1. FIELD

Provided herein are isoindoline compounds, pharmaceutical compositions comprising one or more of such compounds, and methods of their use for treating, preventing, or managing various diseases.

2. BACKGROUND

2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt et al., *Immunology* 17.1-17.12 (3rd ed., Mosby, St. Louis, Mo., 1993).

There are an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor ($\alpha,\beta$-FGF), angiogenin, vascular endothelial growth factor (VEGF), and TNF-$\alpha$. Alternatively, tumor cells can release angiogenic peptides through the production of proteases and the subsequent breakdown of the extracellular matrix where some cytokines are stored (e.g., $\beta$-FGF). Angiogenesis can also be induced indirectly through the recruitment of inflammatory cells (particularly macrophages) and their subsequent release of angiogenic cytokines (e.g., TNF-$\alpha$, $\beta$-FGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy, retinopathy of prematurity, corneal graft rejection, neovascular glaucoma, retrolental fibroplasia, arthritis, and proliferative vitreoretinopathy.

Accordingly, compounds that can control angiogenesis or inhibit the production of certain cytokines, including TNF-$\alpha$, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems, or allergic reactions.

With respect to chemotherapy, there is a variety of chemotherapeutic agents available for treatment of cancer. A majority of cancer chemotherapeutics act by inhibiting DNA synthesis, either directly or indirectly by inhibiting the biosynthesis of deoxyribonucleotide triphosphate precursors, to prevent DNA replication and concomitant cell division, Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., Chapter. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat. However, some compounds such as protamine, heparin and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for effective methods of treating, preventing, and managing cancer and other diseases and conditions, particularly for diseases that are refractory to standard treatments, such as surgery, radiation therapy, chemotherapy and hormonal therapy, while reducing or avoiding the toxicities and/or side effects associated with the conventional therapies.

3. SUMMARY

Provided herein are isoindoline compounds, and pharmaceutically acceptable salts, solvates, prodrugs, or stereoisomers thereof.

Also provided herein are pharmaceutical compositions comprising a compound provided herein, e.g., a compound of Formula I, including a single enantiomer, a mixture of enantiomers, or a mixture of diastereomers thereof; or a pharmaceutically acceptable salt, solvate, or prodrug thereof; in combination with one or more pharmaceutically acceptable carriers.

Further provided herein are methods of treating, preventing, or managing various diseases in a subject, which comprise administering to the subject a therapeutically effective amount of a compound provided herein, e.g., a compound of Formula I, including a single enantiomer, a mixture of enantiomers, or a mixture of diastereomers thereof, or a pharmaceutically acceptable salt, solvate, or prodrug thereof.

4. DETAILED DESCRIPTION

4.1 Definitions

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" refer to the eradication or amelioration of a disease or disorder, or of one or more symptoms associated with the disease or disorder. In general, treatment occurs after the onset of the disease or disorder. In certain embodiments, the terms refer to minimizing the spread or worsening of the disease or disorder resulting from the administration of one or more prophylactic or therapeutic agents to a subject with such a disease or disorder.

The terms "prevent," "preventing," and "prevention" refer to the prevention of the onset, recurrence or spread of a disease or disorder, or of one or more symptoms thereof. In general, prevention occurs prior to the onset of the disease or disorder.

The terms "manage," "managing," and "management" refer to preventing or slowing the progression, spread or worsening of a disease or disorder, or of one or more symptoms thereof. Sometimes, the beneficial effects that a subject derives from a prophylactic or therapeutic agent do not result in a cure of the disease or disorder.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "$IC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* Gibson Ed., CRC Press LLC: Boca Raton, Fla., 2004.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "alkyl" refers to a linear or branched saturated monovalent hydrocarbon radical, wherein the alkyl may optionally be substituted with one or more substituents. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkenyl" refers to a linear or branched monovalent hydrocarbon radical, which contains one or more, in one embodiment, one to five, carbon-carbon double bonds. The alkenyl may be optionally substituted one or more substituents. The term "alkenyl" also embraces radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, carbon-carbon triple bonds. The alkynyl may be optionally substituted one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents.

The term "aralkyl" or "aryl-alkyl" refers to a monovalent alkyl group substituted with aryl. In certain embodiments, both alkyl and aryl may be optionally substituted with one or more substituents.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, heteroaryl may also be optionally substituted with one or more substituents.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may includes a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, heterocyclic may also be optionally substituted with one or more substituents.

The term "halogen", "halide" or "halo" refers to fluorine, chlorine, bromine, and/or iodine.

The terms "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

4.2 Compounds

Provided herein are isoindoline compounds, pharmaceutical compositions comprising one or more of such compounds, and methods of their use for treating, preventing, or managing various diseases.

In one embodiment, provided is a compound of Formula I:

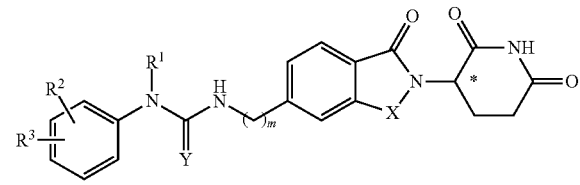

(1)

or a pharmaceutically acceptable salt, solvate, prodrug, or stereoisomer thereof, wherein:

X is C(=O) or $CH_2$;
Y is O, cyanamide (N==N), or amido (NH);
m is an integer of 0, 1, 2, or 3;
$R^1$ is hydrogen or $C_{1-6}$ alkyl;
$R^2$ is hydrogen, $-NO_2$, $C_{1-10}$ alkyl, $C_{0-6}$ alkyl-(5 to 10 membered heteroaryl), $C_{0-6}$ alkyl-(5 to 6 membered heterocyclyl), $C_{0-6}$ alkyl-OH, $C_{0-4}$ alkyl-$NH_2$, $-NHCO-$ $C_{1-6}$ alkyl, $-OR^{21}$, or $-(CH_2-Z)_{0-2}$-(5 to 10 membered heteroaryl), where each heteroaryl and heterocyclyl is optionally substituted with one or more $C_{1-6}$ alkyl;
$R^3$ is hydrogen, halogen, $-NO_2$, $C_{0-6}$ alkyl-(5 to 10 membered heteroaryl), $C_{0-6}$ alkyl-(5 to 6 membered heterocyclyl), $C_{0-6}$ alkyl-OH, $C_{0-4}$ alkyl-$NH_2$, $-NHCO-C_{1-6}$ alkyl, $-OR^{21}$, or $-(CH_2-Z)_{0-2}$-(5 to 10 membered heteroaryl), where each heteroaryl and heterocyclyl is optionally substituted with one or more $C_{1-6}$ alkyl;
$R^{21}$ is $C_{6-10}$ aryl, 5 to 10 membered heteroaryl, 5 to 6 membered heterocyclyl, or $-CO(CH_2)_{0-2}R^{22}$, wherein the aryl, heteroaryl, and heterocyclyl are each optionally substituted with one or more $C_{1-6}$ alkyl;
$R^{22}$ is $-NH_2$ or 5 to 6 membered heterocyclyl; and
Z is $CH_2$, NH, or O;
with the proviso that when $R^1$ is hydrogen, then $R^2$ is not hydrogen or $C_{1-10}$ alkyl;
with the proviso that when Y is O, then $R^3$ is not halogen; and
with the proviso that when Y is O and $R^3$ is halogen, then $R^2$ is $C_{0-6}$ alkyl-(5-6 membered heterocyclyl).

In certain embodiments, X is $CH_2$. In certain embodiments, X is C(=O).

In certain embodiments, Y is O. In certain embodiments, Y is cyanamido. In certain embodiments, Y is amido.

In certain embodiments, Z is $CH_2$. In certain embodiments, Z is NH. In certain embodiments, Z is O.

In certain embodiments, m is 0. In certain embodiments, m is 1. In certain embodiments, m is 2. In certain embodiments, m is 3.

In certain embodiments, $R^1$ is hydrogen. In certain embodiments, $R^1$ is $C_{1-6}$ alkyl, optionally substituted with one, two, or three substituents Q as described herein. In certain embodiments, $R^1$ is methyl.

In certain embodiments, $R^2$ is hydrogen. In certain embodiments, $R^2$ is halogen. In certain embodiments, $R^2$ is nitro. In certain embodiments, $R^2$ is $C_{1-10}$ alkyl. In certain embodiments, $R^2$ is $C_{0-6}$ alkyl-(5 to 10 membered heteroaryl), where the heteroaryl is optionally substituted with one or more $C_{1-6}$ alkyl. In certain embodiments, $R^2$ is $C_{0-6}$ alkyl-(5 to 6 membered heterocyclyl), where the heterocyclyl is optionally substituted with one or more $C_{1-6}$ alkyl. In certain embodiments, $R^2$ is $C_{0-6}$ alkyl-OH. In certain embodiments, $R^2$ is $C_{0-4}$ alkyl-$NH_2$. In certain embodiments, $R^2$ is $-NHCO-C_{1-6}$ alkyl. In certain embodiments, $R^2$ is $-OR^{21}$, wherein $R^{21}$ is as described herein. In certain embodiments, $R^2$ is or $-(CH_2-Y)_{0-2}$-(5 to 10 membered heteroaryl), where the heteroaryl is optionally substituted with one or more $C_{1-6}$ alkyl. In certain embodiments, $R^2$ is hydrogen, amino, acetamido, hydroxy, nitro, aminomethyl, hydroxymethyl, 2-methyl-1H-imidazol-1-yl, 3-methyl-1,2,4-oxadiazol-5-yl, 4-methylpiperazin-1-yl)methyl, 2-methyl-2H-pyrazol-3-yl, 1-methyl-1H-pyrazol-3-yl, 2-methylthiazol-4-yl, 4-methyl-4H-1,2,4-triazol-3-yl, morpholinomethyl, (pyridin-4-yl)methyl, (pyridin-4-yloxy)methyl, pheoxy, pyridin-2-yloxy, piperidin-4-yloxy, 2-aminoacetoxy, or 2-piperazin-1-ylacetoxy.

In certain embodiments, $R^3$ is hydrogen. In certain embodiments, $R^3$ is nitro. In certain embodiments, $R^3$ is $C_{0-6}$ alkyl-(5 to 10 membered heteroaryl), where the heteroaryl is optionally substituted with one or more $C_{1-6}$ alkyl. In certain embodiments, $R^3$ is $C_{0-6}$ alkyl-(5 to 6 membered heterocyclyl), where the heterocyclyl is optionally substituted with one or more $C_{1-6}$ alkyl. In certain embodiments, $R^3$ is $C_{0-6}$ alkyl-OH. In certain embodiments, $R^3$ is $C_{0-4}$ alkyl-$NH_2$. In certain embodiments, $R^3$ is $-NHCO-C_{1-6}$ alkyl. In certain embodiments, $R^3$ is $-OR^{21}$, wherein $R^{21}$ is as described herein. In certain embodiments, $R^3$ is or $-(CH_2-Y)_{0-2}$-(5 to 10 membered heteroaryl), where the heteroaryl is optionally substituted with one or more $C_{1-6}$ alkyl. In certain embodiments, $R^3$ is hydrogen, amino, acetamido, hydroxy, nitro, methyl, aminomethyl, hydroxymethyl, 2-methyl-1H-imidazol-1-yl, 3-methyl-1,2,4-oxadiazol-5-yl, 4-methylpiperazin-1-yl)methyl, 2-methyl-2H-pyrazol-3-yl, 1-methyl-1H-pyrazol-3-yl, 2-methylthiazol-4-yl, 4-methyl-4H-1,2,4-triazol-3-yl, morpholinomethyl, (pyridin-4-yl)methyl, (pyridin-4-yloxy)methyl, pheoxy, pyridin-2-yloxy, piperidin-4-yloxy, 2-aminoacetoxy, or 2-piperazin-1-ylacetoxy.

In one embodiment, the compound is:

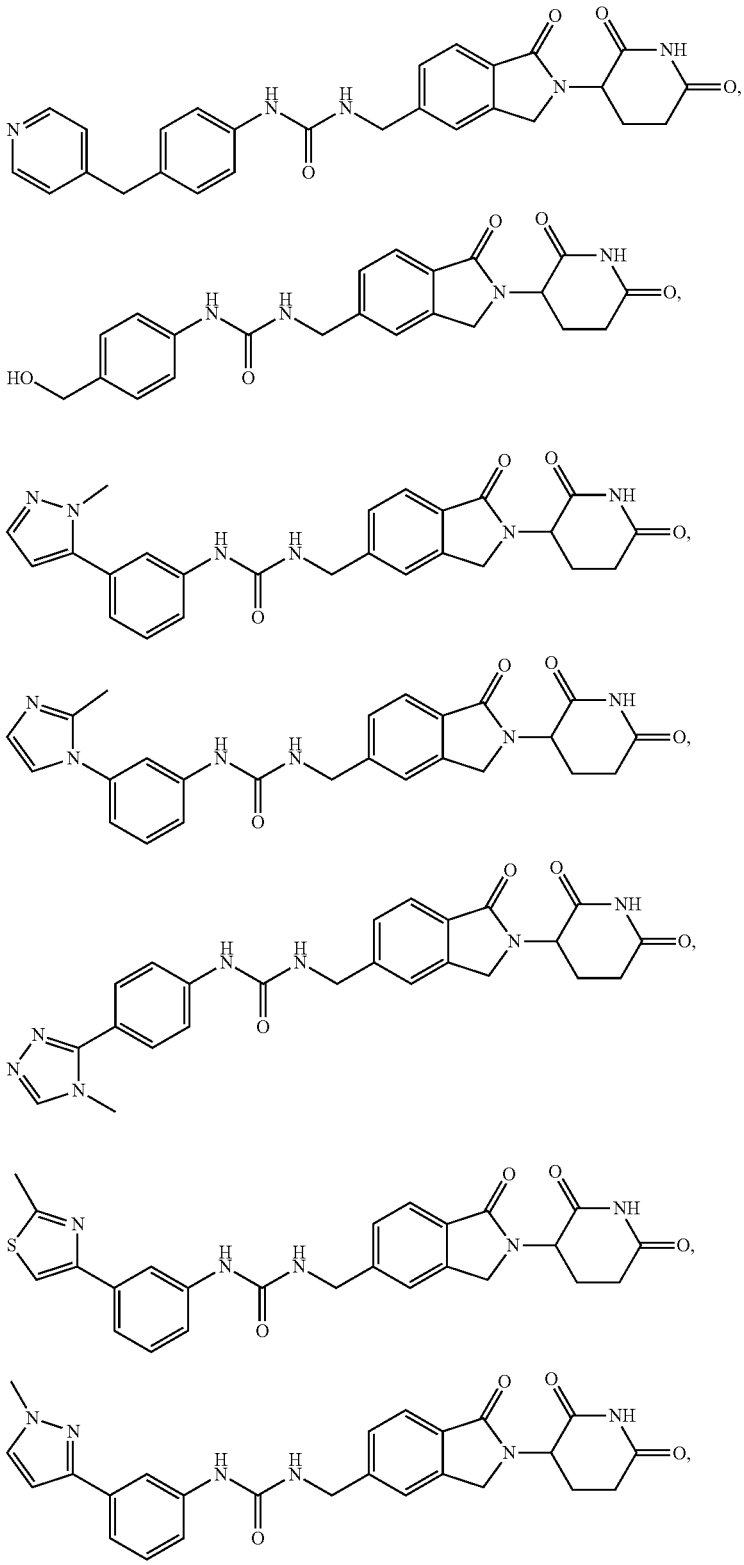

-continued
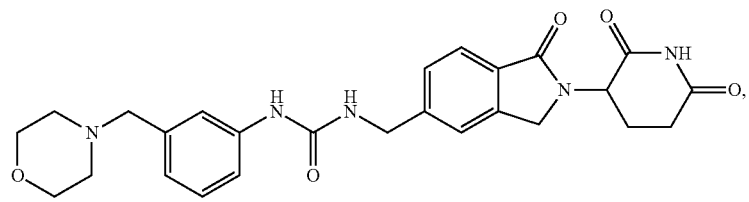
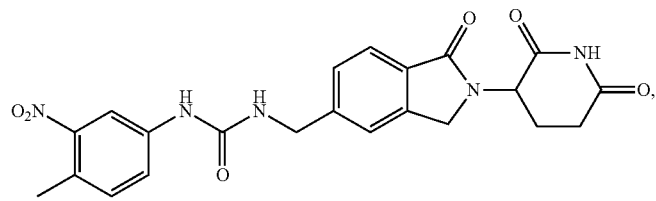
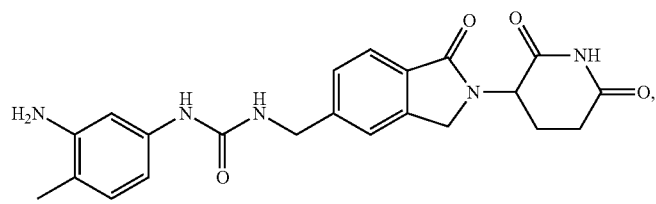
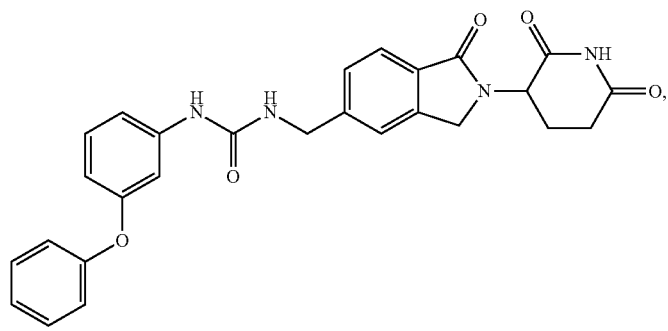
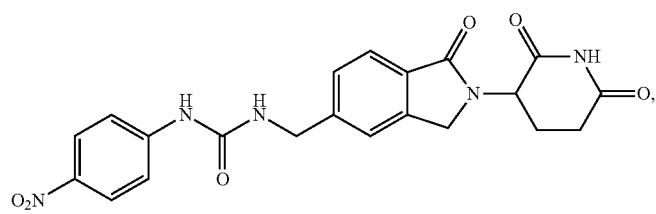
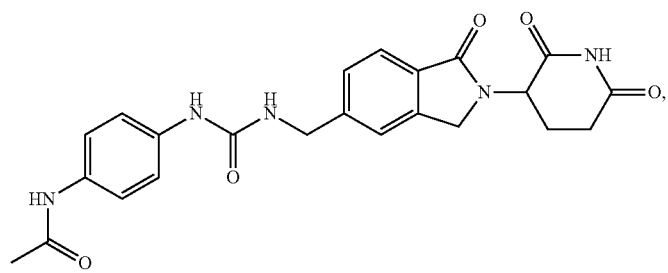
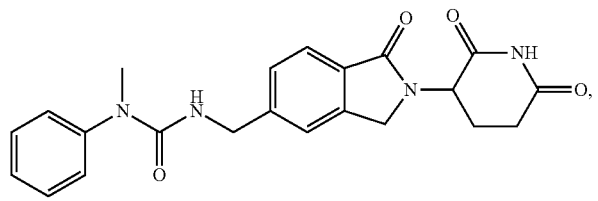

-continued
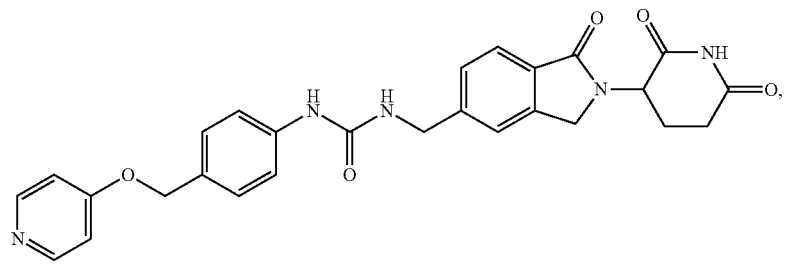
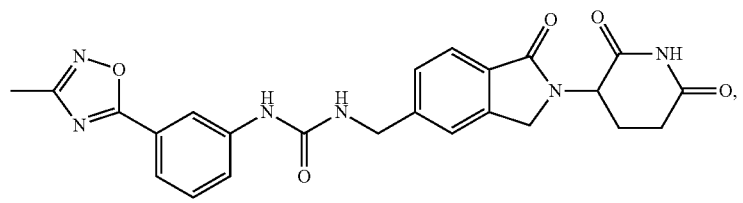
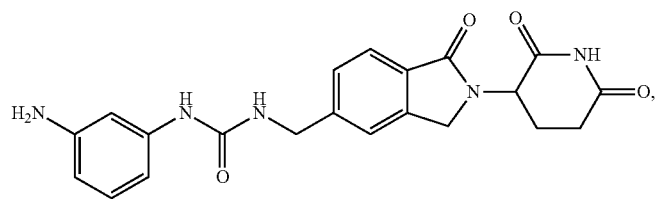
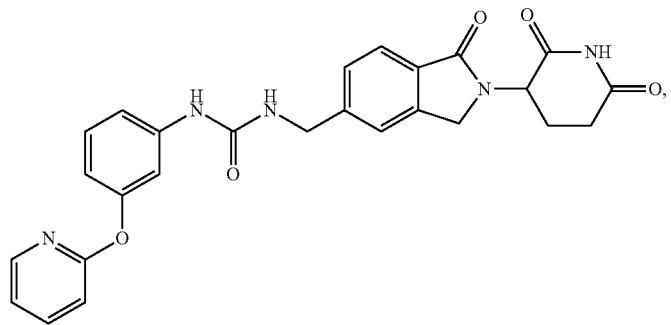
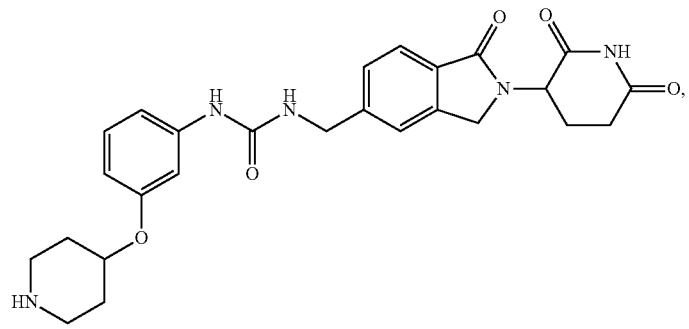
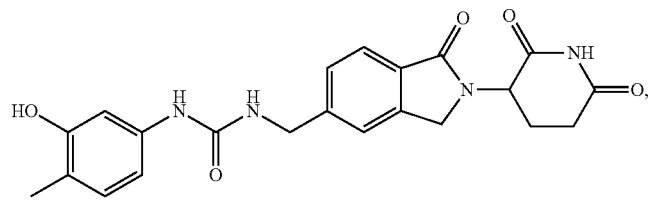
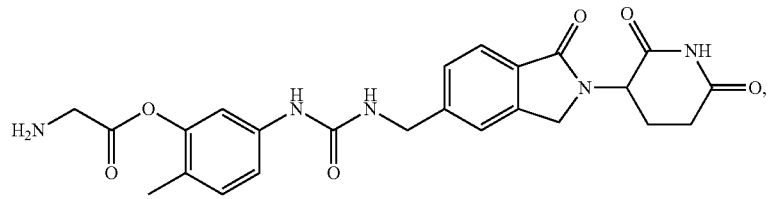

-continued
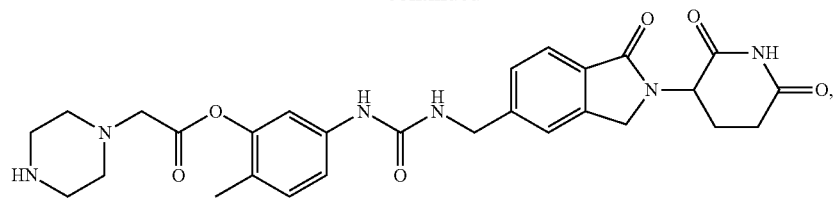
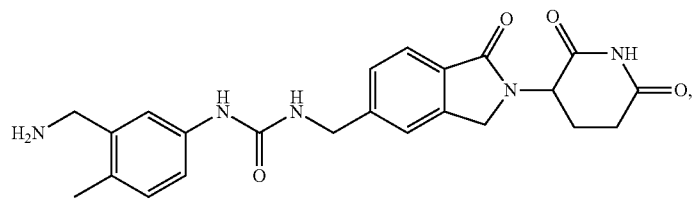
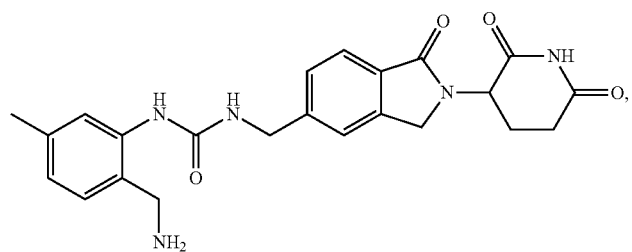
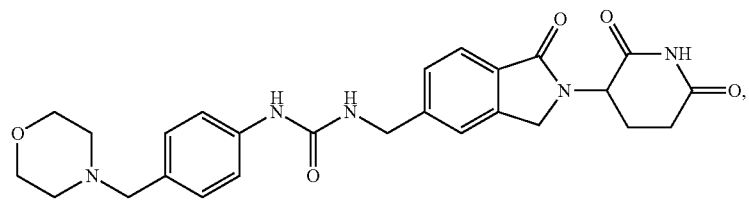
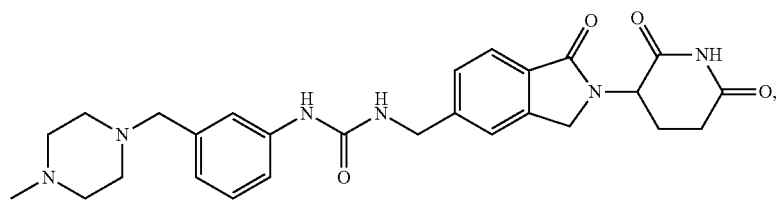
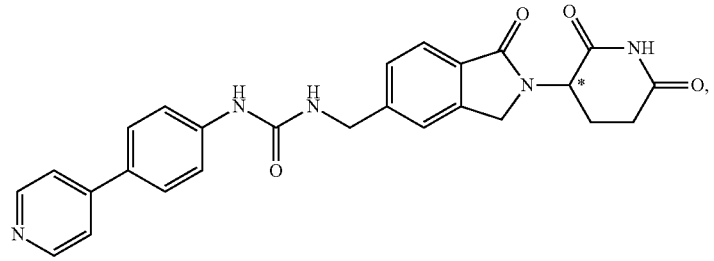
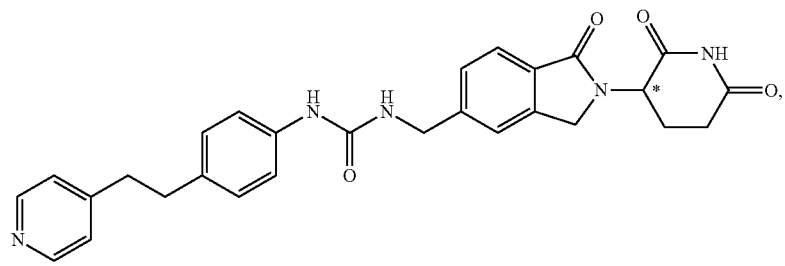

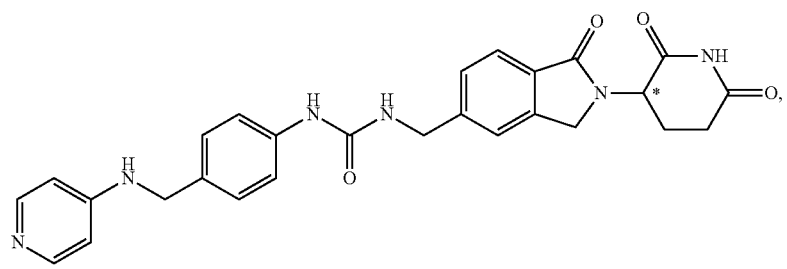
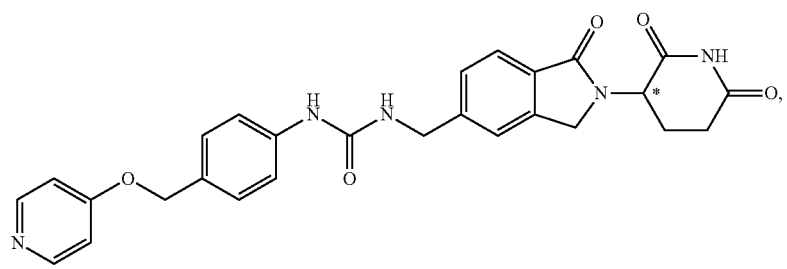
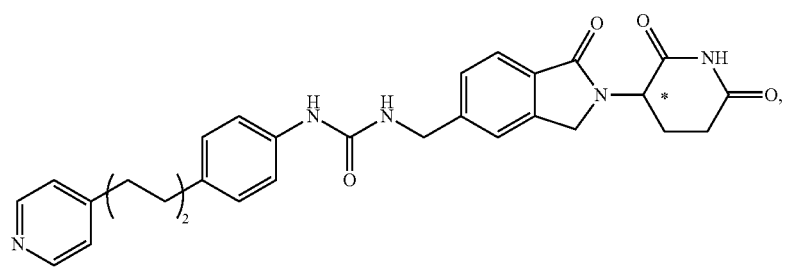
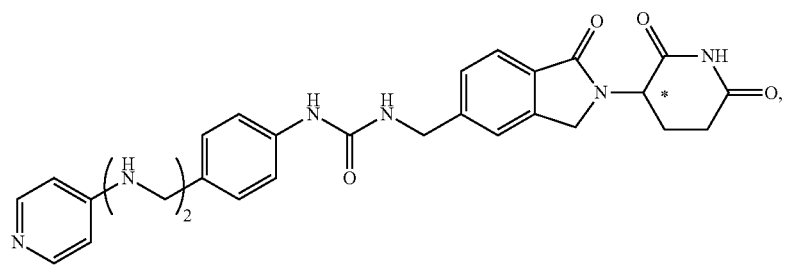
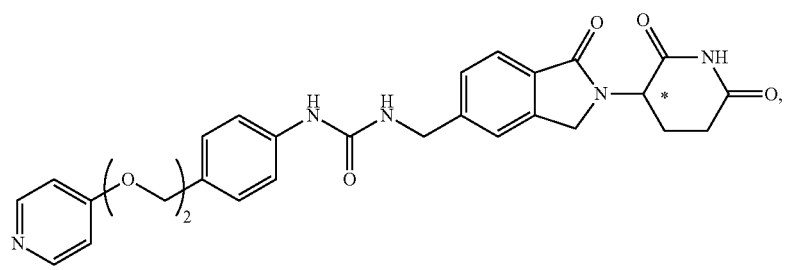
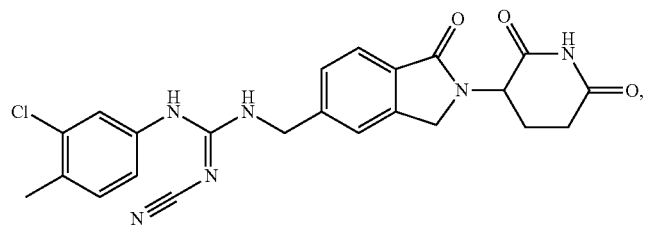

-continued

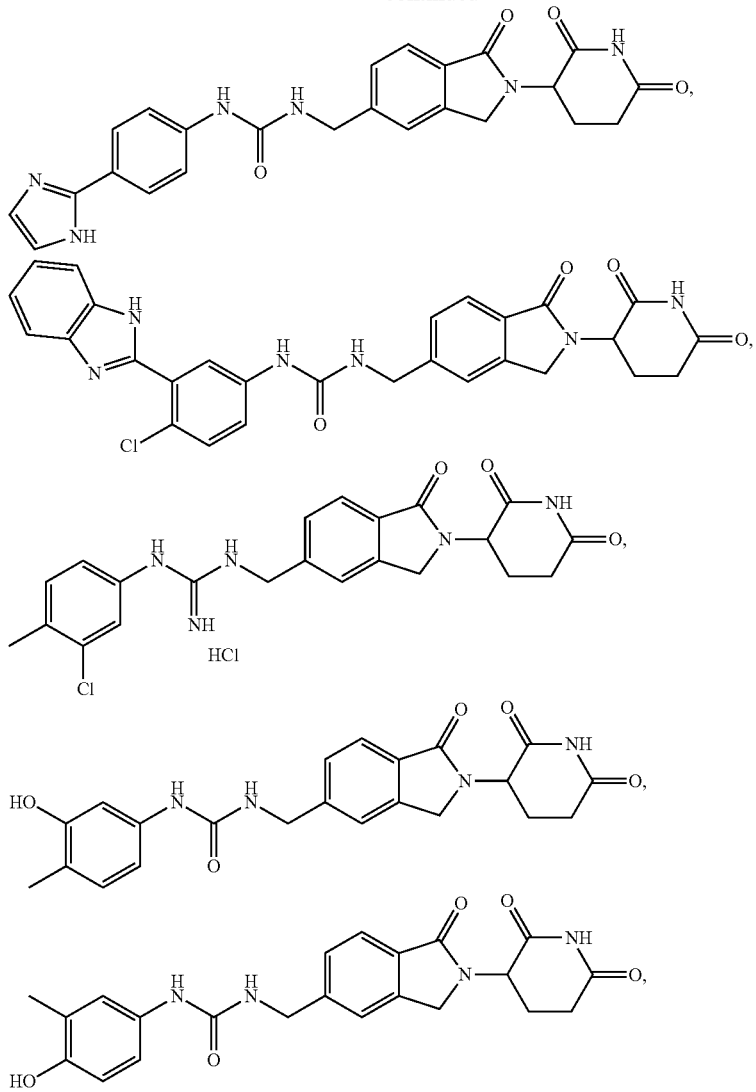

or a pharmaceutically acceptable salt, solvate, prodrug, and stereoisomer thereof.

In another embodiment, provided herein is a compound of Formula II:

(II)

or a pharmaceutically acceptable salt, solvate, prodrug, or stereoisomer thereof, wherein:

X is C(=O) or CH$_2$;
m is an integer of 0, 1, 2, or 3;
R$^4$ is C$_{3-10}$ cycloalkyl, 5 to 10 membered heterocyclyl, 5 to 10 membered heteroaryl, or C$_{0-4}$ alkyl-NR$^{41}$R$^{42}$; wherein the cycloalkyl, heterocyclyl, and heteroaryl are each optionally substituted with one or more halogen, C$_{1-6}$ alkyl, —CO—NR$^{43}$R$^{44}$, —COOR$^{45}$, or C$_{0-4}$ alkyl-C$_{6-10}$ aryl, wherein the aryl itself may be optionally substituted with one or more halogen; and
R$^{41}$, R$^{42}$, R$^{43}$, R$^{44}$, and R$^{45}$ are each independently hydrogen or C$_{1-6}$ alkyl.

In certain embodiments, X is CH$_2$. In certain embodiments, X is C(=O).

In certain embodiments, m is 0. In certain embodiments, m is 1. In certain embodiments, m is 2. In certain embodiments, m is 3.

In certain embodiments, R$^4$ is C$_{3-10}$ cycloalkyl, optionally substituted with one or more (C$_{1-6}$) alkyl or C$_{0-4}$ alkyl-C$_{6-10}$ aryl. In certain embodiments, R$^4$ is 5 to 6 membered heterocyclyl, optionally substituted with one or more (C$_{1-6}$) alkyl or C$_{0-4}$ alkyl-C$_{6-10}$ aryl. In certain embodiments, R$^4$ is C$_{0-4}$ alkyl-NR$^{41}$R$^{42}$, wherein R$^{41}$ and R$^{42}$ are each described herein.

In certain embodiments, R$^4$ is 3-(N,N-diethylamino)propyl, 4-acetamidophenyl, 3-(2-aminoacetoxy)-4-methylphenyl, 3-aminomethyl-4-methylphenyl, 2-aminomethyl-5-methylphenyl, 3-aminophenyl, 3-amino-4-methylphenyl, 3-chloro-4-methylphenyl, 4-hydroxymethylphenyl, 3-hydroxy-4-methylphenyl, 3-(2-methyl-1H-imidazol-1-yl)phenyl, 4-methyl-3-nitrophenyl, 3-(3-methyl-1,2,4-oxadiazol-5-yl)phenyl, 4-methyl-3-(2-piperazin-1ylacetoxy)-phenyl, 3-((4-methylpiperazin-1-yl)methyl)phenyl, 3-(1-methyl-1H-pyrazol-3-yl)phenyl, 3-(2-methyl-2H-pyrazol-3-yl)phenyl, 3-(2-methylthiazol-4-yl)phenyl, 4-(4-methyl-4H-1,2,4-triazol-3-yl)phenyl, 3-(morpholinomethyl)phenyl, 4-(morpholinomethyl)phenyl, 4-nitrophenyl, phenyl, 3-(piperidin-4-yloxy)phenyl, 4-(pyridin-4-yl)methylphenyl, 4-((pyridin-4-yloxy)methyl)phenyl, 3-(pyridin-2-yloxy)phenyl, 3-phenoxyphenyl, 4-tert-butylcyclohexyl, cis-4-tert-butylcyclohexyl, trans-4-tert-butylcyclohexyl, 4-methylcyclohexyl, cis-4-methylcyclohexyl, trans-4-methylcyclohexyl, 1-benzylpiperidin-4-yl, 4-methyltetrahydro-2H-pyran-4-yl, piperidin-4-yl, 4-phenylcyclohexyl, cis-4-phenylcyclohexyl, or trans-4-phenylcyclohexyl.

In one embodiment, the compound is:

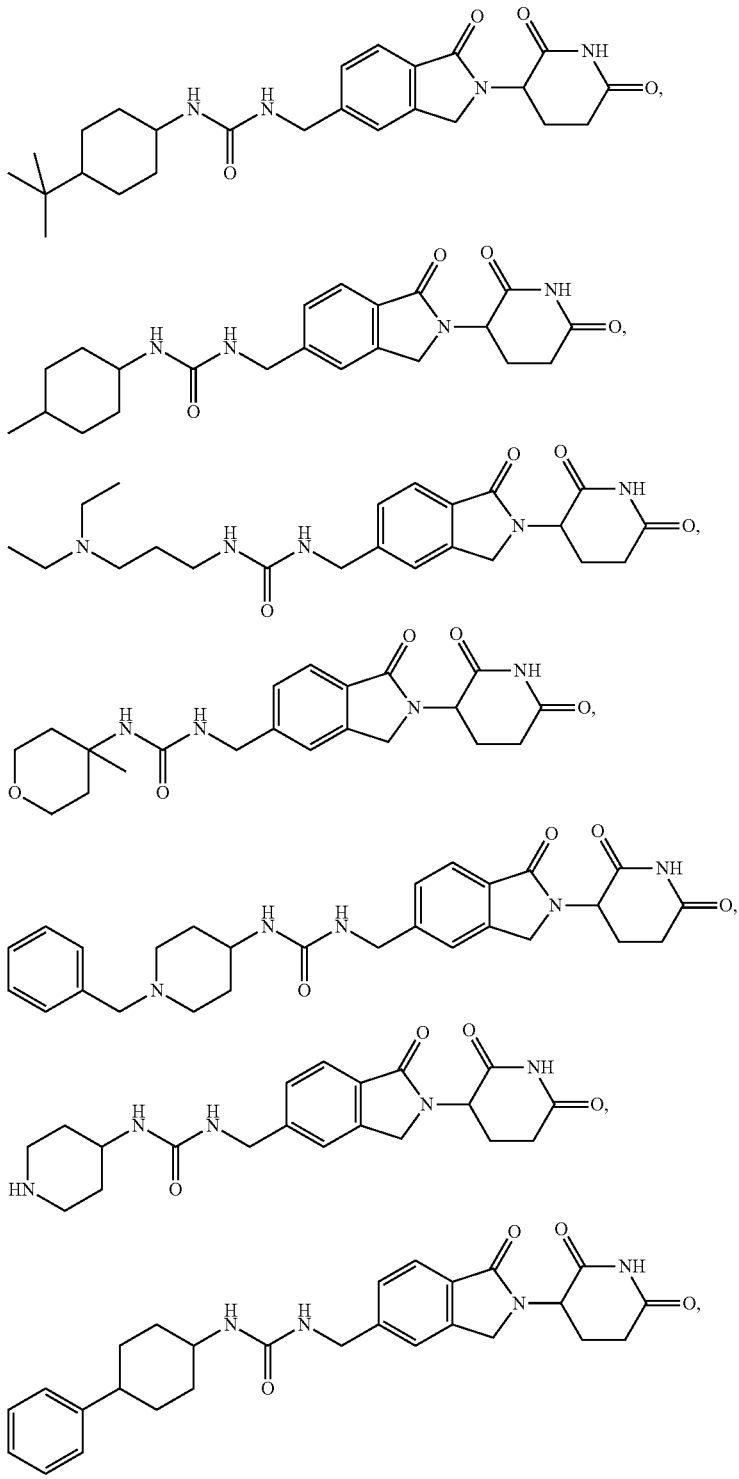

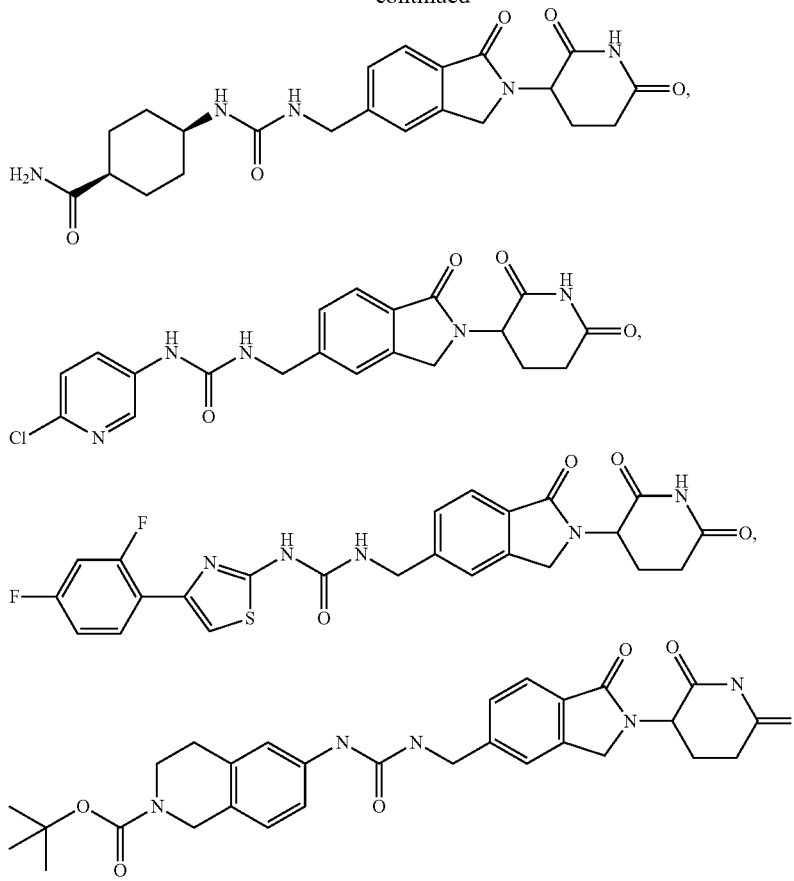

or a pharmaceutically acceptable salt, solvate, prodrug, or stereoisomer thereof.

In yet another embodiment, provided herein is a compound of Formula III:

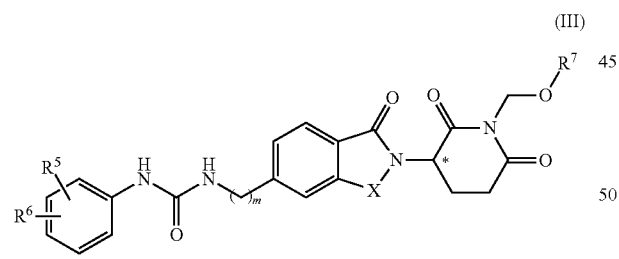

or a pharmaceutically acceptable salt, solvate, prodrug, or stereoisomer thereof, wherein:

X is C(=O) or CH$_2$;

m is an integer of 0, 1, 2, or 3;

R$^5$ and R$^6$ are each independently: hydrogen, halo, C$_{1-6}$ alkyl, oxo, —NO$_2$, C$_{1-6}$ alkoxy, —Z-C$_{1-6}$ alkyl, C$_{0-6}$ alkyl-(5 to 10 membered heteroaryl), C$_{0-6}$ alkyl-(5 to 6 membered heterocyclyl), C$_{0-6}$ alkyl-OH, C$_{0-4}$ alkyl-NH$_2$, —NHCO-C$_{1-6}$ alkyl, —OR$^{21}$, or —(CH$_2$—Y)$_{0-2}$-(5 to 10 membered heteroaryl), wherein Z is S or SO$_2$;

wherein R$^{21}$ is as defined above;

wherein each heteroaryl and heterocyclyl above is optionally substituted with one or more C$_{1-6}$ alkyl; and wherein the alkyl or alkoxy above may be optionally substituted with one or more: halogen; cyano; nitro; amino; C$_{1-6}$ alkylidenedioxy; C$_{1-6}$ alkoxy, itself optionally substituted with one or more halogens; or C$_{1-6}$ alkylthio, itself optionally substituted with one or more halogens;

R$^7$ is —COR$^{71}$ or —PO(OR$^{72}$)(OR$^{73}$);

R$^{71}$ is C$_{1-10}$ alkyl, C$_{6-10}$ aryl, or 5 to 6 membered heterocyclyl; wherein the alkyl, aryl, heterocyclyl may be optionally substituted with one or more amino, C$_{1-6}$ alkylamino, di(C$_{1-6}$ alkyl)amino, or —COOR$^{74}$; and R$^{72}$, R$^{73}$, and R$^{74}$ are ach independently hydrogen or C$_{1-10}$ alkyl.

In certain embodiments, X is CH$_2$. In certain embodiments, X is C(=O).

In certain embodiments, m is 0. In certain embodiments, m is 1. In certain embodiments, m is 2. In certain embodiments, m is 3.

In certain embodiments, R$^5$ is hydrogen. In certain embodiments, R$^5$ is halo. In certain embodiments, R$^5$ is fluoro or chloro.

In certain embodiments, R$^6$ is hydrogen. In certain embodiments, R$^6$ is halo. In certain embodiments, R$^6$ is fluoro or chloro.

In certain embodiments, R$^7$ is —COR$^{41}$, wherein R$^{41}$ is as described herein. In certain embodiments, R$^7$ is —PO(OR$^{42}$))(OR$^{43}$), wherein R$^{42}$ and R$^{43}$ are each as described herein.

In one embodiment, the compound is:
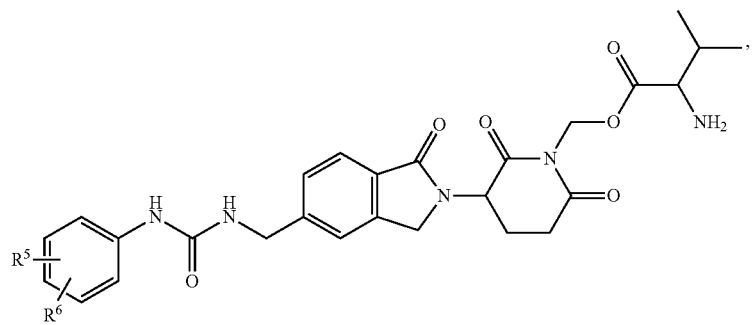
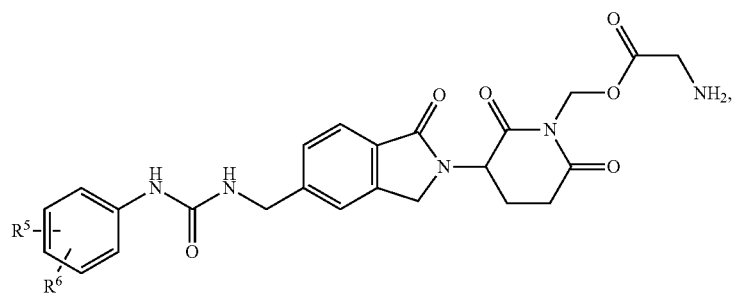
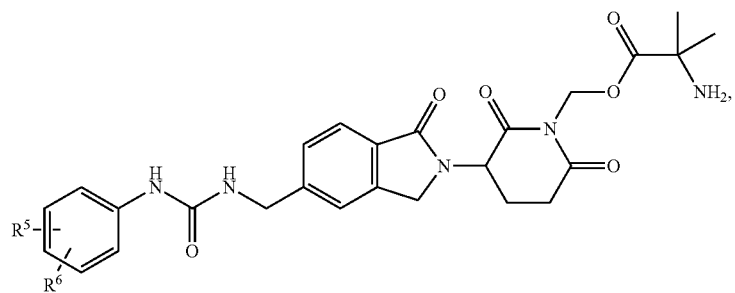
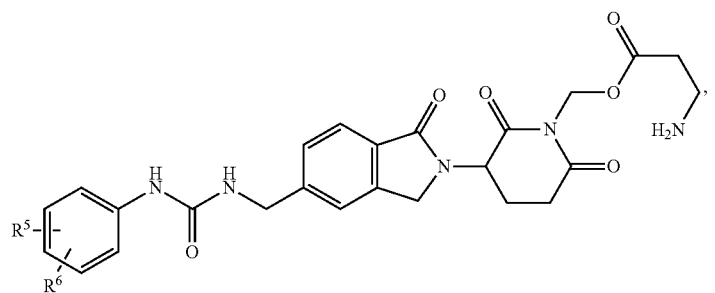
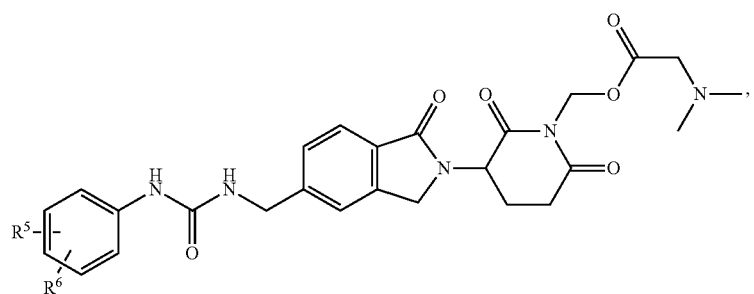

-continued
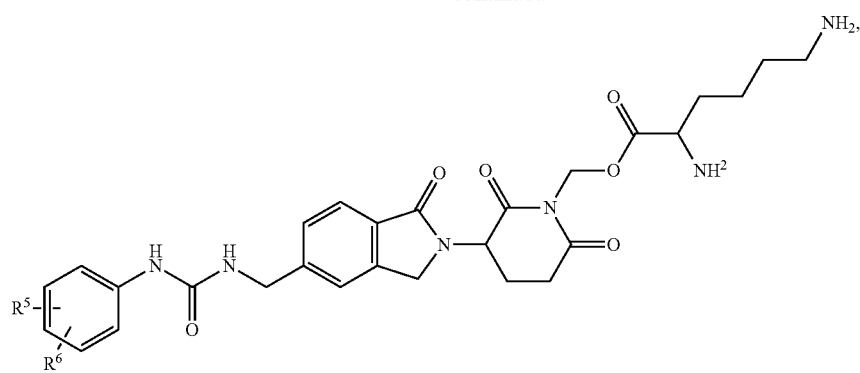
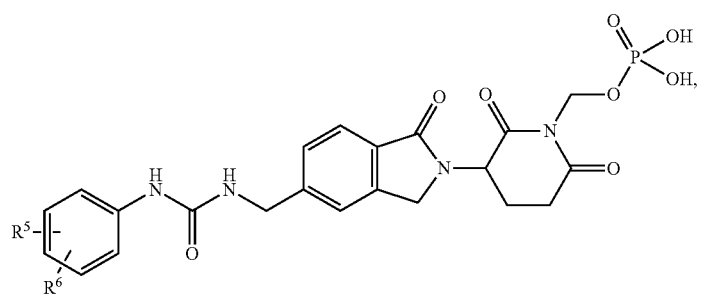
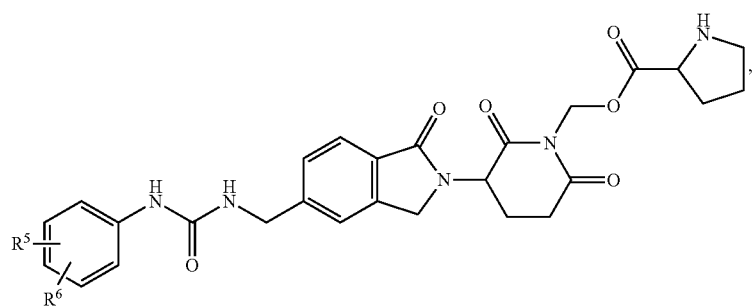
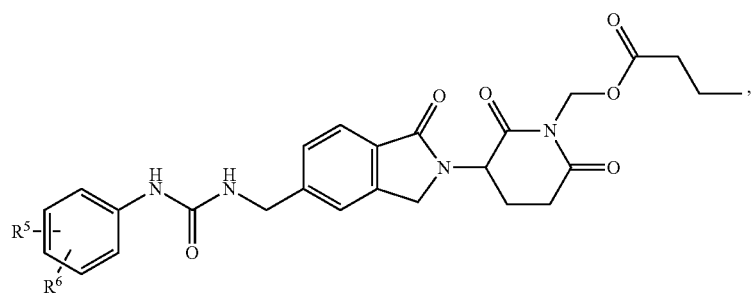
9
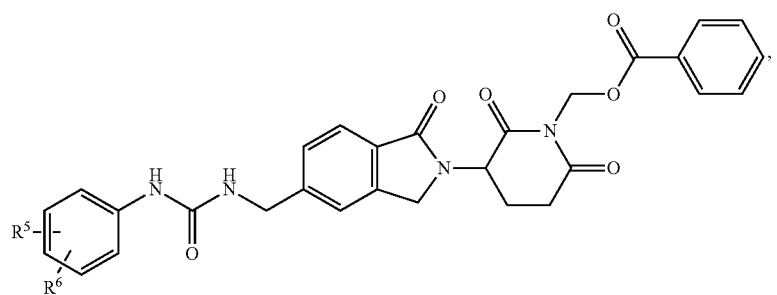
10

-continued

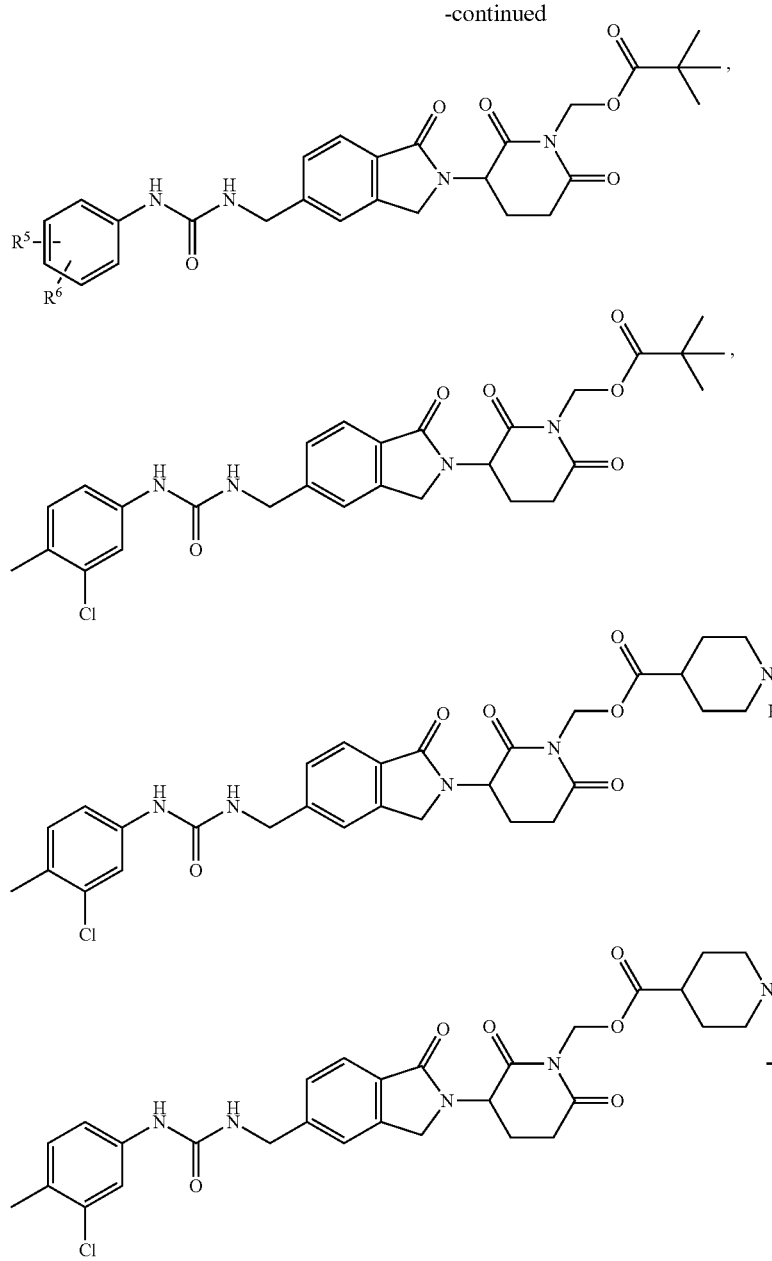

or a pharmaceutically acceptable salt, solvate, prodrug, or stereoisomer thereof, wherein $R^5$ and $R^6$ are as defined above.

In yet another embodiment, provided herein is a compound of Formula IV:

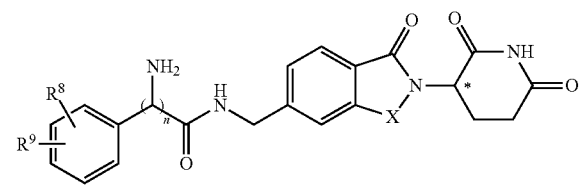

(IV)

or a pharmaceutically acceptable salt, solvate, prodrug, or stereoisomer thereof, wherein:

X is C(═O) or $CH_2$;

n is an integer of 0 or 1;

$R^8$ is hydrogen or halo; and $R^9$ is hydrogen, amino, or 5 to 10 membered heteroaryl or heterocyclyl;

with the proviso that when m is 0, $R^9$ is not hydrogen.

In certain embodiments, X is $CH_2$. In certain embodiments, X is C(═O).

In certain embodiments, n is 0. In certain embodiments, n is 1.

In certain embodiments, $R^8$ is hydrogen. In certain embodiments, $R^8$ is halo. In certain embodiments, $R^8$ is fluoro or chloro.

In certain embodiments, $R^9$ is hydrogen. In certain embodiments, $R^9$ is amino. In certain embodiments, $R^9$ is 5 to 10 membered heteroaryl. In certain embodiments, $R^9$ is 5 to 10 membered heterocyclyl.

In one embodiment, the compound is:

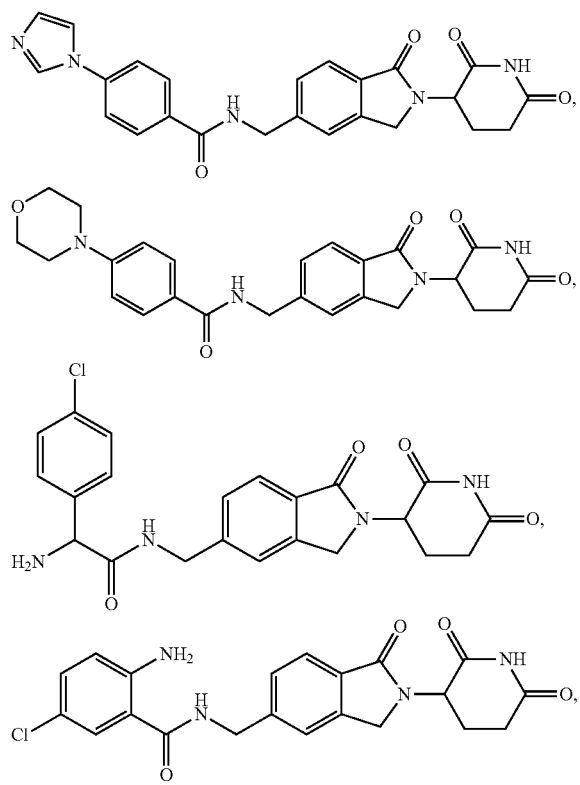

or a pharmaceutically acceptable salt, solvate, prodrug, or stereoisomer thereof.

In yet another embodiment, provided herein is a compound of Formula V:

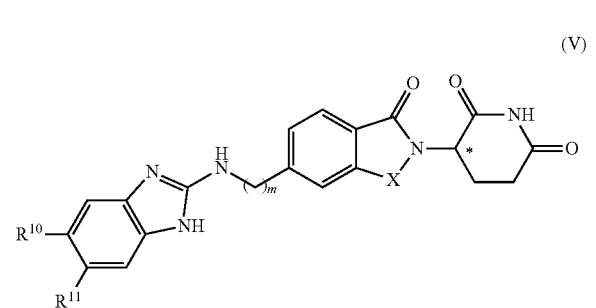

or a pharmaceutically acceptable salt, solvate, prodrug, or stereoisomer thereof, wherein:

X is C(=O) or $CH_2$;
m is an integer of 0, 1, 2, or 3;
$R^{10}$ and $R^{11}$ are each independently hydrogen, halo, $C_{1-6}$ alkyl, or $C_{6-10}$ aryloxy, wherein the alkyl and aryl are each optionally substituted with one or more halo.

In certain embodiments, X is $CH_2$. In certain embodiments, X is C(=O).

In certain embodiments, m is 0. In certain embodiments, m is 1. In certain embodiments, m is 2. In certain embodiments, m is 3.

In certain embodiments, $R^{10}$ is hydrogen. In certain embodiments, $R^{10}$ is halo. In certain embodiments, $R^{10}$ is fluoro or chloro. In certain embodiments, $R^{10}$ is $C_{1-6}$ alkyl, optionally substituted with one or more halo. In certain embodiments, $R^{10}$ is $C_{6-10}$ aryloxy, optionally substituted with one or more halo.

In certain embodiments, $R^{11}$ is hydrogen. In certain embodiments, $R^{11}$ is halo. In certain embodiments, $R^{11}$ is fluoro or chloro. In certain embodiments, $R^{11}$ is $C_{1-6}$ alkyl, optionally substituted with one or more halo. In certain embodiments, $R^{11}$ is $C_{6-10}$ aryloxy, optionally substituted with one or more halo.

In one embodiment, the compound is:

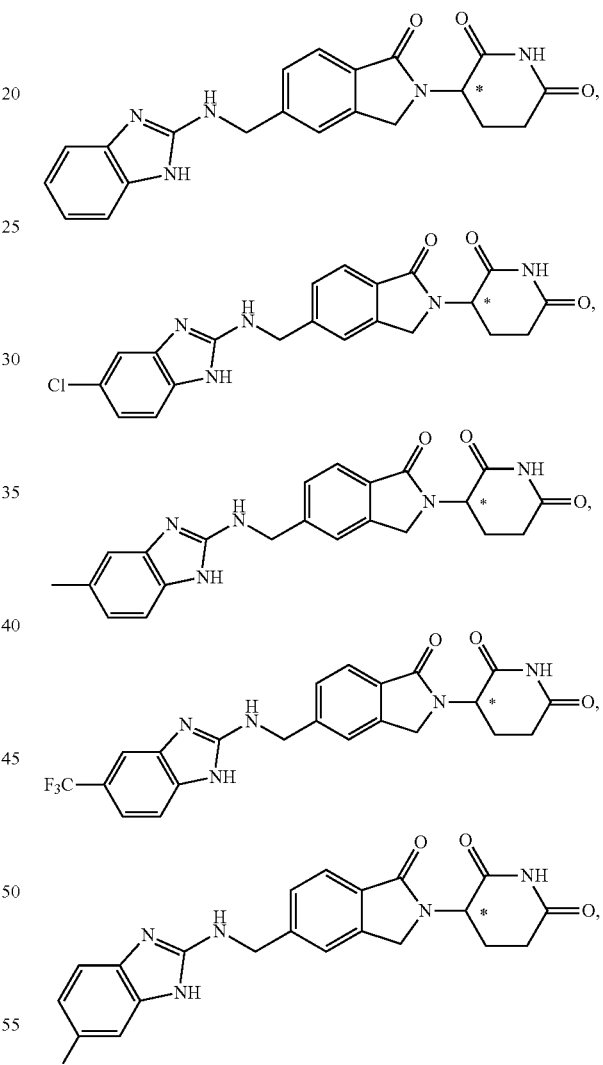

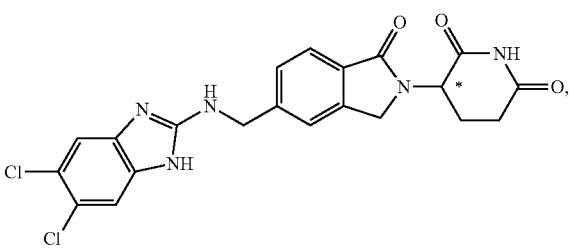

33
-continued
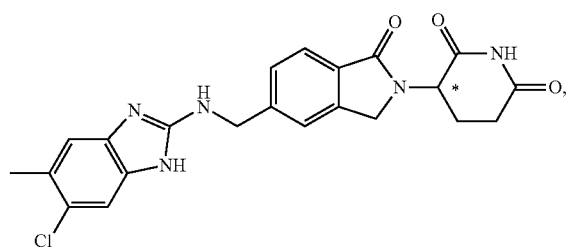
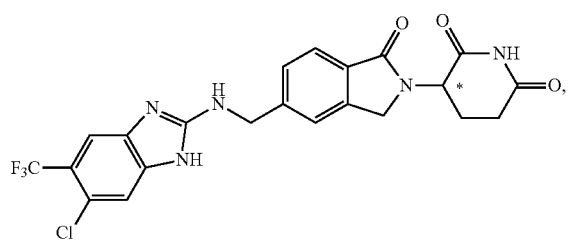
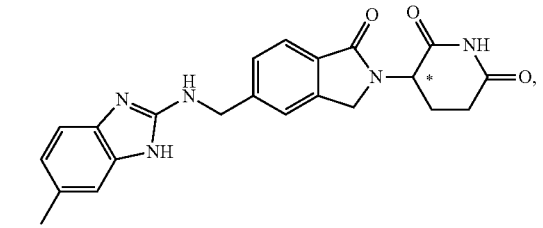
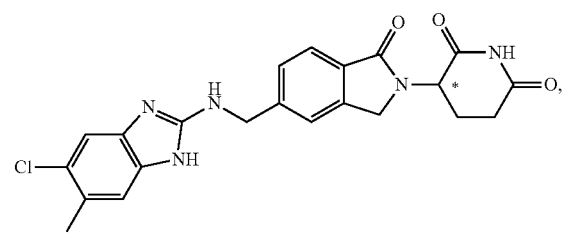
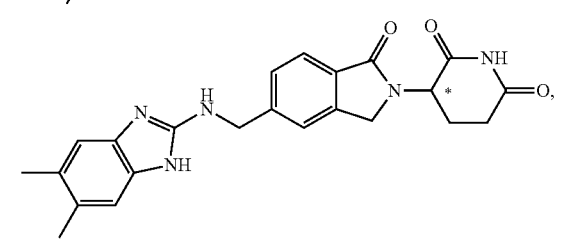
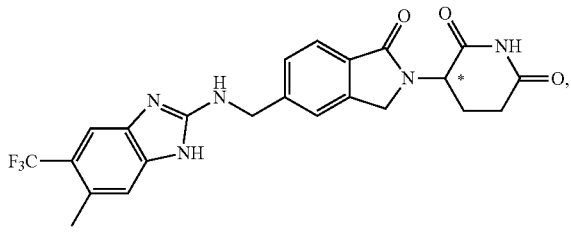
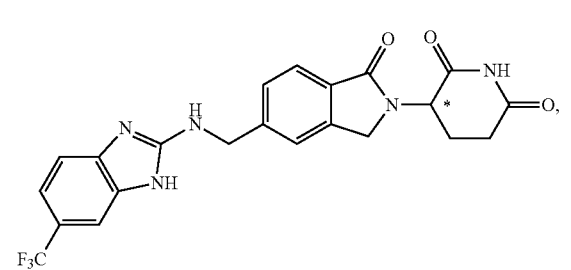
34
-continued
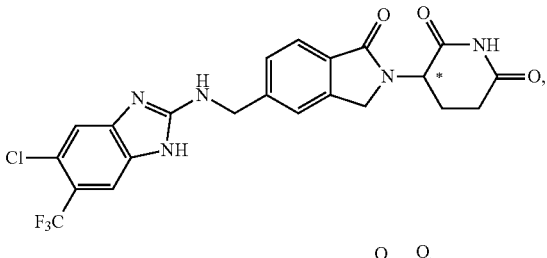
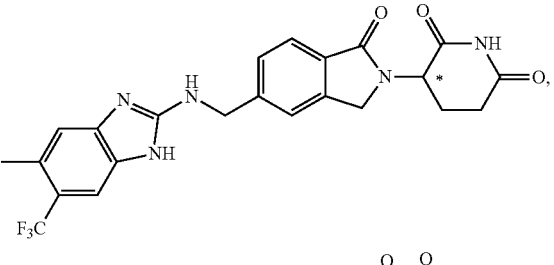
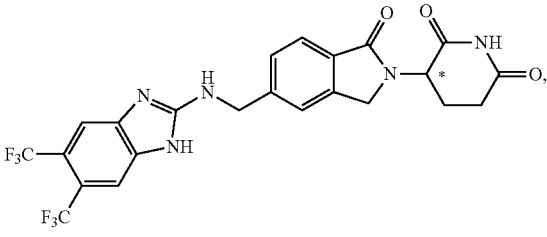
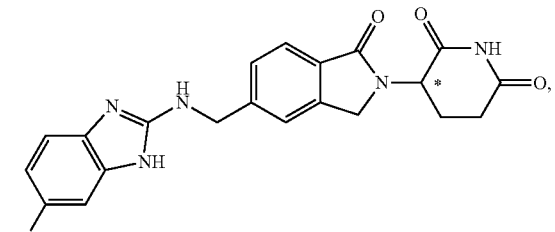
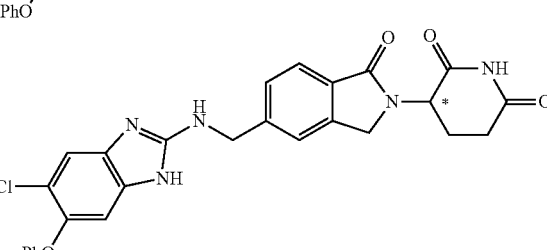
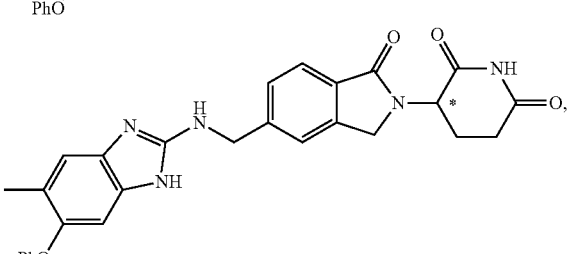
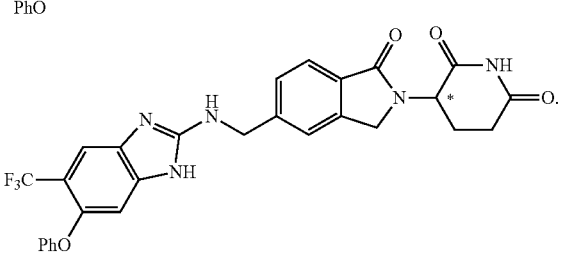

or a pharmaceutically acceptable salt, solvate, prodrug, or stereoisomer thereof.

In yet another embodiment, provided herein is a compound of Formula VI:

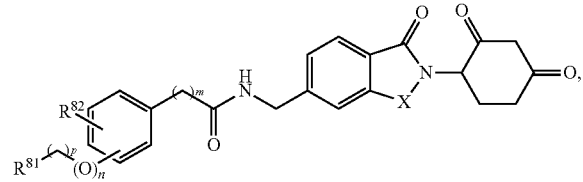

(VI)

or a pharmaceutically acceptable salt, solvate, prodrug, or stereoisomer thereof, wherein:
X is $CH_2$ or $C=O$
m and n are each independently 0 or 1;
p is 0, 1, 2, or 3;
$R^{81}$ is 5 to 6 membered heterocyclyl, optionally substituted with $C_{1-6}$ alkyl; and
$R^{82}$ is hydrogen or halogen.

In one embodiment, X is $CH_2$. In another embodiment, X is $C=O$.

In one embodiment, m is 0. In another embodiment, m is 1. In another embodiment, n is 0. In another embodiment, n is 1.

In one embodiment, p is 0. In another embodiment, p is 1. In another embodiment, p is 2. In another embodiment, p is 3.

In one embodiment, $R^{81}$ is 5 membered heterocycle. In another embodiment, the 5 membered heterocycle is substituted with $C_{1-6}$ alkyl. In another embodiment, $R^{81}$ is 6 membered heterocycle. In another embodiment, the 6 membered heterocycle is substituted with $C_{1-6}$ alkyl.

In one embodiment, $R^{82}$ is hydrogen. In another embodiment, $R^{82}$ is halogen.

In one embodiment, the compound is:

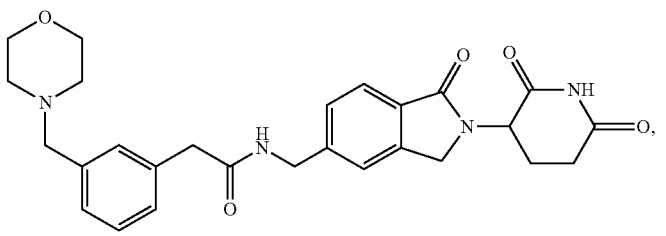

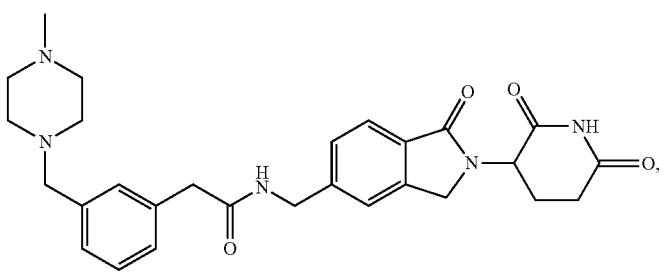

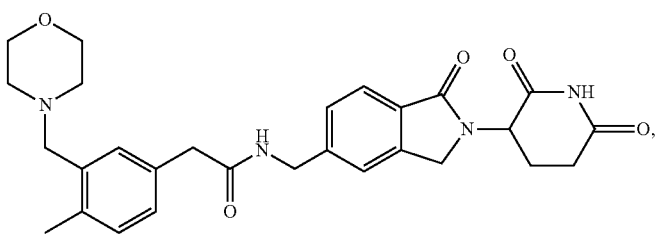

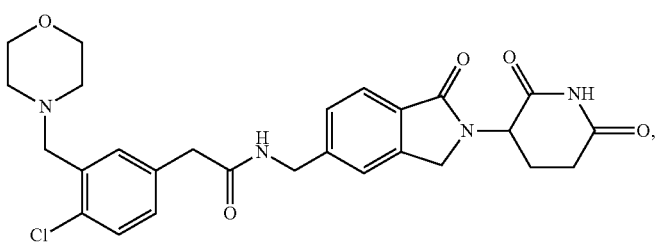

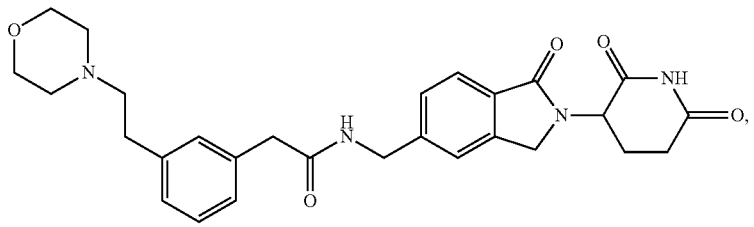

-continued
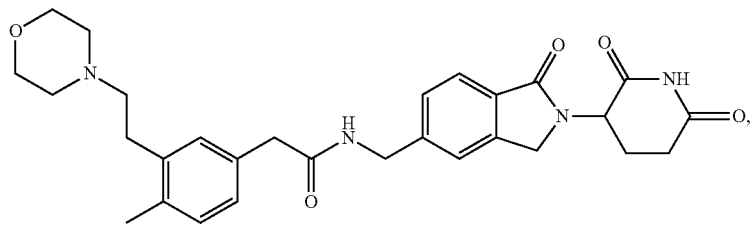
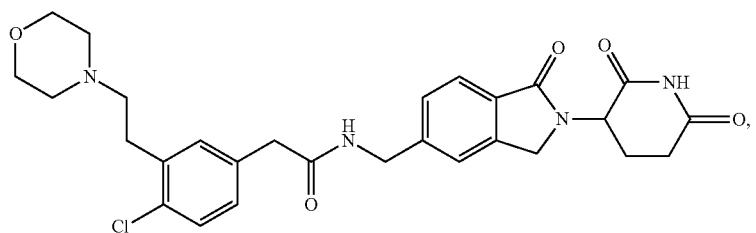
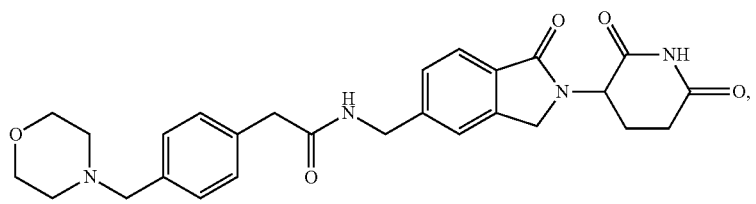
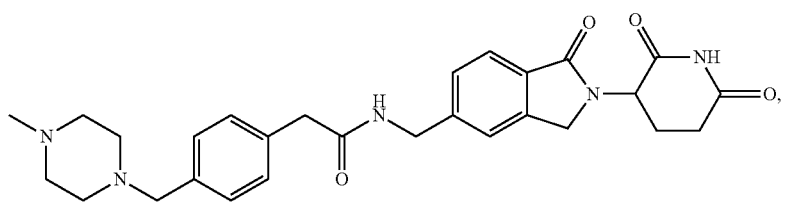
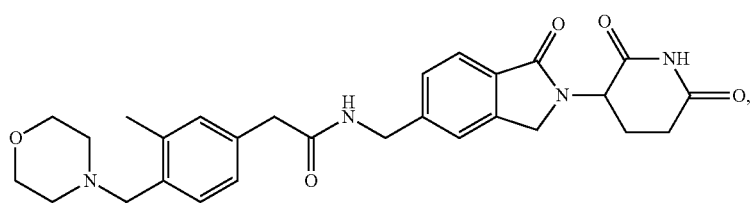
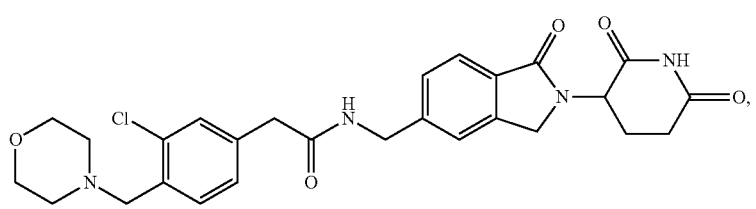
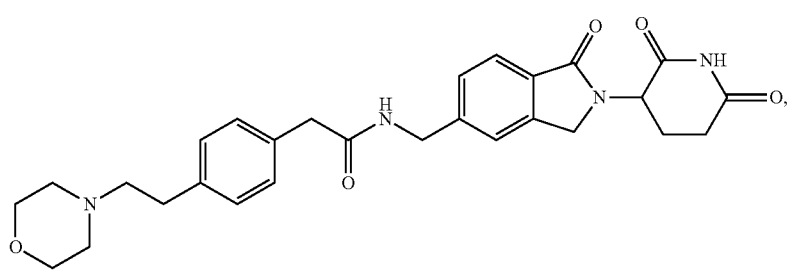

-continued
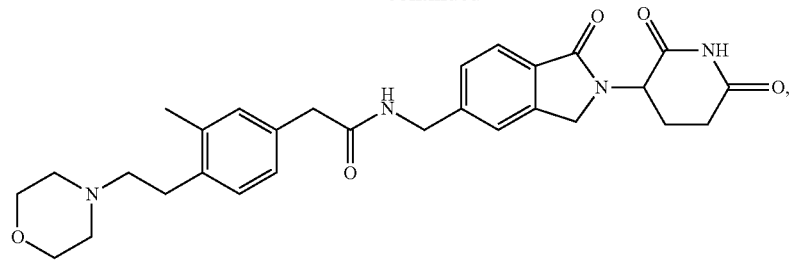
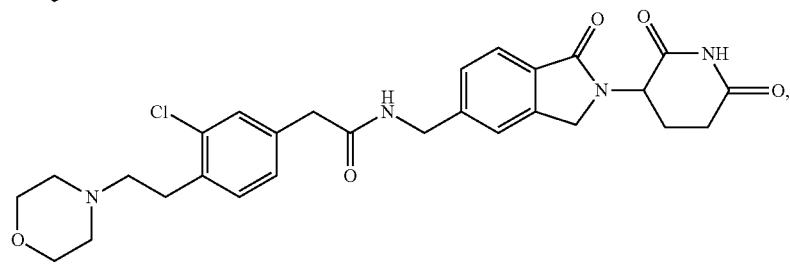
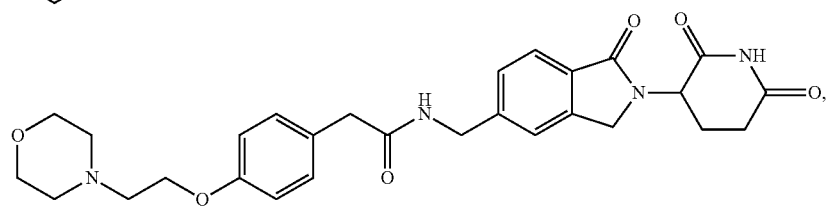
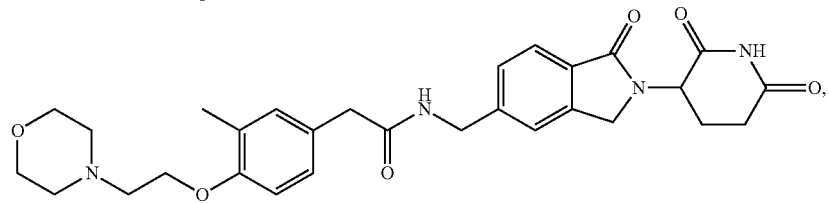
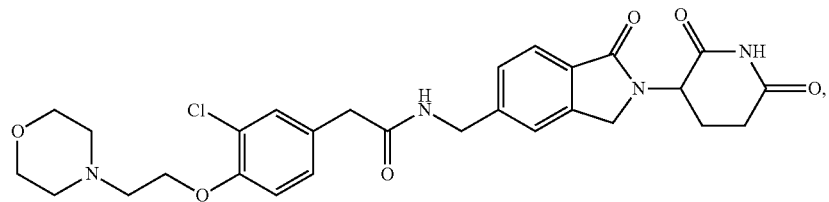
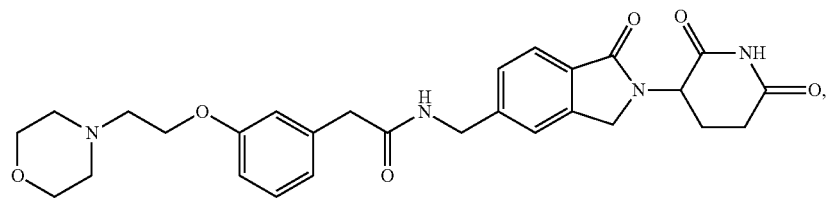
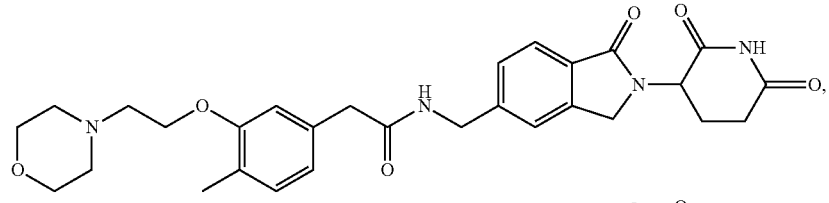
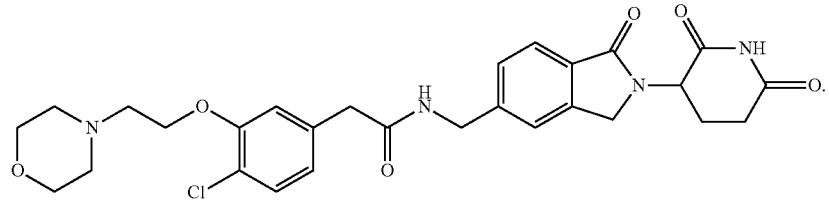

-continued
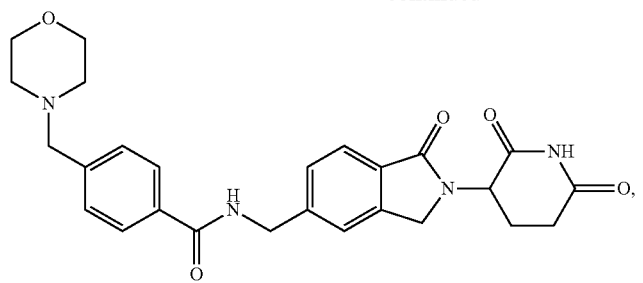
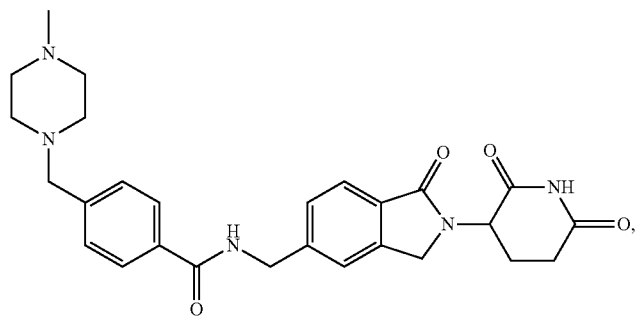
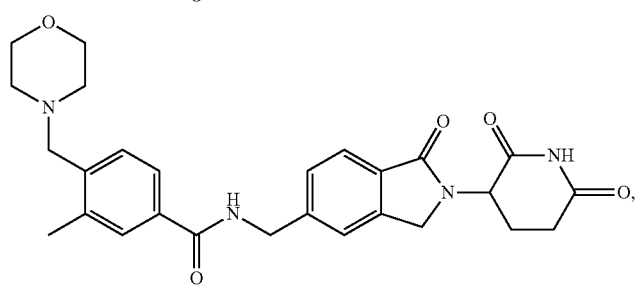
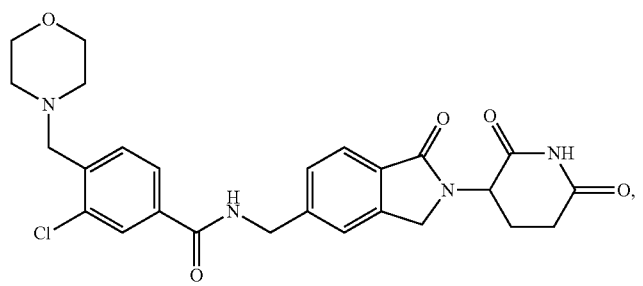
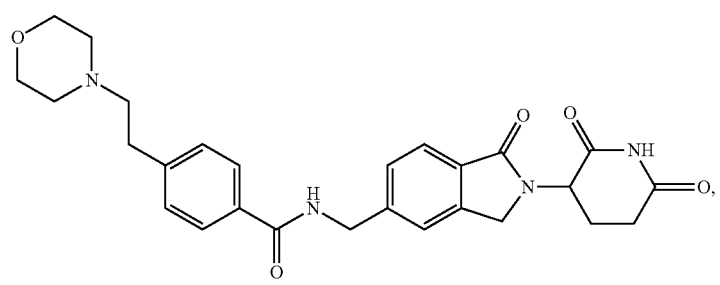
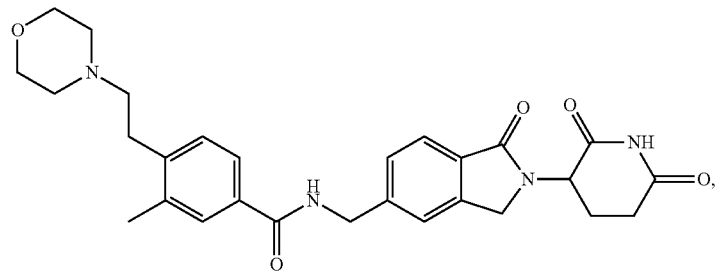

-continued
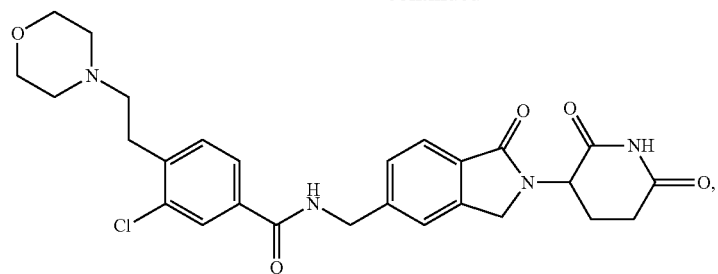
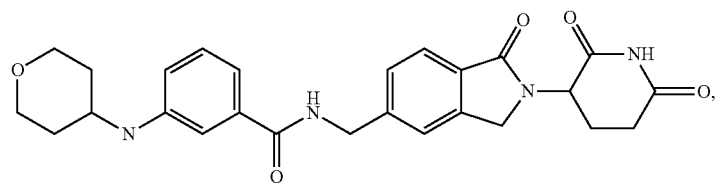
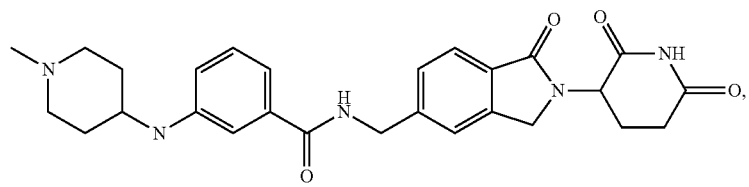
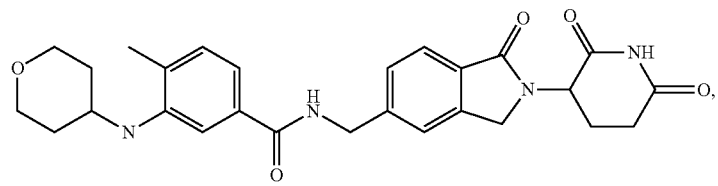
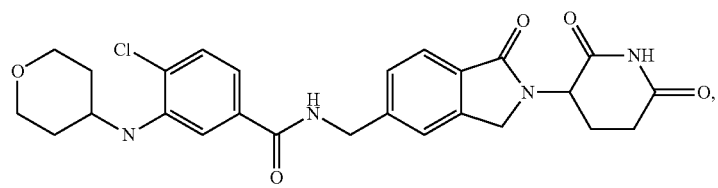
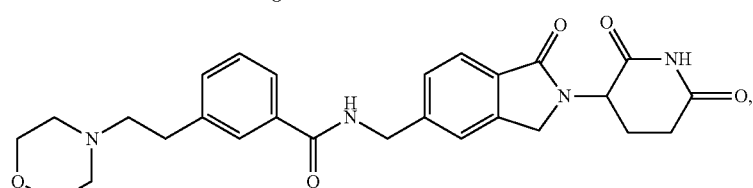
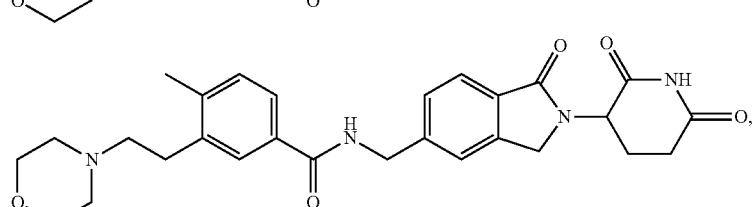
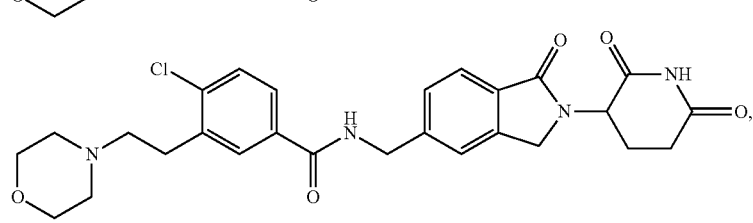

-continued
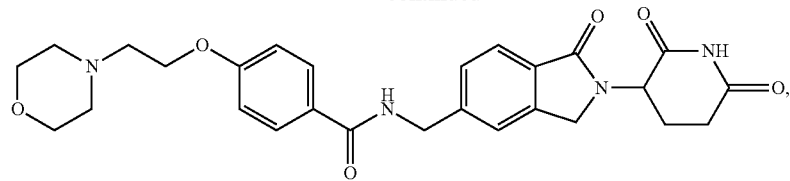
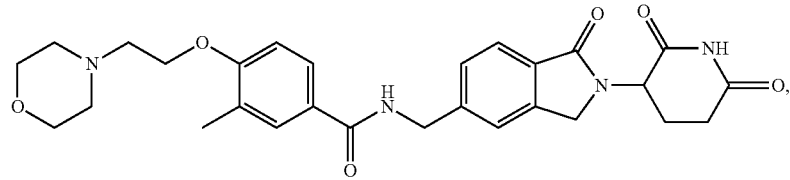
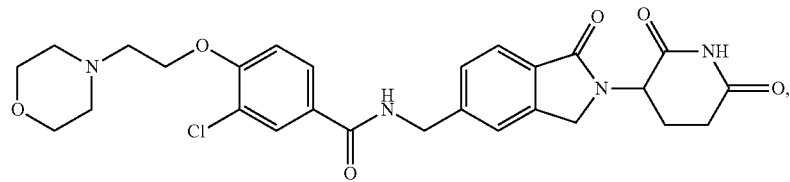
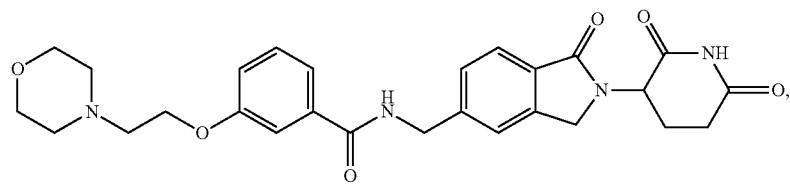
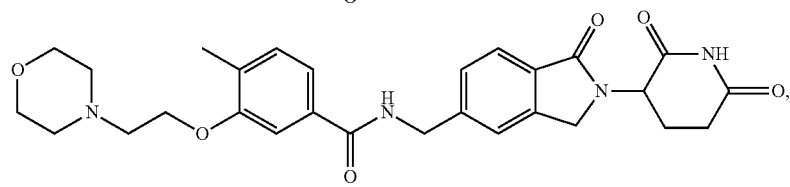
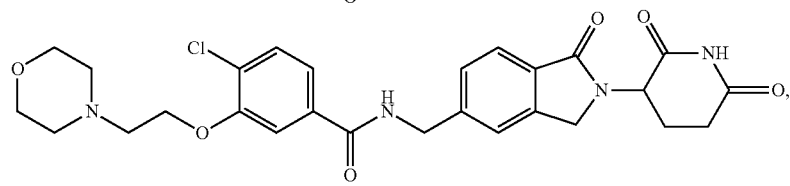
or a pharmaceutically acceptable salt, solvate, prodrug, or stereoisomer thereof.
In yet another embodiment, provided herein is a compound of the following formula:
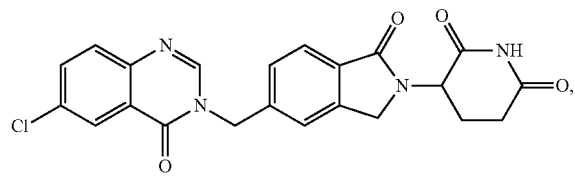
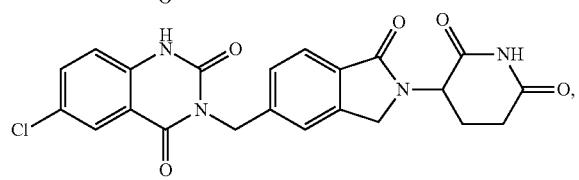
-continued
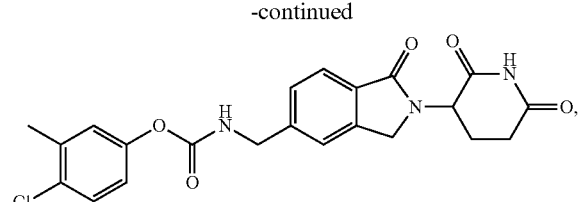
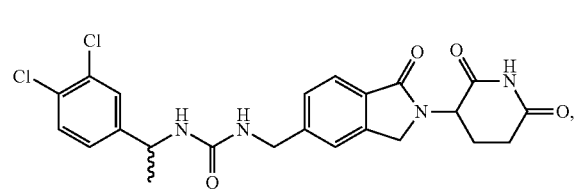

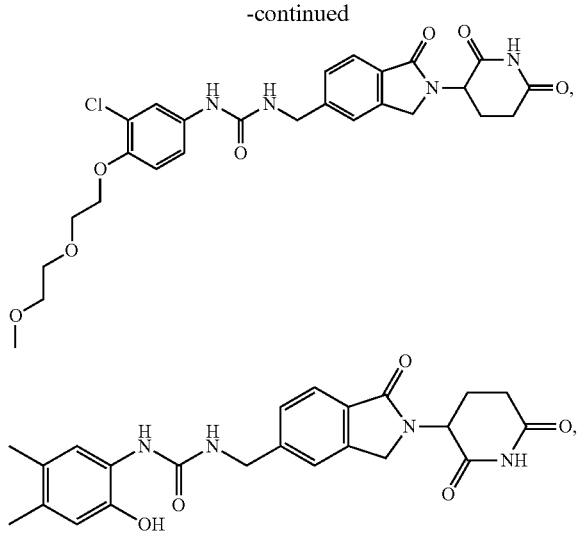

or a pharmaceutically acceptable salt, solvate, prodrug, or stereoisomer thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible via a low energy barrier, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, henzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,*

1977, 409-421; Nathwani and Wood, *Drugs* 1993, 45, 866-94: Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

4.3 Methods of Treatment, Prevention and Management

In one embodiment, provided herein are methods of treating, preventing, and/or managing various diseases or disorders using a compound provided herein, including a single enantiomer, a mixture of enantiomers, or a mixture of diastereomers thereof, or a pharmaceutically acceptable salt, solvate, or prodrug thereof. Without being limited by a particular theory, compounds provided herein can control angiogenesis or inhibit the production of certain cytokines including, but not limited to, TNF-α, IL-1β, IL-12, IL-18, GM-CSF, and/or IL-6. Without being limited by a particular theory, compounds provided herein can stimulate the production of certain other cytokines including IL-10, and also act as a costimulatory signal for T cell activation, resulting in increased production of cytokines such as, but not limited to, IL-12 and/or IFN-γ. In addition, compounds provided herein can enhance the effects of NK cells and antibody-mediated cellular cytotoxicity (ADCC). Further, compounds provided herein may be immunomodulatory and/or cytotoxic, and thus, may be useful as chemotherapeutic agents. Consequently, without being limited by a particular theory, some or all of such characteristics possessed by the compounds provided herein may render them useful in treating, managing, and/or preventing various diseases or disorders. In one embodiment, the compounds provided herein are cytotoxic.

The diseases or disorders treatable with the methods provided herein include, but are not limited to, cancer, disorders associated with angiogenesis, pain including Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα and other cytokines related disorders, and other various diseases and disorders.

Examples of cancer and precancerous conditions include, but are not limited to, those described in U.S. Pat. Nos. 6,281, 230 and 5,635,517 to Muller et al., in various U.S. patent publications to Zeldis, including Publ. Nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in PCT/US04/14004, filed May 5, 2004. All of these references are incorporated herein in their entireties by reference.

Examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; thyroid; kidney; pancreas; bone; spleen; liver; bladder; larynx; nasal passages; and AIDS-related cancers. The compounds provided here are useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing, or managing either primary or metastatic tumors.

Other examples of cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In certain embodiments, the cancer is metastatic. In certain embodiments, the cancer is refractory or resistance to chemotherapy or radiation.

In another embodiment, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. Publ. No. 2006/0030594, published Feb. 9, 2006, which is incorporated in its entirety by reference. The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In yet another embodiment, provided herein are methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent Publ. No. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache, and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade. As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent Publ. No. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. Publ. No. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles. As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trélat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. Publ. No. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vasular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. Publ. No. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. Publ. No. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donovari, L. infanium, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, s. haematobium, Trypanasoma* ssp., *Toxoplasma* ssp., and *O. volvulus*. Other diseases and disorders caused by non-human intracellular parasites such as, but not limited to, *Babesia bovis, Babesia canis, Banesia Gibsoni, Besnoitia darlingi, Cytauxzoon felis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. Publ. No. 2006/0188475, published Aug. 24, 2006, which is incorporated herein by reference. Specific examples include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. Publ. No. 2005/0143344A1, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. Publ. No. 2006/0122228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

Examples of atherosclerosis and related conditions include, but are not limited to, those disclosed in U.S. Publ. No. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated by the disclosure, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated by the disclosure:

| Artery | Body Area Supplied |
|---|---|
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |

-continued

| Artery | Body Area Supplied |
|---|---|
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. Publ. No. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease: SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. Publ. No. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα and other cytokines related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis and other arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; cAMP related disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In certain embodiments, the use of compounds provided herein in various immunological applications, in particular, as vaccine adjuvants, particularly anticancer vaccine adjuvants, as disclosed in U.S. Publ. No. 2007/0048327, published Mar. 1, 2007, which is incorporated herein in its entirety by reference, is also encompassed. This aspect of the disclosure also relates to the uses of compounds provided in combination with vaccines to treat or prevent cancer or infectious diseases, and other various uses of immunomodulatory compounds such as reduction or desensitization of allergic reactions.

Depending on the condition, disorder, or disease to be treated and the subject's condition, a compound provided herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, and/or topical (e.g., transdermal or local) routes of administration, and may be formulated alone or together in suitable dosage unit with a pharmaceutically acceptable vehicle, carrier, diluent, excipient, or a mixture thereof, appropriate for each route of administration.

The dose may be in the form of one, two, three, four, five, six, or more sub-doses that are administered at appropriate intervals per day. The dose or sub-doses can be administered in the form of dosage units containing from about 0.1 to about 1,000 mg, from about 0.1 to about 500 mg, or from 0.5 about to about 100 mg of active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range, the dosage may be about 0.01 to about 0.1, about 0.1 to about 1.0, about 1.0 to about 10, or about 10 to about 50 mg/kg per day.

For oral administration, the pharmaceutical compositions can be provided in the form of tablets containing 1.0 to 1,000 mg of the active ingredient, particularly about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

4.4 Second Active Agents

The compounds provided herein may also be combined or used in combination with other therapeutic agents useful in treating, preventing, and/or managing various diseases or disorders for which the compounds provided herein are useful. It is believed that certain combinations may work synergistically in the treatment of particular types of diseases or disorders, and conditions and symptoms associated with such diseases or disorders. A compound provided herein, including a single enantiomer, a mixture of enantiomers, or a mixture of diastereomers thereof, or a pharmaceutically acceptable salt, solvate, or prodrug thereof, can also work to alleviate adverse effects associated with certain second active agents, and vice versa.

As used herein, the term "in combination" includes the use of more than one therapeutic agents. However, the use of the term "in combination" does not restrict the order or route in which therapeutic agents are administered to a subject with a condition, disorder, or disorder. A first therapeutic agent (e.g., a therapeutic agent such as a compound provided herein) can be administered prior to (e.g., 5 min, 15 min, 30 min, 45 min, 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 12 wks before), concomitantly with, or subsequent to (e.g., 5 min, 15 min, 30 min, 45 min, 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 12 wks after) the administration of a second therapeutic agent to a subject to be treated.

The suitability of a particular route of administration employed for a particular active agent will depend on the active agent itself (e.g., whether it can be administered orally without decomposing prior to entering the blood stream) and the disease being treated. In certain embodiments, the route of administration for compounds provided herein is oral. In certain embodiments, the routes of administration for the second active agents or ingredients provided herein are those as described in *Physicians' Desk Reference,* 1755-1760 (56th ed., 2002).

In one embodiment, the second active agent is administered intravenously or subcutaneously and once or twice daily in an amount of from about 1 to about 1,000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

In certain embodiments, provided herein is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

When a compound provided herein is used contemporaneously with one or more therapeutic agents, a pharmaceutical composition containing such other agents in addition to the compound provided herein may be utilized, but is not required. Accordingly, the pharmaceutical compositions provided herein include those that also contain one or more other therapeutic agents, in addition to a compound provided herein.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40, Herceptin, rituximab); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; entoplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin;

mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; portimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1.25 dihydroxyvitamin D3: 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Similarly, examples of specific second agents according to the indications to be treated, prevented, or managed can be found in the following references, all of which are incorporated herein in their entireties: U.S. Pat. Nos. 6,281,230 and 5,635,517; U.S. application Ser. Nos. 10/411,649, 10/483, 213, 10/411,656, 10/693,794, 10/699,154, and 10/981,189; and U.S. Prov. Appl. Nos. 60/554,923, 60/565,172, 60/626, 975, 60/630,599, 60/631,870, and 60/533,862.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Embrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of second active agents that may be used for the treatment, prevention and/or management of MD and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteportin, purlytin, an angiostatic steroid, rhu-Fab, interferon-2α, pentoxifylline, tin etiopurpurin, motexatin lutetium, 9-fluoro-11,21-dihydroxy-16, 17-1-methylethylidine-bis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001, 368), triamcinolone acetonide, dexamethasone (U.S. Pat. No. 5,770,589), thalidomide, glutathione (U.S. Pat. No. 5,632, 984), basic fibroblast growth factor (bFGF), transforming growth factor b (TGF-b), brain-derived neurotrophic factor (BDNF), plasminogen activator factor type 2 (PAI-2), EYE 101 (Eyetech Pharmaceuticals), LY333531 (Eli Lilly), Miravant, and RETISERT implant (Bausch & Lomb). All of the references cited above are incorporated herein in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hepertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PG12), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), ornapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sultinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetyl leucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may he used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-1 a, and interferon gamma-1 b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The weight ratio of a compound provided herein to the second active ingredient depends upon the effective dose of each ingredient. Generally, an effective dose of each will be used. Thus, for example, when a compound provided herein is combined with a PPAR agonist the weight ratio of the compound provided herein to the PPAR agonist will generally range from about 1000:1 to about 1:1000 or about 200:1 to about 1:200. Combinations of a compound provided herein and other active ingredients will generally also be within the aforementioned range, but in each case, an effective dose of each active ingredient should be used.

4.5 Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In certain embodiments, a compound provided herein is administered daily in a single or divided dose in a four to six week cycle with a rest period of about a week or two weeks. The disclosure further allows the frequency, number, and length of dosing cycles to be increased. In certain embodiments, a compound provided herein is administered for more cycles than are typical when it is administered alone. In certain embodiments, a compound provided herein is administered for a greater number of cycles that would typically cause dose-limiting toxicity in a patient to whom a second active ingredient is not also being administered.

In one embodiment, a compound provided herein is administered daily and continuously for three or four weeks at a dose of from about 0.1 mg to about 500 mg per day, followed by a break of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a break.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle. In certain embodiments, the number of cycles during which the combinatorial treatment is administered to a patient is from about one to about 24 cycles, from about two to about 16 cycles, or from about four to about three cycles.

4.6 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, or prodrug thereof. Pharmaceutical compositions and dosage forms provided herein can further comprise one or more excipients.

Pharmaceutical compositions and dosage forms provided herein can also comprise one or more additional active ingredients. Examples of optional second, or additional, active ingredients are disclosed in Section 4.4, above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this disclosure will vary from one another will be readily apparent to those skilled in the art. See, e.g., *Remington's Pharmaceutical Sciences,* 18th ed., Mack Publishing, Easton Pa. (1990).

In certain embodiments, the pharmaceutical compositions and dosage forms provided herein comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this disclosure encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions provided herein can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In certain embodiments, lactose-free dosage forms provided herein comprise active ingredients, microcrystalline cellulose, pre-gelatinized starch, and magnesium stearate.

This disclosure further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. In certain embodiments, pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. In certain embodiments, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers. Like the amounts and types of excipients, the amounts and specific types of active ingredients in a dosage form may differ depending on factors such as, but not limited to, the route by which it is to be administered to patients. In certain embodiments, dosage forms provided herein comprise a compound provided herein in an amount of from about 0.10 to about 500 mg. In certain embodiments, the dosage forms provided herein comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In certain embodiments, the dosage forms comprise the second active ingredient in an amount of 1 to about 1,000 mg, from about 5 to about 500 mg, from about 10 to about 350 mg, or from about 50 to about 200 mg. Of course, the specific amount of the second active agent will depend on the specific agent used, the type of diseases being treated or managed, and the amount(s) of a compound provided herein and any optional additional active agents concurrently administered to the patient.

4.6.1 Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

In certain embodiments, oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents. Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific hinder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein is present in from about 50 to about 99 weight percent of the pharmaceutical composition or dosage form.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. In certain embodiments, pharmaceutical compositions provided herein comprise from about 0.5 to about 15 weight percent of disintegrant, or from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A solid oral dosage form provided herein comprises a compound provided herein, anhydrous lactose, microcrystalline cellulose, polyvinylpyrrolidone, stearic acid, colloidal anhydrous silica, and gelatin.

4.6.2 Controlled Release Dosage Forms

Active ingredients provided herein can be administered by controlled release means or by delivery devices that are well known to those of ordinary skill in the art. Examples include, but are not limited to, those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein. The disclosure thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.6.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of an immunomodulatory compound provided herein and its derivatives. See, e.g., U.S. Pat. No. 5,134,127, which is incorporated herein by reference.

4.6.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this disclosure are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.7 Kits

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a mixture of an enantiomeric pair, an individual diastereomer, or a mixture of diastereomers thereof; or a pharmaceutically acceptable salt, solvate, or prodrug thereof.

In certain embodiments, the kit includes a container comprising a dosage form of the compound provided herein, including a single enantiomer, a mixture of an enantiomeric pair, an individual diastereomer, or a mixture of diastereomers thereof; or a pharmaceutically acceptable salt, solvate, or prodrug thereof, in a container comprising one or more other therapeutic agent(s) described herein. Kits provided herein can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprotloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

5. EXAMPLES

5.1 1-[2-(2,6-Dioxo-piperidin-3-yl)-1-oxo-2,3-dihydro-1H-isoindol-5-ylmethyl]-3-(4-pyridlin-4-ylmethyl-phenyl)-urea

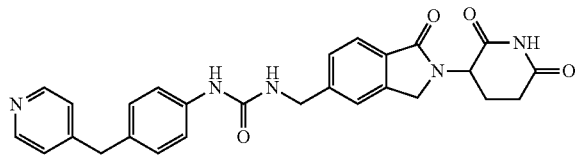

To a suspension of 3-(5-aminomethyl-1-oxo-1,3-dihydro-isoindol-2-yl)-piperidine-2,6-dione methanesulfonic acid salt (0.18 g, 0.5 mmol) in DMF (2 mL) was added CDI (81 mg, 0.5 mmol). The mixture was stirred at RT overnight. 4-Pyridin-4-ylmethyl-phenylamine (92 mg, 0.5 mmol) was added to the mixture and the mixture was stirred at RT for 4 hrs. Then the temperature was elevated to 40° C. and the mixture was stirred at this temperature for 8 hrs. The mixture was cooled to RT, added water (5 mL), and stirred for 10 min. The suspension was filtered and the solid was washed with water (20 mL), EtOAc (20 mL), and $CH_3CN$ (20 mL) to give the product as an off-white solid (100 mg, 41% yield): HPLC: Waters Symmetry $C_{18}$, 5 μm, 3.9×150 mm, 1 mL/min, 240 nm, 5% gradient 100% in 5 min, $CH_3CN/0.1\%$ $H_3PO_4$, 4.69 min (94%); mp: 290-292° C.; $^1$H NMR (DMSO-$d_6$) δ 1.93-2.06 (m, 1H, CHH), 2.29-2.44 (m, 1H, CHH), 2.54-2.68 (m, 1H, CHH), 2.82-3.02 (m, 1H, CHH), 3.88 (s, 2H, $CH_2$), 4.24-4.54 (m, 4H, $C_2$, $CH_2$), 5.10 (dd, J=5.0, 13.7 Hz, 1H, NCH), 6.70 (s, 1H, NH), 7.10 (d, J=8.3 Hz, 2H, Ar), 7.22 (d, J=5.3 Hz, 2H, Ar), 7.34 (d, J=8.3 Hz, 2H, Ar), 7.39-7.48 (m, 1H, Ar), 7.51 (s, 1H, Ar), 7.69 (d, J=7.7 Hz, 1H, Ar), 8.40-8.52 (m, 2H, Ar), 8.59 (s, 1H, NH), 10.98 (s, 1H, NH); $^{13}$C NMR (DMSO-$d_6$) δ 22.49, 31.20, 40.63, 42.76, 47.12, 51.56, 118.03, 121.83, 122.91, 123.99, 126.86, 129.06, 130.27, 132.08, 138.75, 142.36, 144.87, 149.42, 155.22, 163.87, 167.93, 170.98, 172.85; LCMS MH$^+$=484; Anal. Calcd. for $C_{27}H_{25}N_5O_4 + 1.5$ $H_2O$: C, 63.52; H, 5.53; N, 13.72; S, 6.55; Found: C, 63.68; H, 5.24; N, 13.79.

5.2 1-[2-(2,6-Dioxo-piperidin-3-yl)-1-oxo-2,3-dihydro-1H-isoindol-5-ylmethyl]-3-(4-hydroxymethyl-phenyl)-urea

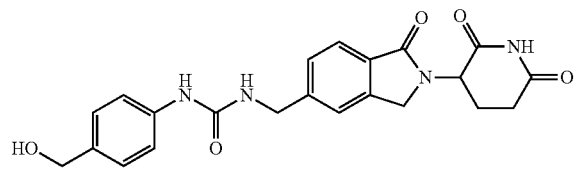

To a suspension of 3-(5-aminomethyl-1-oxo-1,3-dihydro-isoindol-2-yl)-piperidine-2,6-dione methanesulfonic acid salt (0.18 g, 0.5 mmol) in DMF (2 mL) was added CDI (81 mg, 0.5 mmol). The mixture was stirred at RT overnight. 4-Amino-benzyl alcohol (62 mg, 0.5 mmol) was added to the mixture and the mixture was stirred at RT for 4 hrs. Then the temperature was elevated to 40° C. and the mixture was stirred at this temperature for 8 hrs. The mixture was cooled to RT, added water (5 mL) and stirred for 10 min. The suspension was filtered and the solid was washed with water (20 mL), EtOAc (20 mL), and $CH_3CN$ (20 mL) to give a reddish solid (100 mg, 41% yield): The solid was purified on ISCO silica gel column using methanol and DCM as eluent to give the product as a white solid (30 mg, 15% yield): HPLC: Waters Symmetry $C_{18}$, 5 μm, 3.9×150 mm, 1 mL/min, 240 nm, 5% gradient 100% in 5 min, $CH_3CN/0.1\%$ $H_3PO_4$, 4.99 min (97%); mp: 309-311° C.; $^1$H NMR (DMSO-$d_6$) δ 1.92-2.10 (m, 1H, CHH), 2.20-2.47 (m, 1H, CHH), 2.54-2.69 (m, 1H, CHH), 2.80-3.07 (m, 1H, CHH), 4.19-4.54 (m, 6H, $CH_2$, $CH_2$, $CH_2$), 4.94-5.05 (m, 1H, OH), 5.11 (dd, J=5.1, 13.2 Hz, 1H, CHH), 6.70 (t, J=6.0 Hz, 1H, NH), 7.16 (d, J=8.7 Hz, 2H, Ar), 7.28-7.40 (m, 2H, Ar), 7.39-7.48 (m, 1H, Ar), 7.52 (s, 1H, Ar), 7.69 (d, J=7.7 Hz, 1H, Ar), 8.57 (s, 1H, NH), 10.98 (s, 1H, NH); $^{13}$C NMR (DMSO-$d_6$) δ 22.49, 31.18, 42.77, 47.12, 51.56, 62.67, 117.49, 121.89, 122.93, 126.91, 127.05, 130.29, 135.22, 138.99, 142.38, 144.88, 155.25, 167.95, 170.99, 172.85; LCMS MH$^+$=423; Anal. Calcd. for $C_{22}H_{22}N_4O_5 + 0.4$ $H_2O$: C, 61.50; H, 5.35; N, 13.04; Found: C, 61.21; H, 5.05; N, 12.80.

5.3 1-[2-(2,6-Dioxo-piperidio-3-yl)-1-oxo-2,3-dihydro-1H-isoindol-5-ylmethyly]-3-[3-(2-methyl-2H-pyrazol-3-yl)-phenyl]-urea

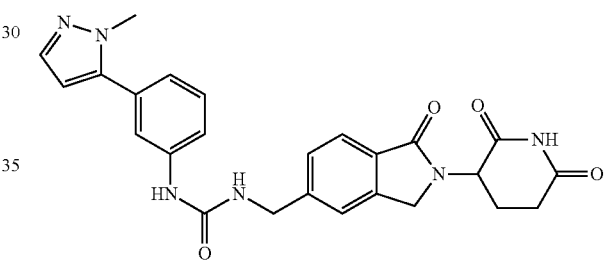

To a mixture of 5-(3-isocyanato-phenyl)-1-methyl-1H-pyrazole (0.22 g, 1.1 mmol) and 3-(5-aminomethyl-1-oxo-1,3-dihydro-isoindol-2-yl)-piperidine-2.6-dione methanesulfonic acid salt (0.40 g, 1.1 mmol) in acetonitrile (5 mL) was added TEA (0.31 mL, 2.2 mmol) at RT, and the mixture was kept for 22 hrs. Water (25 mL) was added to the mixture and the mixture was stirred at RT for 3 hrs. The suspension was filtered and the solid was washed with water (20 mL), EtOAc (20 mL), and water (20 mL) to give a solid. The solid was purified with preparative HPLC to give the product as a white solid (122 mg, 24% yield): HPLC: Waters Symmetry $C_{18}$, 5 μm, 3.9×150 mm, 1 mL/min, 240 nm, 30/70 $CH_3CN/$ 0.1% $H_3PO_4$, 3.34 min (99.8%); mp: 260-262° C.; $^1$H NMR (DMSO-$d_6$) δ 1.88-2.10 (m, 1H, CHH), 2.27-2.47 (m, 1H, CHH), 2.55-2.66 (m, 1H, CHH), 2.80-3.02 (m, 1H, CHH), 3.84 (s, 3H, $CH_3$), 4.30 (d, J=17.6 Hz, 1H, CHH), 4.40-4.50 (m, 3H, CHH, $CH_2$), 5.11 (dd, J=5.2, 13.3 Hz, 1H, NCH), 6.35 (d, J=1.9 Hz, 1H, Ar), 6.83 (t, J=6.1 Hz, 1H, NH), 7.06 (dt, J=1.4, 7.6 Hz, 1H, Ar), 7.31-7.38 (m, 1H, Ar), 7.40-7.48 (m, 3H, Ar), 7.53 (d, J=0.4 Hz, 1H, Ar), 7.63 (t, J=1.9 Hz, 1H, Ar), 7.70 (d, J=7.9 Hz, 1H, Ar), 8.82 (s, 1H, NH), 10.98 (br. s., 1H, NH); $^{13}$C NMR (DMSO-$d_6$) δ 22.48, 31.19, 37.45, 42.78, 47.11, 51.55, 105.55, 117.62 (2 carbons by HMQC), 121.18, 121.87, 122.93, 126.87, 129.08, 130.29, 130.51, 137.86, 140.73, 142.38, 142.82, 144.76, 155.21, 167.94, 170.98, 172.84; LCMS MH$^+$=473; Anal. Calcd. for $C_{25}H_{24}N_6O_4$: C, 63.55; H, 5.12; N, 17.79; Found: C, 63.36; H, 5.17; N, 17.72.

5.4 1-[2-(2,6-Dioxo-piperidin-3-yl)-1-oxo-2,3-dihydro-1H-isoindol-5-ylmethyl]-3-[3-(2-methyl-imidazol-1-yl)-phenyl]-urea; Formic Acid

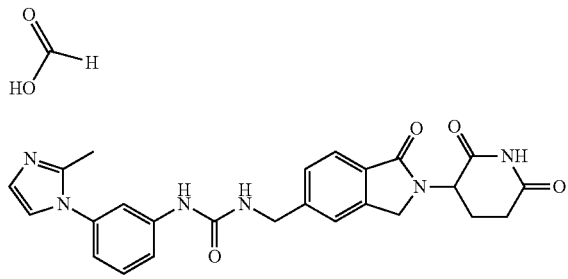

A mixture of 3-(5-aminomethyl-1-oxo-1,3-dihydro-isoindol-2-yl)-piperidine-2,6-dione methanesulfonic acid salt (0.40 g, 1.1 mmol) and CDI (0.19 g, 1.2 mmol) in DMF (5 mL) was stirred at RT for 18 hrs. To the mixture was added 3-(2-methyl-imidazol-1-yl)-phenylamine (0.19 g, 1.1 mmol) at RT, and the mixture was stirred at 60° C. for 24 hrs. To the mixture was added water (25 mL) and ether (20 mL). The mixture was stirred at RT for 2 hrs. The suspension was filtered and the solid was washed with water (20 mL), ethyl acetate (20 mL), and water (20 mL) to give a solid. The solid was purified with preparative HPLC to give the product as a white solid (100 mg, 20% yield): HPLC: Waters Symmetry $C_{18}$, 5 μm, 3.9×150 mm, 1 mL/min, 240 nm, 5% gradient 95% in 5 min, $CH_3CN/0.1\% H_3PO_4$, 4.48 min (96.8%); mp: 218-220° C.; $^1$H NMR (DMSO-$d_6$) δ 1.89-2.12 (m, 1H, CHH), 2.25-2.29 (m, 3H, $CH_3$), 2.30-2.46 (m, 1H, CHH), 2.54-2.68 (m, 1H, CHH), 2.78-3.04 (m, 1H, CHH), 4.31 (d, J=17.4 Hz, 1H, CHH), 4.38-4.53 (m, 3H, CHH, $CH_2$), 5.11 (dd, J=5.1, 13.2 Hz, 1H, NCH), 6.89 (d, J=1.3 Hz, 1H, Ar), 6.92-7.05 (m, 2H, Ar, NH), 7.23 (d, J=1.3 Hz, 1H, Ar), 7.32-7.40 (m, 2H, Ar), 7.41-7.49 (m, 1H, Ar), 7.52 (s, 1H, Ar), 7.57-7.65 (m, 1H, Ar), 7.69 (d, J=7.9 Hz, 1H, Ar), 8.18 (s, 1H, HCOOH), 9.03 (s, 1H, NH), 10.98 (s, 1H, NH); $^{13}$C NMR (DMSO-$d_6$) δ 13.60, 22.49, 31.20, 42.77, 47.12, 51.58, 114.22, 116.89, 117.61, 120.68, 121.88, 122.93, 126.89, 127.13, 129.63, 130.30, 137.90, 141.50, 142.38, 143.43, 144.69, 155.16, 163.44, 167.93, 170.98, 172.85; LCMS MH$^+$=473: Anal. Calcd. for $C_{25}H_{24}N_6O_4$+HCOOH+1.5 $H_2O$: C, 57.24; H, 5.36; N, 15.40; Found: C, 57.43; H, 5.11; N, 15.57.

5.5 1-[2-(2,6-Dioxo-piperidin-3-yl)-1-oxo-2,3-dihydro-1H-isoindol-5-ylmethyl]-3-[4-(4-methyl-4H-[1,2,4]triazol-3-yl)-phenyl]-urea

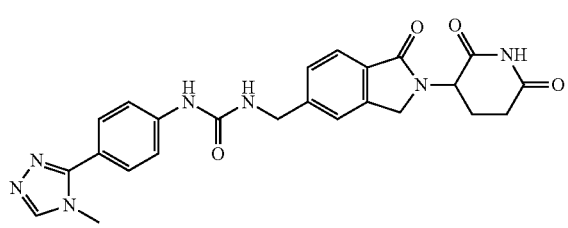

To a stirred suspension of 4-(4-methyl-4H-[1,2,4]triazol-3-yl)-phenylamine (0.31 g, 1.77 mmol) in DMF (10 mL) at 40° C. was added CDI (0.32 g, 1.94 mmol). The mixture was stirred for 15 min, followed by addition of 3-(5-aminomethyl-1-oxo-1,3-dihydro-isoindol-2-yl)-piperidine-2,6-dione methanesulfonic acid salt (0.65 g, 1.77 mmol). Heating was stopped after 1.5 hrs and the mixture was stirred at RT overnight. Solvent was evaporated and the residue was purified by preparative HPLC to give the product as a white solid (0.13 g, 15% yield): HPLC, Waters Symmetry $C_{18}$, 5 μm, 3.9×150 mm, 1 ml/min, 240 nm, 14/86 $CH_3CN/0.1\% H_3PO_4$, 4.70 min (93.9%); mp, 248-250° C.; $^1$H NMR (DMSO-$d_6$) δ 1.93-2.06 (m, 1H, CHH), 2.29-2.46 (m, 1H, CHH), 2.55-2.70 (m, 1H, CHH), 2.82-3.02 (m, 1H, CHH), 3.72 (s, 3H, $CH_3$), 4.24-4.55 (m, 4H, $CH_2$, $CH_2$), 5.11 (dd, J=4.9, 13.2 Hz, 1H, NCH), 6.95 (t, J=5.7 Hz, 1H, NH), 7.41-7.81 (m, 7H, ArH), 8.51 (s, 1H, ArH), 9.02 (s, 1H, NH), 10.99 (s, 1H, NH); $^{13}$C NMR (DMSO-$d_6$) δ 22.49, 31.20, 31.94, 42.79, 47.13, 51.58, 117.50, 119.49, 121.88, 122.94, 126.91, 128.80, 130.32, 141.84, 142.39, 144.72, 145.76, 153.08, 155.12, 167.95, 170.99, 172.85; LC/MS MH$^+$=474: Anal. Calcd. For $C_{24}H_{23}N_7O_4$: C, 60.88; H, 4.90; N, 20.71. Found: C, 58.28; H, 4.67; N, 19.49 (Note: This analysis was off, and both HPLC and $^1$H NMR showed 6% impurity).

5.6 1-[2-(2,6-Dioxo-piperidin-3-yl)-1-oxo-2,3-dihydro-1H-isoindol-5-ylmethyl]-3-[3-(2-methyl-thiazol-4-yl)-phenyl]-urea

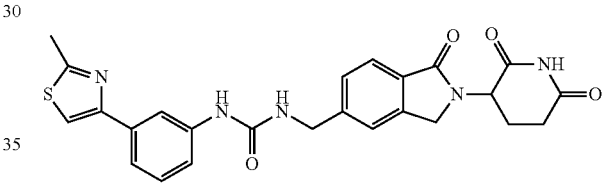

To a mixture of 4-(3-isocyanato-phenyl)-2-methyl-thiazole (0.25 g, 1.2 mmol) and 3-(5-aminomethyl-1-oxo-1,3-dihydro-isoindol-2-yl)-piperidine-2,6-dione methanesulfonic acid salt (0.43 g, 1.2 mmol) in acetonitrile (5 mL) was added TEA (0.33 mL, 2.3 mmol) at RT, and the mixture was kept for 3 hrs. Water (25 mL) was added to the mixture and the mixture was stirred at RT for 3 hrs. The suspension was filtered and the solid was washed with water (20 mL), ethyl acetate (20 mL), and water (20 mL) to give a solid. The solid was purified with preparative HPLC to give the product as a white solid (160 mg, 28% yield): HPLC: Waters Symmetry $C_{18}$, 5 μm, 3.9× 150 mm, 1 mL/min, 240 nm, 30/70 $CH_3CN/0.1\% H_3PO_4$, 5.93 min (99.4%); mp: 252-254° C.; $^1$H NMR (DMSO-$d_6$)δ 1.92-2.06 (m, 1H, CHH), 2.27-2.47 (m, 1H, CHH), 2.54-2.66 (m, 1H, CHH), 2.71 (s, 3H, $CH_3$), 2.81-3.01 (m, 1H, CHH), 4.31 (d, J=17.6 Hz, 1H, CHH), 4.38-4.53 (m, 3H, CHH, $CH_2$), 5.11 (dd, J=5.1, 13.2 Hz, 1H, NCH), 6.74 (t, J=6.0 Hz, 1H, NH), 7.20-7.32 (m, 1H, Ar), 7.40 (ddd, J=1.1, 2.3, 8.1 Hz, 1H, Ar), 7.46 (dq, J=1.4, 7.6 Hz, 2H, Ar), 7.53 (s, 1H, Ar), 7.70 (d, J=7.9 Hz, 1H, Ar), 7.81 (s, 1H, Ar), 8.02 (t, J=1.9 Hz, 1H, Ar), 8.79 (s, 1H, NH), 10.98 (s, 1H, NH); $^{13}$C NMR (DMSO-$d_6$) δ 18.91, 22.51, 31.18, 42.79, 47.12, 51.56, 113.55, 115.55, 117.28, 118.86, 121.86, 122.94, 126.89, 129.01, 130.29, 134.58, 140.82, 142.39, 144.90, 153.89, 155.21, 165.29, 167.95, 170.99, 172.85; LCMS MH$^+$=490; Anal. Calcd. for $C_{25}H_{23}N_5O_4S$: C, 61.34; H, 4.74; N, 14.31; S, 6.55; Found: C, 61.09; H, 4.60; N, 14.19; S, 6.49.

5.7 1-[2-(2,6-Dioxo-piperidin-3-yl)-1-oxo-2,3-dihydro-1H-isoindol-5-ylmethyl]-3-[3-(1-methyl-1H-pyrazol-3-yl)-phenyl]-urea

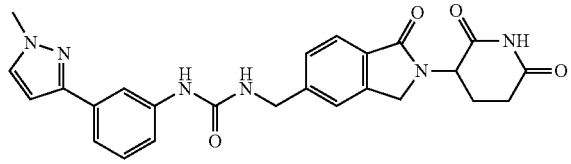

To a stirred suspension of 3-(3-isocyanato-phenyl)-1-methyl-1H-pyrazole (0.25 g, 125 mmol) and 3-(5-aminomethyl-1-oxo-1,3-dihydro-isoindol-2-yl)-piperidine-2,6-dione methanesulfonic acid salt (0.46 g, 1.25 mmol) in acetonitrile (5 mL) at RT was added TEA (0.35 mL, 2.51 mmol). The mixture was stirred for 4 hrs, followed by addition of 1N HCl (10 mL), which was stirred for 10 min. The mixture was purified by preparative HPLC to give the product as an off-white solid (0.22 g, 38% yield): HPLC, Waters Symmetry $C_{18}$, 5 μm, 3.9×150 mm, 1 ml/min, 240 nm. 25/75 $CH_3CN$/0.1% $H_3PO_4$, 5.99 min (99.9%): mp, 232-234° C.; $^1H$ NMR (DMSO-$d_6$) δ 1.93-2.07 (m, 1H, CHH), 2.29-2.46 (m, 1H, CHH), 2.55-2.68 (m, 1H, CHH), 2.82-3.01 (m, 1H, CHH), 3.87 (s, 3H, $CH_3$), 4.24-4.55 (m, 4H, $CH_2$, $CH_2$), 5.11 (dd, J=5.0, 13.3 Hz, 1H, NCH), 6.57 (d, J=2.3 Hz, 1H, ArH), 6.73 (t, J=5.9 Hz, 1H, NH), 7.18-7.37 (m, 3H, ArH), 7.46 (d, J=7.9 Hz, 1H, ArH), 7.53 (s, 1H, ArH), 7.65-7.77 (m, 2H, ArH), 7.89 (s, 1H, ArH), 8.71 (s, 1H, NH), 10.98 (s, 1H, NH); $^{13}C$ NMR (DMSO-$d_6$) δ 22.51, 31.18, 38.60, 42.79, 47.13, 51.58, 102.33, 114.31, 116.77, 118.16, 121.86, 122.93, 126.89, 128.85, 130.29, 132.17, 133.85, 140.66, 142.39, 144.91, 150.03, 155.22, 167.95, 170.99, 172.85; LC/MS $MH^+$=473; Anal. Calcd. For $C_{25}H_{24}N_6O_4$+0.5 $H_2O$: C, 62.36; H, 5.23; N, 17.45. Found: C, 62.06; H, 5.19; N, 17.28.

5.8 1-((2-(2,6-dioxopiperidin-3-yl)-1-oxoisoindolin-5-yl)methyl)-3-(3-(morpholinomethyl)phenyl)urea Formate

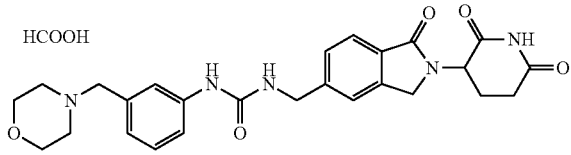

To a stirred mixture of 3-(5-aminomethyl-1-oxo-1,3-dihydro-isoindol-2-yl)-piperidine-2,6-dione hydrochloride (0.37 g, 1.00 mmol) and 4-(3-isocyanatobenzyl)-morpholine (0.22 g, 1.00 mmol) in acetonitrile (10 mL) was added TEA (0.28 mL, 2.00 mmol) at RT under nitrogen. After 2 hrs, additional 4-(3-isocyanatobenzyl)morpholine (0.22 g, 1.00 mmol) and TEA (0.28 mL, 2.00 mmol) were added. After 12 hrs, undesired solid was filtered and filtrate was concentrated. The residue was dissolved in acetonitrile and was purified by preparative HPLC (gradient: $CH_3CN$+0.1% formic acid/$H_2O$+0.1% formic acid: 10/90 for 5 min, to 100/0 in 10 min, 100/0 for 5 min). After evaporation of the solvent, the residue was triturated in ether (20 mL) for 1 hr. The product was then isolated by filtration and dried in vacuo to give the product as a beige solid (0.16 g, 30% yield): HPLC: Waters Symmetry $C_{18}$, 5 μm, 3.9×150 mm, 1 mL/min, 240 nm, gradient: $CH_3CN$/0.1% $H_3PO_4$: 10/90 to 90/10 in 10 min, 90/10 (5 min): 4.64 min (95.84%); mp: 198-200° C.; $^1H$ NMR (DMSO-$d_6$) δ 1.83-2.12 (m, 1H, CHH), 2.21-2.47 (m, 5H, CHH, $CH_2$, $CH_2$), 2.54-2.69 (m, J=11.0 Hz, 1H, CHH), 2.79-3.03 (m, 1H, CHH), 3.38 (s, 2H, $CH_2$), 3.52-3.72 (m, 4H, $CH_2$, $CH_2$), 4.31 (d, J=17.2 Hz, 1H, CHH), 4.37-4.55 (m, 3H, CHH, $CH_2$), 5.11 (dd, J=5.1, 13.2 Hz, 1H, CH), 6.83 (d, J=7.6 Hz, 1H, Ar), 6.99 (t, J=5.6 Hz, 1H, NH), 7.15 (t, J=7.7 Hz, 1H, Ar), 7.32 (d, J=8.3 Hz, 1H, Ar), 7.39 (s, 1H, Ar), 7.44 (d, J=7.7 Hz, 1H, Ar), 7.52 (s, 1H, Ar), 7.69 (d, J=7.7 Hz, 1H, Ar), 8.29 (br. s., 1H, HCOO), 8.90 (s, 1H, NH), 10.98 (br. s., 1H, NH); $^{13}C$ NMR (DMSO-$d_6$) δ 22.51, 31.20, 42.73, 47.12, 51.56, 53.20, 62.69, 66.17, 116.42, 118.13, 121.72, 121.83, 122.90, 126.86, 128.34, 130.25, 138.24, 140.48, 142.36, 144.99, 155.31, 164.30, 167.95, 170.98, 172.85: LCMS: $MH^+$=492; Anal. Calcd. for $C_{27}H_{31}N_5O_7$+3 $H_2O$: C, 54.82; H, 6.30; N, 11.84; Found: C, 55.12; H, 6.12; N, 11.72.

5.9 1-((2-(2,6-dioxopiperidin-3-yl)-1-oxoisoindolin-5-yl)methyl)-3-(4-methyl-3-nitrophenyl)urea

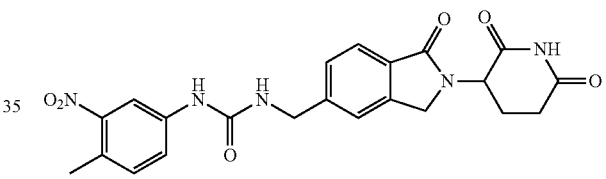

To a stirred mixture of 3-(5-aminomethyl-1-oxo-1,3-dihydro-isoindol-2-yl)-piperidine-2,6-dione hydrochloride (1.00 g, 2.70 mmol) and 4-methyl-3-nitrophenylisocyanate (0.48 mL, 2.70 mmol) in acetonitrile (20 mL) was added TEA (0.75 mL, 5.40 mmol) at RT under nitrogen. After 2 hrs, 1N HCl (20 mL) was added and the solids were isolated by filtration and washed with water (3×20 mL). The crude product was triturated in EtOAc (50 mL) for 12 hrs. The product was isolated by filtration and dried in vacuo to give the product as a yellow solid (0.74 g, 61% yield): HPLC: Waters Symmetry $C_{18}$, 5 μm, 3.9×150 mm, 1 mL/min, 240 nm, gradient: $CH_3CN$/0.1% $H_3PO_4$: 10/90 to 90/10 in 10 min, 90/10 (5 min): 7.94 min (96.79%); mp: 230-232° C.; $^1H$ NMR (DMSO-$d_6$) δ 1.87-2.08 (m, 1H, CHH), 2.26-2.48 (m, 3H, CHH, $CH_3$), 2.60 (d, J=17.6 Hz, 1H, CHH), 2.79-3.07 (m, 1H, CHH), 4.31 (d, J=17.4 Hz, 1H, CHH), 4.38-4.55 (m, 3H, CHH, $CH_2$), 5.11 (dd, J=5.0, 13.3 Hz, 1H, CH), 6.92 (t, J=5.9 Hz, 1H, NH), 7.34 (d, J=8.3 Hz, 1H, Ar), 7.45 (d, J=7.9 Hz, 1H, Ar), 7.49-7.60 (m, 2H, Ar), 7.70 (d, J=7.7 Hz, 1H, Ar), 8.26 (d, J=2.3 Hz, 1H, Ar), 9.07 (s, 1H, NH), 10.99 (s, 1H, NH); $^{13}C$ NMR (DMSO-$d_6$) δ 18.95, 22.49, 31.20, 42.82, 47.12, 51.56, 112.74, 121.92, 122.45, 122.94, 124.71, 126.92, 130.33, 132.84, 139.46, 142.38, 144.59, 148.72, 155.02, 167.93, 170.98, 172.85; LCMS: $MH^+$=452; Anal. Calcd. for $C_{22}H_{21}N_4O_6$: C, 58.53; H, 4.69; N, 15.51; Found: C, 58.23; H, 4.58; N, 15.34.

5.10 1-(3-amino-4-methylphenyl)-3-((2-(2,6-dioxopiperidin-3-yl)-1-oxoisoindolin-5-yl)methyl)urea

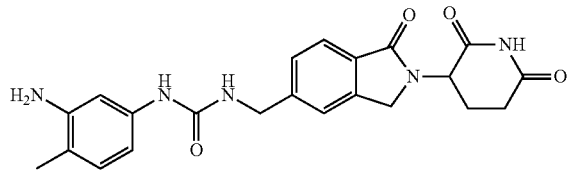

To a solution of 1-((2-(2,6-dioxopiperidin-3-yl)-1-oxoisoindolin-5-yl)methyl)-3-(4-methyl-3-nitrophenyl)urea (0.30 g, 0.66 mmol) in DMF (50 mL) was added Pd-C (0.10 g, 10% weight). The reaction mixture was hydrogenated with a Parr-shaker at 55 psi. After 16 hrs, the mixture was filtered through a celite pad, which was washed with additional DMF (20 mL). The filtrate was then evaporated and the residue was stirred in water (100 mL) for 3 hrs. The solid was filtered, washed with additional water (50 mL), and dried. The crude green product was dissolved in DMF (100 mL), decolorizing carbon was added, and the reaction mixture was stirred for 3 hrs. The mixture was then filtered through a celite pad, which was washed with additional DMF (50 mL). The filtrate was then evaporated and the residue was stirred in water (100 mL) for 4 hrs. The solid was filtered, washed with additional water (50 mL), and dried in vacuo. The solid was triturated with ether for 1 hr and the product was isolated by filtration to give the product as a pale green solid (0.22 g, 79% yield): HPLC: Waters Symmetry $C_{18}$, 5 μm, 3.9×150 mm, 1 mL/min, 240 nm, gradient: $CH_3CN/0.1\% H_3PO_4$: 10/90 to 90/10 in 10 min, 90/10 (5 min): 4.50 min (96.74%); mp: 228-230° C.; $^1H$ NMR (DMSO-$d_6$) δ 1.82-2.10 (m, 4H, CHH, CH3), 2.25-2.47 (m, 1H, CHH), 2.59 (d, J=18.3 Hz, 1H, CHH), 2.77-3.02 (m, 1H, CHH), 4.30 (d, J=17.6 Hz, 1H, CHH), 4.35-4.53 (m, 3H, $CH_2$, CHH), 4.93 (br. s., 2H, $NH_2$), 5.11 (dd, J=5.0, 12.9 Hz, 1H, CH), 6.51 (dd, J=1.9, 7.9 Hz, 1H, Ar), 6.58 (t, J=5.7 Hz, 1H, NH), 6.75 (d, J=8.5 Hz, 2H, Ar), 7.43 (d, J=7.9 Hz, 1H, Ar), 7.50 (s, 1H, Ar), 7.69 (d, J=7.7 Hz, 1H, Ar), 8.23 (s, 1H, NH), 10.98 (s, 1H, NH); $^{13}C$ NMR (DMSO-$d_6$) δ 16.75, 22.49, 31.20, 42.74, 47.10, 51.56, 104.16, 106.57, 114.59, 121.86, 122.90, 126.89, 129.79, 130.25, 138.75, 142.36, 145.06, 146.12, 155.22, 167.95, 170.98, 172.85; LCMS: $MH^+$=422; Anal. Calcd. for $C_{22}H_{23}N_5O_4$+0.1 $H_2O$+0.5 $Et_2O$: C, 62.62; H, 6.17; N, 15.21; Found: C, 62.30; H, 5.89; N, 14.89.

5.11 1-[2-(2,6-Dioxo-piperidin-3-yl)-1-oxo-2,3-dihydro-1H-isoindol-5-ylmethyl]-3-(3-phenoxy-phenyl)-urea

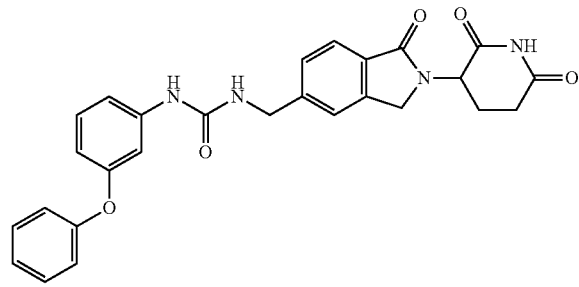

TEA (0.20 g, 2.00 mmol) was added to a stirred mixture of 3-(5-aminomethyl-1-oxo-1,3-dihydro-isoindol-2-yl)-piperidine-2,6-dione methanesulfonate (0.37 g, 1.00 mmol) and 1-isocyanato-3-phenoxy-benzene (0.212 g, 1.00 mmol) in acetonitrile (10 mL) under nitrogen at RT. After 3 hrs, 1N HCl (10 mL) was added, and the mixture was stirred for 10 min. The solids were isolated by filtration, and washed with water (20 mL) and acetonitrile (10 mL). The crude product was dissolved in a minimal amount of DMF and the product was precipitated by slow addition of water (~30 mL). The solids were collected by filtration, washed with $Et_2O$, and dried in vacuo for 18 hrs to give the product as a white solid (422 mg, 87%): HPLC: Waters Symmetry $C_{18}$, 5 μm, 3.9×150 mm, 1 ml/min, 240 nm, 35/65, $CH_3CN/0.1\% H_3PO_4$, 3.76 min (99.3%); mp: 224-226° C.; $^1H$ NMR (DMSO-$d_6$) δ 1.99 (s, 4H, CH, $CH_3$), 2.29-2.46 (m, 1H, CH), 2.55-2.66 (m, 1H, CH), 2.80-3.01 (m, 1H, CH), 4.18-4.56 (m, 4H, $CH_2$, $CH_2$), 5.10 (dd, J=4.9, 13.2 Hz, 1H, CH), 6.71 (t, J=5.9 Hz, 1H, NH), 7.23-7.36 (m, 1H, Ar), 7.36-7.48 (m, 2H, Ar), 7.51 (s, 1H, Ar), 7.69 (d, J=7.7 Hz, 1H, Ar), 8.55 (s, 1H, NH), 9.75 (s, 1H, NH), 10.67-11.27 (m, 1H, NH); $^{13}C$ NMR (DMSO-$d_6$) δ 22.49, 23.82, 31.18, 42.77, 47.12, 51.56, 118.12, 119.57, 121.85, 122.91, 126.88, 130.26, 133.18, 135.70, 142.36, 144.94, 155.29, 167.67, 167.95, 170.98, 172.85; LCMS: $MH^+$=485; Anal. Calcd. for $C_{27}H_{31}N_1O_5$: C, 66.93; H, 4.99; N, 11.56. Found: C, 67.03; H, 4.72; N, 11.41.

5.12 1-((2-(2,6-Dioxoniperidin-3-yl)-1-oxoisoindolin-5-yl)methyl)-3-(4-nitrophenyl)urea

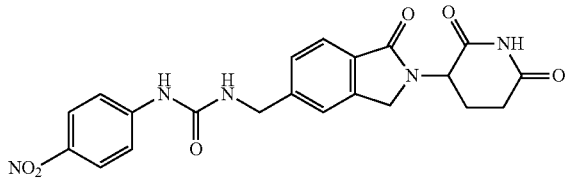

TEA (0.20 g, 2.0 mmol) was added to a stirred mixture of 3-(5-aminomethyl-1-oxo-1,3-dihydro-isoindol-2-yl)-piperidine-2,6-dione methanesulfonate (0.37 g, 1.0 mmol) and 1-isocyanato-4-nitrobenzene (164 mg, 1.0 mmol) in acetonitrile (10 mL) under nitrogen. The mixture stirred at RT for 3 hrs, during which time it remained as a suspension. A 1N HCl solution (10 mL) was added, and the mixture was stirred for 10 min. The solid was isolated by filtration and washed with additional water (20 mL) and acetonitrile (10 mL). The solid was dissolved in minimal amount of DMF and the product was precipitated by slow addition of water (~30 mL). The solid was collected by filtration and washed with $Et_2O$ to remove most of the residual yellow color. The remaining solid was dried in a vacuum oven overnight to provide the product as an off-white solid (330 mg, 75%): HPLC: Waters Symmetry $C_{18}$, 5 μm, 3.9×150 mm, 1 ml/min, 240 nm, 30/70, $CH_3CN/0.1\% H_3PO_4$, 6.15 min (97.1%); mp: 272-274° C.; $^1H$ NMR (DMSO-$d_6$) δ 1.84-2.13 (m, 1H, CHH), 2.24-2.44 (m, 1H, CHH), 2.55-2.66 (m, 1H, CHH), 2.77-3.02 (m, 1H, CHH), 4.16-4.55 (m, 4H, $CH_2$, $CH_2$), 5.11 (dd, J=4.7, 13.0 Hz, 1H, CH), 7.07 (t, J=5.6 Hz, 1H, NH), 7.37-7.83 (m, 5H, Ar), 8.15 (d, J=8.9 Hz, 2H, Ar), 9.48 (s, 1H, NH), 10.98 (s, 1H, NH); $^{13}C$ NMR (DMSO-$d_6$) δ 22.48, 31.17, 42.83, 47.11, 51.57, 116.97, 121.94, 122.96, 125.09, 126.93, 130.38, 140.48, 142.41, 144.26, 147.04, 154.51, 167.91, 170.98, 172.85; LCMS: $MH^+$=438; Anal. Calcd. for $C_{21}H_{19}N_5O_6$+0.5 $H_2O$: C, 56.50; H, 4.52; N, 15.69; Found: C, 56.45; H, 4.31; N, 15.71.

5.13 N-(4-{3-[2-(2,6-Dioxo-piperidin-3-yl)-1-oxo-2,3-dihydro-1H-isoindol-5-ylmethyl]-ureido}-phenyl)-acetamide

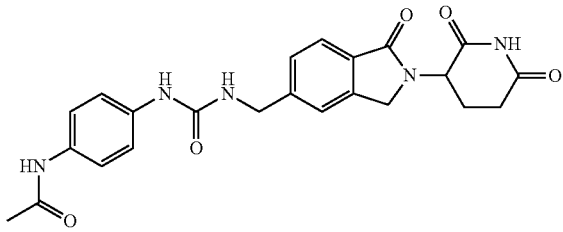

Step 1: Preparation of 1-(4-amino-phenyl)-3-[2-(2,6-dioxo-piperidin-3-yl)-1-oxo-2,3-dihydro-1H-isoindol-5-ylmethyl]-urea. To a stirred mixture of 1-((2-(2,6-dioxopiperidin-3-yl)-1-oxoisoindolin-5-yl)methyl)-3-(4-nitrophenyl)urea (150 mg, 0.343 mmol) in EtOH (2 mL) was added sodium dithionite (597 mg, 3.43 mmol) in water (2 mL). The resulting mixture was heated to 60° C. for 20 min at which time LC-MS indicated complete disappearance of nitro starting material. The reaction mixture was combined with the crude product from a separate run and concentrated in vacuo. The residue was dissolved in minimal DMF and chromatographed on a C-18 preparative HPLC column equipped with mass triggered collection. The desired fractions were combined and concentrated in vacuo to provide 1-(4-amino-phenyl)-3-[2-(2,6-dioxo-piperidin-3-yl)-1-oxo-2,3-dihydro-1H-isoindol-5-ylmethyl]-urea as a pale yellow solid (90 mg, 40% combined average yield from two separate runs): mp: >400° C.; LCMS: MH$^+$=408.

Step 2: Preparation of N-(4-{3-[2-(2,6-dioxo-piperidin-3-yl)-1-oxo-2,3-dihydro-1H-isoindol-5-ylmethyl]-ureido}-phenyl)-acetamide. 1-(4-Amino-phenyl)-3-[2-(2,6-dioxo-piperidin-3-yl)-1-oxo-2,3-dihydro-1H-isoindol-5-ylmethyl]-urea (64 mg, 0.157 mmol) was stirred at room temperature in acetic anhydride (5 mL) for 2 hrs. The volatiles were removed in vacuo and the residue was dissolved in minimal DMF and purified on a C-18 preparative HPLC column. The desired fractions were combined and concentrated in vacuo to provide the product as a pale yellow solid (37 mg, 52% yield): HPLC: Waters Symmetry $C_{18}$, 5 μm, 3.9×150 mm, 1 ml/min, 240 nm, 17/83, $CH_3CN/0.1\%$ $H_3PO_4$, 5.19 min (97.4%); mp: 265-267° C.; $^1$H NMR (DMSO-$d_6$) δ 1.99 (s, 4H, CH, $CH_3$), 2.29-2.46 (m, 1H, CH), 2.55-2.66 (m, 1H, CH), 2.80-3.01 (m, 1H, CH), 4.18-4.56 (m, 4H, $CH_2$, $CH_2$), 5.10 (dd, J=4.9, 13.2 Hz, 1H, CH), 6.71 (t, J=5.9 Hz, 1H, NH), 7.23-7.36 (m, 1H, Ar), 7.36-7.48 (m, 2H, Ar), 7.51 (s, 1H, Ar), 7.69 (d, J=7.7 Hz, 1H, Ar), 8.55 (s, 1H, NH), 9.75 (s, 1H, NH), 10.67-11.27 (m, 1H, NH); $^{13}$C NMR (DMSO-$d_6$) δ 22.49, 23.82, 31.18, 42.77, 47.12, 51.56, 118.12, 119.57, 121.85, 122.91, 126.88, 130.26, 133.18, 135.70, 142.36, 144.94, 155.29, 167.67, 167.95, 170.98, 172.85; LCMS: MH$^+$=450; Anal. Calcd. for $C_{23}H_{23}N_5O_5$+1.0 $H_2O$: C, 59.09; H, 5.39; N, 14.98; Found: C, 58.75; H, 4.99; N, 14.59.

5.14 3-[2-(2,6-Dioxo-piperidin-3-yl)-1-oxo-2,3-dihydro-1H-isoindol-5-ylmethyl]-1-methyl-1-phenyl-urea

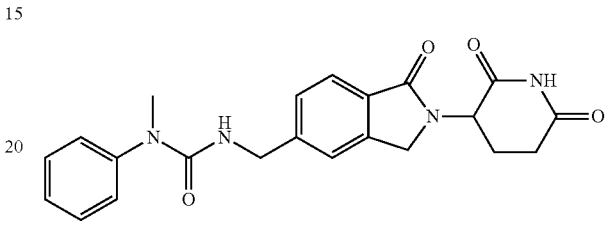

To a suspension of 3-(5-aminomethyl-1-oxo-1,3-dihydro-isoindol-2-yl)-piperidine-2,6-dione methanesulfonic acid salt (0.18 g, 0.5 mmol) in $CH_3CN$ (10 mL) was added DIPEA (0.4 mL, 2.5 mmol) and N-methylphenyl carbamic chloride (178 mg, 1.05 mmol). The mixture was stirred at RT overnight. The suspension was filtered and the solid was washed with water (20 mL), ethyl acetate (20 mL), and $CH_3CN$ (20 mL) to give the product as a white solid (200 mg, 47% yield): HPLC: Waters Symmetry $C_{18}$, 5 μm, 3.9×150 mm, 1 mL/min, 240 nm, 30/70 $CH_3CN/0.1\%$ $H_3PO_4$, 3.56 min (96%); mp: 168-170° C.; $^1$H NMR (DMSO-$d_6$) δ 1.89-2.07 (m, 1H, CHH), 2.30-2.47 (m, 1H, CHH), 2.55-2.69 (m, 1H, CHH), 2.79-3.01 (m, 1H, CHH), 3.18 (s, 3H, $CH_3$), 4.22-4.58 (m, 4H, $CH_2$, $CH_2$), 5.11 (dd, J=5.0. 13.3 Hz, 1H, NCH), 6.68 (t, J=5.9 Hz, 1H, NH), 7.16-7.35 (m, 3H, Ar), 7.36-7.44 (m, 3H, Ar), 7.46 (s, 1H, Ar), 7.66 (d, J=7.7 Hz, 1H, Ar), 10.98 (s, 1H, NH); $^-$C NMR (DMSO-$d_6$) δ 22.51, 31.21, 37.14, 43.76, 47.10, 51.55, 121.85, 122.71, 125.78, 126.54, 126.86, 129.23, 130.04, 142.19, 144.02, 145.41, 156.74, 168.02, 171.02, 172.86; LCMS MH$^+$=407; Anal. Calcd. for $C_{22}H_{22}N_4O_4$+0.5 $H_2O$: C, 63.60; H, 5.58; N, 13.49; S, 6.55; Found: C, 63.61; H, 5.51; N, 13.48.

5.15 1-Biphenyl-4-yl-3-[2-(2,6-dioxo-piperidin-3-yl)-1-oxo-2,3-dihydro-1H-isoindol-5-ylmethyl]-urea

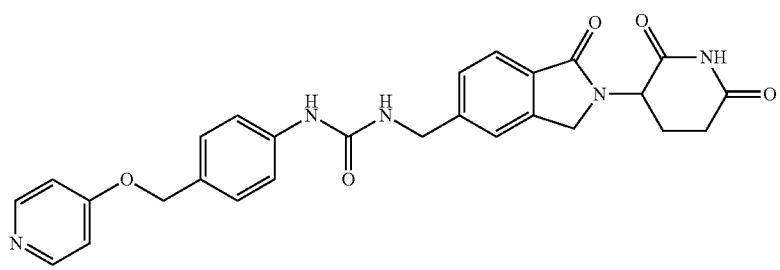

To a suspension of 3-(5-aminomethyl-1-oxo-1,3-dihydro-isoindol-2-yl)-piperidine-2,6-dione methanesulfonic acid salt (0.37 g, 1 mmol) in DMF (2 mL) was added CDI (162 mg, 1 mmol). The mixture was stirred at RT overnight. 4-Phenylaniline (169 mg, 1 mmol) was added to the mixture and the mixture was stirred at RT for 4 hrs. Then the temperature was elevated to 40° C. and the mixture was stirred at this temperature for 8 hrs. The mixture was cooled to RT. The suspension was filtered and the filtrate was added $CH_3CN$ (5 mL) and the resulted suspension was filtered. The collected solid was recrystalized from DMF to give the product as a white solid (30 mg, 15% yield): HPLC: Waters Symmetry $C_{18}$, 5 μm, 3.9×150 mm, 1 mL/min, 240 nm, 50/50 $CH_3CN$/0.1% $H_3PO_4$, 2.78 min (95%); $^1H$ NMR (DMSO-$d_6$) δ 2.02 (br. s., 1H, CHH), 2.28-2.47 (m, 1H, CHH), 2.60 (d, J=18.5 Hz, 1H, CHH), 2.82-3.04 (m, 1H, CHH), 4.23-4.59 (m, 4H, $CH_2$, $CH_2$), 5.11 (dd, J=4.9, 13.2 Hz, 1H, NCH), 6.73-6.83 (m, 1H, NH), 7.22-7.35 (m, 1H, Ar), 7.37-7.66 (m, 10H, Ar), 7.70 (d, J=7.9 Hz, 1H, Ar), 8.75 (s, 1H, NH), 10.98 (s, 1H, NH); $^{13}C$ NMR (DMSO-$d_6$) δ 22.51, 31.20, 42.80, 47.13, 51.58, 118.09, 121.89, 122.94, 125.99, 126.64, 126.85, 128.82, 130.30, 132.86, 139.93, 142.40, 144.81, 155.18, 167.95, 170.99, 172.85; LCMS $MH^+$=423.

5.16 1-[2-(2,6-Dioxo-piperidin-3-yl)-1-oxo-2,3-dihydro-1H-isoindol-5-ylmethyl]-3-[3-(3-methyl-[1,2,4]oxadiazol-5-yl)-phenyl]-urea

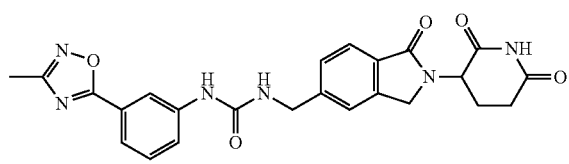

To a stirred suspension of 3-(3-methyl-[1,2,4]oxadiazol-5-yl)-phenylamine (0.22 g, 1.09 mmol) and 3-(5-aminomethyl-1-oxo-1,3-dihydro-isoindol-2-yl)-piperidine-2,6-dione methanesulfonic acid salt (0.40 g, 1.09 mmol) in acetonitrile (5 mL) at RT was added TEA (0.31 mL, 2.19 mmol). The mixture was stirred for 3 hrs. followed by addition of 1N HCl (10 mL), which was stirred for 10 min. The mixture was purified by preparative HPLC to give the product as a white solid (0.10 g, 19% yield): HPLC, Waters Symmetry $C_{18}$, 5 μm, 3.9×150 mm, 1 ml/min, 240 nm, 30/70 $CH_3CN$/0.1% $H_3PO_4$, 4.37 min (99.3%): mp. 242-244° C.; $^1H$ NMR (DMSO-$d_6$) δ 1.92-2.07 (m, 1H, CHH), 2.30-2.46 (m, 4H, $CH_3$, CHH), 2.55-2.67 (m, 1H, CHH), 2.82-3.02 (m, 1H, CHH), 4.24-4.56 (m, 4H, $CH_2$, $CH_2$), 5.11 (dd, J=5.1, 13.2 Hz, 1H, NCH), 6.91 (t, J=5.8 Hz, 1H, NH). 7.39-7.80 (m, 6H, ArH), 8.37 (s, 1H, ArH), 9.05 (s, 1H, NH), 10.98 (s, 1H, NH); $^{13}C$ NMR (DMSO-$d_6$) δ 11.25, 22.49, 31.20, 42.83, 47.12, 51.58, 116.37, 120.24, 121.93, 121.96, 122.94, 123.77, 126.94, 129.90, 130.33, 141.41, 142.39, 144.68, 155.10, 167.61, 167.93, 170.99, 172.85, 174.86. LC/MS MH=475: Anal. Calcd. For $C_{24}H_{22}N_6O_5$+0.4 $H_2O$: C, 59.85; H, 4.77; N, 17.45; Found: C, 59.53; H, 4.68; N, 17.30.

5.17 1-(3-Aminophenyl)-3-((2-(2,6-dioxopiperidin-3-yl)-1-oxoisoindolin-5-yl)methyl)urea

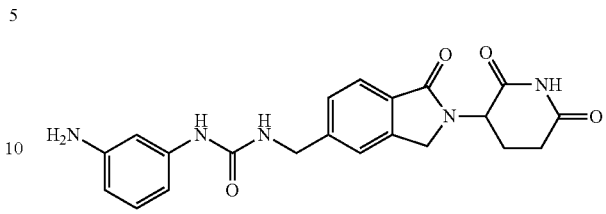

Step 1: To a stirred mixture of 3-(5-aminomethyl-1,3-dihydro-isoindol-2-yl)-piperidine-2,6-dione hydrochloride (0.74 g, 2.00 mmol) and 3-nitropheny isocyanate (0.33 g, 2.00 mmol) in acetonitrile (20 mL) was added TEA (0.56 mL, 4.00 mmol) at RT under nitrogen. After 12 hrs, the solid was filtered and purified by preparative HPLC (gradient: $CH_3CN$/$H_2O$: 15/85 for 5 min, to 100/0 in 10 min, 100/0 for 5 min). After evaporation of the solvent, the residue was triturated in ether (20 mL) for 1 hr. The product was then isolated by filtration and dried in vacuo to give 1-((2-(2,6-dioxopiperidin-3-yl)-1-oxoisoindolin-5-yl)methyl)-3-(3-nitrophenyl)urea as a yellow solid (0.34 g, 39% yield).

Step 2: To a solution of 1-((2-(2,6-dioxopiperidin-3-yl)-1-oxoisoindolin-5-yl)methyl)-3-(3-nitrophenyl)urea (0.33 g, 0.80 mmol) in DMF (80 mL) was added Pd-C (0.10 g, <10% weight). The reaction mixture was hydrogenated with a Parr-shaker at 55 psi. After 12 hrs, the mixture was filtered through a celite pad, which was washed with additional DMF (50 mL). The filtrate was then evaporated and the residue was stirred in water (150 mL) for 3 hrs. The solid was filtered, washed with additional water (50 mL), and dried. The crude product was dissolved in DMF (50 mL), decolorizing carbon was added, and the reaction mixture was stirred for 12 hrs. The mixture was then filtered through a celite pad, which was washed with additional DMF (50 mL). The filtrate was then evaporated and the residue was stirred in water (100 mL) for 3 hrs. The solid was filtered, washed with additional water (50 mL) and dried in vacuo to give the product as a pale yellow solid (0.24 g, 77% yield): HPLC: X-Terra RP 18, 3.9×150 mm, 5 μm, 1 mL/min, 240 nm: $CH_3CN$/0.1% ($HCO_2$)$NH_4$: 15/85: 7.95 min (95.27%); mp: 233-235° C.; $^1H$ NMR (DMSO-$d_6$) δ 1.78-2.08 (m, 1H, CHH), 2.38 (qd, J=4.5, 13.2 Hz, 1H, CHH), 2.59 (d, J=17.8 Hz, 1H, CHH), 2.79-3.06 (m, 1H, CHH), 4.18-4.36 (,. 1H, CHH), 4.36-4.60 (m, 3H, CHH, $CH_2$), 4.91-5.36 (m, 3H, $NH_2$, CH), 6.15 (ddd, J=0.9, 2.1, 7.9 Hz, 1H, Ar), 6.48-6.58 (m, 1H, Ar), 6.63 (t, J=6.0 Hz, 1H, NH), 6.76 (t, J=2.0 Hz, 1H. Ar), 6.85 (t, J=7.9 Hz, 1H, Ar), 7.44 (d, J=7.7 Hz, 1H, Ar), 7.51 (s, 1H, Ar), 7.69 (d, J=7.9 Hz, 1H, Ar), 8.32 (s, 1H, NH), 10.98 (s, 1H, NH); $^{13}C$ NMR (DMSO-$d_6$) δ 22.51, 31.20, 42.73, 47.12, 51.58, 103.78, 106.20, 107.79, 121.86, 122.91, 126.89, 128.89, 130.26, 140.92, 142.38, 144.99, 148.44, 155.16, 167.95, 170.99, 172.85; LCMS: $MH^+$=408; Anal. Calcd. for $C_{21}H_{21}N_5O_4$: C, 61.91, H, 5.20, N, 17.19; Found: C, 62.40, H, 5.67, N, 15.59.

5.18 1-[2-(2,6-Dioxo-piperidin-3-yl)-1-oxo-2,3-dihydro-1H-isoindol-5-ylmethyl]-3-[3-(pyridin-2-yloxy)-phenyl]-urea

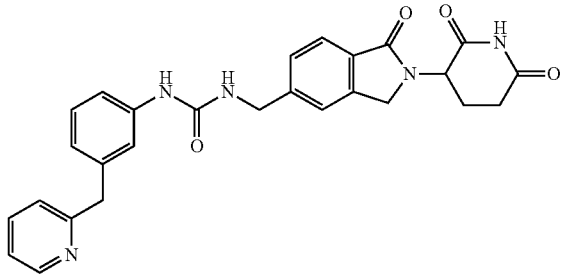

3-(5-aminomethyl-1-oxo-1,3-dihydro-isoindol-2-yl)-piperidine-2,6-dione methanesulfonate (1.11 g, 3.0 mmol) and 1,1'-Carbonyldiimidazole (535 mg, 3.3 mmol) were suspended in dry DMF (20 mL) and the mixture was stirred at rt for 24 h. While stirring, a portion of the reaction mixture (6.7 mL, ~1 mmol) was transferred to a vial containing 3-(Pyridin-2-yloxy)-phenylamine (205 mg, 1.1 mmol). The resulting mixture was stirred at rt overnight and the reaction progress was monitored by LCMS. After 48 h, additional 3-(Pyridin-2-yloxy)-phenylamine (37 mg, 0.2 mmol) was transferred to the reaction mixture and stirring continued for another 24 h. The reaction mixture was acidified with acidic acid and water. The volatiles were removed in vacuo and the residue was dissolved in DMF and purified using C-18 preparatory HPLC to give 1-[2-(2,6-dioxo-piperidin-3-yl)-1-oxo-2,3-dihydro-1H-isoindol-5-ylmethyl]-3-[3-(pyridin-2-yloxy)-phenyl]-urea as a white solid (310 mg, 64% yield): HPLC: Waters Symmetry $C_{18}$, 5 μm, 3.9×150 mm, 1 ml/min, 240 nm, 30/70 $CH_3CN/0.1\%$ $H_3PO_4$, 4.81 min (98.6%); mp: 298-300° C.; $^1H$ NMR (DMSO-$d_6$) δ 1.84-2.06 (m, 1H, CHH), 2.19-2.44 (m, 1H, CHH), 2.54-2.68 (m, 1H, CHH), 2.79-3.05 (m, 1H, CHH), 4.08-4.60 (m, 4H, $CH_2$, $CH_2$), 5.10 (dd, J=5.1, 13.2 Hz, 1H, CH), 6.64 (dd, J=1.4. 8.0 Hz, 1H, Ar), 6.81 (t, J=5.9 Hz, 1H, NH), 6.99 (d, J=8.3 Hz, 1H, Ar), 7.07-7.18 (m, 2H, Ar), 7.24 (t, J=8.1 Hz, 1H, Ar), 7.33 (t, J=2.1 Hz, 1H, Ar), 7.43 (d, J=7.7 Hz, 1H, Ar), 7.50 (s, 1H, Ar), 7.68 (d, J=7.7 Hz, 1H, Ar), 7.78-7.97 (m, 1H, Ar), 8.16 (dd, J=1.5, 4.9 Hz, 1H, Ar), 8.82 (s, 1H, NH), 10.97 (s, 1H, NH); $^{13}C$ NMR (DMSO-$d_6$) δ 22.49, 31.18, 42.73, 47.12, 51.56, 110.23, 111.51, 113.54, 113.68, 118.99, 121.85, 122.93, 126.86, 129.56, 130.29, 140.10, 141.79, 142.39, 144.77, 147.52, 154.37, 155.09, 163.03, 167.93, 170.99, 172.85; LCMS: MH=486; Anal Calcd for $C_{26}H_{23}N_5O_5$+0.3 $H_2O$: C, 63.61; H, 4.85; N, 14.27. Found: C, 63.62; H, 4.62; N, 14.18.

5.19 1-((2-(2,6-dioxopiperidin-3-yl)-1-oxoisoindolin-5-yl)methyl)-3-(3-(piperidin-4-yloxy)phenyl)urea

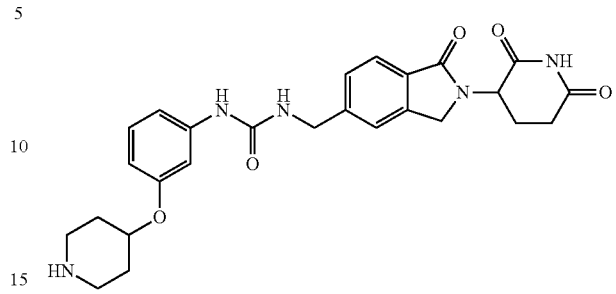

Using the procedure as described in Section 5.15, the product is prepared from 3-(piperidin-4-yloxy)aniline and 3-(5-aminomethyl-1-oxo-1,3-dihydro-isoindol-2-yl)-piperidine-2,6-dione methanesulfonic acid salt.

5.20 1-((2-(2,6-dioxopiperidin-3-yl)-1-oxoisoindolin-5-yl)methyl)-3-(3-hydroxy-4-methylphenyl)urea

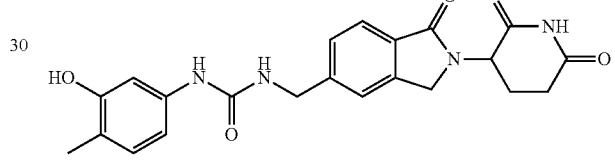

Step 1: Using the procedure as described in Section 5.15, 1-(3-(tert-butyldimethylsilyloxy)-4-methylphenyl)-3-((2-(2,6-dioxopiperidin-3-yl)-1-oxoisoindolin-5-yl)methyl)urea is prepared from 3-(tert-butyldimethylsilyloxy)-4-methylaniline and 3-(5-aminomethyl-1-oxo-1,3-dihydro-isoindol-2-yl)-piperidine-2,6-dione methanesulfonic acid salt.

Step 2: A mixture of 1-(3-(tert-butyldimethylsilyloxy)-4-methylphenyl)-3-((2-(2,6-dioxopiperidin-3-yl)-1-oxoisoindolin-5-yl)methyl)urea (0.54 g, 1.0 mmol) and cesium fluoride (0.15 g, 1.0 mmol) in DMF (10 mL) is heated to 70° C. for 8 hrs. The mixture is cooled and diluted with water (10 mL). The solid precipitate is filtered, rinsed with water (10 mL), and dried under vacuum to provide the product.

5.21 5-(3-((2-(2,6-Dioxopiperidin-3-yl)-1-oxoisoindolin-5-yl)methyl)ureido)-2-methylphenyl 2-aminoacetate Hydrochloride

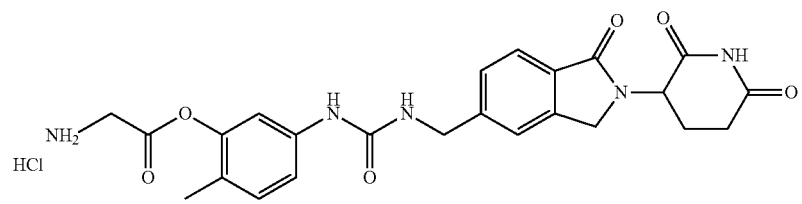

Step 1: Using the procedure as described in Section 5.15, 5-(3-((2-(2,6-dioxopiperidin-3-yl)-1-oxoisoindolin-5-yl)methyl)ureido)-2-methylphenyl 2-(tert-butoxycarbonylamino)acetate is prepared from 5-amino-2-methylphenyl 2-(tert-butoxycarbonylamino)acetate and 3-(5-aminomethyl-1-oxo-1,3-dihydro-isoindol-2-yl)-piperidine-2,6-dione methanesulfonic acid salt.

Step 2: To a mixture of 5-(3-((2-(2,6-dioxopiperidin-3-yl)-1-oxoisoindolin-5-yl)methyl)ureido)-2-methylphenyl 2-(tert-butoxycarbonylamino)acetate (0.58 g, 1.0 mmol) in DCM (50 mL) is added 2M HCl in ether (1 mL), and the mixture is stirred for 24 hrs. The solid precipitate is filtered, rinsed with DCM (10 mL), and dried under vacuum to provide the product.

5.22 5-(3-((2-(2,6-Dioxopiperidin-3-yl)-1-oxoisoindolin-5-yl)methyl)ureido)-2-methylphenyl 2-(piperazin-1-yl)acetate Hydrochloride

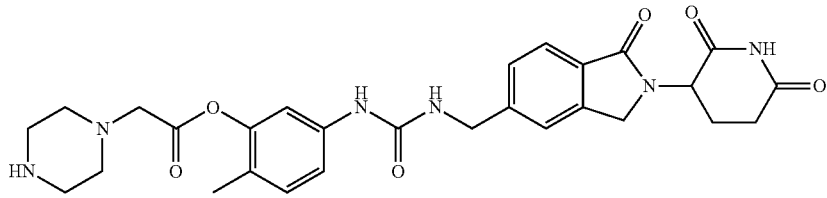

Step 1: Using the procedure as described in Section 5.15, tert-butyl 4-(2-(5-(3-((2-(2,6-dioxopiperidin-3-yl)-1-oxoisoindolin-5-yl)methyl)ureido)-2-methylphenoxy)-2-oxoethyl)piperazine-1-carboxylate is prepared from tert-butyl 4-(2-(5-amino-2-methylphenoxy)-2-oxoethyl)piperazine-1-carboxylate and 3-(5-aminomethyl-1-oxo-1,3-dihydro-isoindol-2-yl)-piperidine-2,6-dione methanesulfonic acid salt.

Step 2: To a mixture of tert-butyl 4-(2-(5-(3-((2-(2,6-dioxopiperidin-3-yl)-1-oxoisoindolin-5-yl)methyl)ureido)-2-methylphenoxy)-2-oxoethyl)piperazine-1-carboxylate (0.65 g, 1.0 mmol) in methylene chloride (50 mL) is added 2M HCl in ether (1 mL), and the mixture will be stirred for 24 hrs. The solid precipitate is filtered, rinsed with DCM (10 mL), and dried under vacuum to provide the product.

5.23 1-(3-(Aminomethyl)-4-methylphenyl)-3-((2-(2,6-dioxopiperidin-3-yl)-1-oxoisoindolin-5-yl)methyl)urea

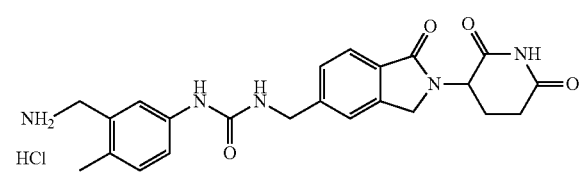

Step 1: Using the procedure as described in Section 5.15, 1-(3-cyano-4-methylphenyl)-3-((2-(2,6-dioxopiperidin-3-yl)-1-oxoisoindolin-5-yl)methyl)urea is prepared from 5-amino-2-methylbenzonitrile and 3-(5-aminomethyl-1-oxo-1,3-dihydro-isoindol-2-yl)-piperidine-2,6-dione methanesulfonic acid salt.

Step 2: A mixture of 1-(3-cyano-4-methylphenyl)-3-((2-(2,6-dioxopiperidin-3-yl)-1-oxoisoindolin-5-yl)methyl)urea (0.54 g, 1.0 mmol), platinum oxide (0.1 g), and 5-6M HCl in isopropanol (2 mL) in acetic acid (15 mL) is hydrogenated under 50 psi hydrogen for 48 hrs. The mixture is filtered through Celite, the filtrate is evaporated under vacuum, and the residue is purified by preparative HPLC to provide the product.

5.24 1-(2-(Aminomethyl)-5-methylphenyl)-3-((2-(2,6-dioxopiperidin-3-yl)-1-oxoisoindolin-5-yl)methyl)urea

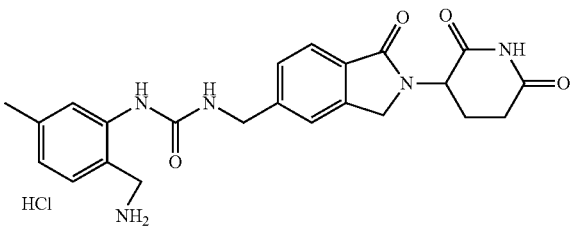

Step 1: Using the procedure as described in Section 5.15, 1-(2-cyano-5-methylphenyl)-3-((2-(2,6-dioxopiperidin-3-yl)-1-oxoisoindolin-5-yl)methyl)urea is prepared from 2-amino-4-methylbenzonitrile and 3-(5-aminomethyl-1-oxo-1,3-dihydro-isoindol-2-yl)-piperidine-2,6-dione methanesulfonic acid salt.

Step 2: A mixture of 1-(2-cyano-5-methylphenyl)-3-((2-(2,6-dioxopiperidin-3-yl)-1-oxoisoindolin-5-yl)methyl)urea (0.54 g, 1.0 mmol), platinum oxide (0.1 g), and 5-6M HCl in isopropanol (2 mL) in acetic acid (15 mL) is hydrogenated under 50 psi hydrogen for 48 hrs. The mixture is filtered through Celite, the filtrate is evaporated under vacuum, and the residue is purified by preparative HPLC to provide the product.

.25 1-((2-(2,6-Dioxopiperidin-3-yl)-1-oxoisoindolin-5-yl)methyl)-3-(4-(morpholinomethyl)phenyl)urea

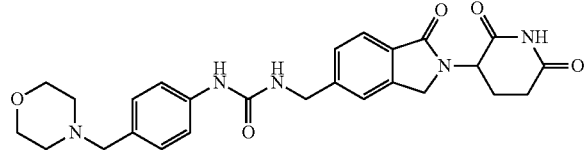

Using the procedure as described in Section 5.15, the product is prepared from 4-(morpholinomethyl)aniline and 3-(5-aminomethyl-1-oxo-1,3-dihydro-isoindol-2-yl)-piperidine-2,6-dione methanesulfonic acid salt.

5.26 1-((2-(2,6-Dioxopiperidin-3-yl)-1-oxoisoindolin-5-yl)methyl)-3-(3-((4-methylpiperazin-1-yl)methyl)phenyl)urea

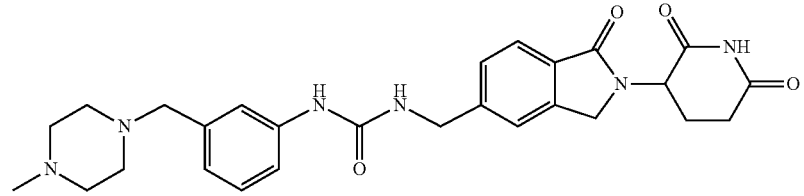

Using the procedure as described in Section 5.15, the product is prepared from 3-((4-methylpiperazin-1-yl)methyl)aniline and 3-(5-aminomethyl-1-oxo-1,3-dihydro-isoindol-2-yl)-piperidine-2,6-dione methanesulfonic acid salt.

5.27 Isoindolin Compounds

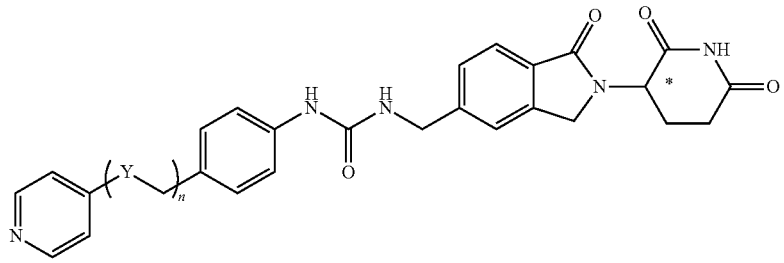

The isoindolin compounds shown above are made using the procedure as described in Section 5.15.

5.28 1-[2-(2,6-Dioxo-piperidin-3-yl)-1-oxo-2,3-dihydro-1H-isoindol-5-ylmethyl]-3-[4-(2-pyridin-4-yl-ethyl)-phenyl]-urea Hydrochloric Acid Salt

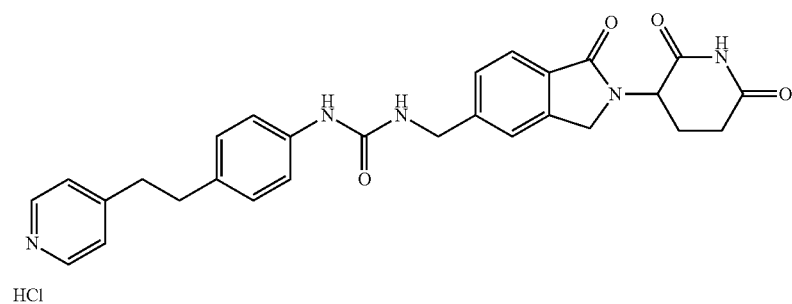

Step 1: Preparation of 4-[2-(4-nitro-phenyl)-vinyl]-pyridine

To a CH₃CN solution of 1-iodo-4-nitrobenzene (498 mg, 2 mmol) and 4-vinylpyridine (262 mg, 2.5 mmol) was added TEA (350 μL, 2.5 mmol) and Pd(OAc)₂ (0.45 mg, 0.2 mmol). The mixture was heated to 100° C. for 48 hr in a capped Pyrex tube. It was then cooled to room temperature, quenched with 1N HCl (20 mL) and concentrated under reduced pressure. The mixture was filtered and the solid was taken up in EtOAc (30 mL) and washed with 1N NaOH (30 mL). The organic layer was concentrated, dried over Na₂SO₄ and concentrated to give 4-[2-(4-nitro-phenyl)-vinyl]-pyridine as yellow solid (160 mg, 37%).

Step 2: Preparation of 4-(2-pyridin-4-yl-ethyl)-phenylamine

To the EtOAc solution (30 mL) of 4-[2-(4-nitro-phenyl)-vinyl]-pyridine (160 mg, 0.71 mmol) was added palladium on carbon (0.1 g, 50% wet). The suspension was hydrogenated at 50 psi of hydrogen for 2 hours. The mixture was filtered over a celite pad. The filtrate was concentrate to give 4-(2-pyridin-4-yl-ethyl)-phenylamine as a yellow solid (140 mg, 100%).

Step 3: Preparation of 1-[2-(2,6-Dioxo-piperidin-3-yl)-1-oxo-2.3-dihydro-1H-isoindol-5-ylmethyl]-3-[4-(2-pyridin-4-yl-ethyl)-phenyl]-urea hydrochloric acid salt To a suspension of 3-(5-aminomethyl-1-oxo-1,3-dihydro-isoindol-2-yl)-piperidine-2,6-dione methanesulfonic acid salt (0.37 g, 1 mmol) in DMF (2 mL) was added carbonyl diimidazole (162 mg, 1 mmol). The mixture was stirred at room temperature overnight. 4-Pyridin-4-ylethyl-phenylamine (140 mg, 0.7 mmol) was added to the mixture and the mixture was stirred at 40° C. overnight then 80° C. for 1.5 hours. The mixture was cooled to room temperature, added water (5 mL) and stirred for 10 min. The suspension was filtered and the filtrate was concentrated and purified on prep-HPLC. The resulted solid after purification was stirred with 1N HCl, filtered and the filtrate was concentrated to give 1-[2-(2,6-dioxo-piperidin-3-yl)-1-oxo-2,3-dihydro-1H-isoindol-5-ylmethyl]-3-[4-(2-pyridin-4-yl-ethyl)-phenyl]-urea hydrochloric acid salt as an off-white solid (30 mg, 8% yield). HPLC: Waters Symmetry $C_{18}$, 5 μm, 3.9×150 mm, 1 mL/min, 240 nm, 5% grad 95% in 5 min, CH₃CN/0.1% H₃PO₄: $t_R$=4.70 min (92%); mp: >400° C.; ¹H NMR (DMSO-d₆) δ 1.89-2.06 (m, 1H, CHH), 2.37 (br. s., 1H, CHH), 2.55-2.67 (m, 1H, CHH), 2.82-3.01 (m, 3H, CH₂, CHH), 3.12 (d, J=7.7 Hz, 2H, CH₂), 4.20-4.53 (m, 5H, CH₂, CH₂), 5.11 (dd, J=4.8, 13.3 Hz, 1H, NCH), 6.89 (br. s., 1H, NH), 7.07 (d, J=8.3 Hz, 2H, Ar), 7.32 (d, J=8.3 Hz, 2H, Ar), 7.44 (d, J=7.9 Hz, 1H, Ar), 7.51 (s, 1H, Ar), 7.69 (d, J=7.7 Hz, 1H, Ar), 7.83 (d, J=5.5 Hz, 2H, Ar), 8.71-8.78 (m, 2H, Ar), 8.80 (s, 1H, NH), 10.98 (s, 1H, NH). ¹³C NMR (DMSO-d₆) δ 22.44, 31.13, 34.25, 36.52, 42.64, 47.05, 51.49, 117.59, 121.78, 122.84, 126.56, 126.78, 128.49, 130.19, 132.39, 138.59, 142.12, 142.28, 144.86, 155.24, 167.86, 170.91, 172.78; LCMS MH=498; Anal Calcd for $C_{28}H_{27}N_5O_4$+1.55 HCl+ 0.75 H₂O+0.15 CH₃CN C, 56.78; H, 5.29; N, 11.64; Cl, 8.87; Found: C, 56.47; H, 5.15; N, 11.99; Cl, 8.85.

5.29 Isoindolin Compounds

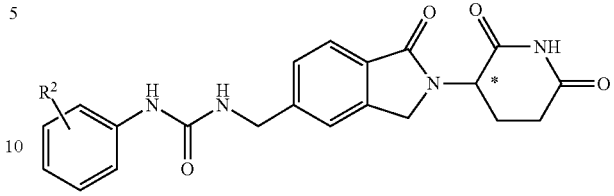

These isoindolin compounds shown above are made using the procedure as described in Section 5.15.

5.30 N"-(3-Chloro-4-methyl-phenyl)-N'-[2-(2,6-dioxo-piperidin-3-yl)-1-oxo-2,3-dihydro-1H-isoindol-5-ylmethyl]-N-cyano-guanidine

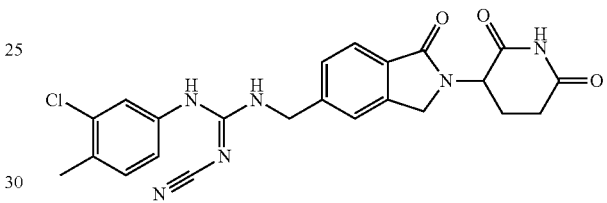

Step 1: Preparation of (3-chloro-4-methyl-phenyl)-carbamic acid phenyl ester.

2-chloro-4-amino toluene (282 mg, 2 mmol) was dissolved in THF (10 mL). The mixture was added sodium hydride (128 mg, 3.2 mmol) and stirred at room temperature for 15 minutes. Dipehnyl N-cyano-carbonimidate (715 mg, 3.0 mmol) was added and the mixture was heated to reflux for 4 hours. The reaction mixture was cooled to room temperature, quenched by saturated NH₄Cl (10 mL), filtered and the solid was dried in oven to give (3-chloro-4-methyl-phenyl)-carbamic acid phenyl ester as solid (0.5 g, 87%).

Step 2: Preparation of N"-(3-Chloro-4-methyl-phenyl)-N'-[2-(2,6-dioxo-piperidin-3-yl)-1-oxo-2,3-dihydro-1H-isoindol-5-ylmethyl]-N-cyano-guanidine To a suspension of 3-(5-aminomethyl-1-oxo-1,3-dihydro-isoindol-2-yl)-piperidine-2,6-dione methanesulfonic acid salt (0.18 g, 0.5 mmol) in DMF (2 mL), was added (3-chloro-4-methyl-phenyl)-carbamic acid phenyl ester (143 mg, 0.5 mmol) and DIPEA (83 μL, 0.5 mmol). The mixture was stirred at 100° C. for 4 hours. The mixture was concentrated under reduced pressure to remove DMF, purified on silica gel column eluted using methanol and methylene chloride to give N"-(3-Chloro-4-methyl-phenyl)-N'-[2-(2,6-dioxo-piperidin-3-yl)-1-oxo-2,3-dihydro-1H-isoindol-5-ylmethyl]-N-cyano-guanidine as a white solid (40 mg, 17% yield). HPLC: Waters Symmetry $C_{18}$, 5 μm, 3.9×150 mm, 1 mL/min, 240 nm, 50/50, CH₃CN/0.1% H₃PO₄,: $t_R$=3.06 min (96.5%); mp: 325-327° C.; ¹H NMR (DMSO-d₆) δ 1.93-2.09 (m, 1H, CHH), 2.25-2.32 (m, 3H, CH₃), 2.33-2.45 (m, 1H, CHH), 2.55-2.67 (m, 1H, CHH), 2.82-3.01 (m, 1H, CHH), 4.27-4.57 (m, 4H, CH₂,CH₂), 5.11 (dd, J=5.1, 13.2 Hz, 1H, NCH), 7.13 (dd, J=2.3, 8.1 Hz, 1H, Ar), 7.32 (d, J=1.5 Hz, 2H, Ar), 7.43 (d, J=7.7 Hz, 1H, Ar), 7.51 (s, 1H, Ar), 7.71 (d, J=7.7 Hz, 1H, Ar), 7.85 (s, 1H, NH), 9.20 (s, 1H, NH), 10.99 (s, 1H, NH). $^{13}$C NMR (DMSO-d$_6$) δ 18.98, 22.49, 31.20, 44.70, 47.15, 51.58, 116.88, 121.98, 122.94, 124.33, 126.97, 130.52, 131.41, 132.08, 133.10, 136.46, 142.36, 142.97, 158.15, 167.86, 170.98, 172.86.; LC-MS: 465; Anal Calcd for C$_{23}$H$_{21}$ClN$_6$O$_3$+0.6 H$_2$O+0.2 EtOAc: C, 57.94; H, 4.86; N, 17.03; Found: C, 57.66; H, 4.81; N, 17.10.

5.31 1-[2-(2,6-Dioxo-piperidin-3-yl)-1-oxo-2,3-dihydro-1H-isoindol-5-ylmethyl]-3-[4-(1H-imidazol-2-yl)-phenyl]-urea

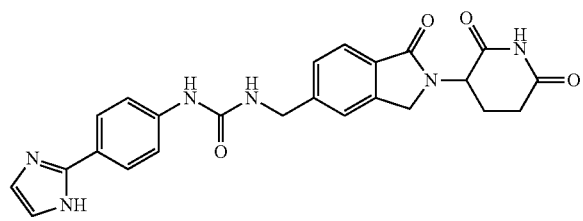

A mixture of 3-(5-aminomethyl-1-oxo-1,3-dihydro-isoindol-2-yl)-piperidine-2,6-dione methanesulfonic acid salt (0.40 g, 1.1 mmol) and CDI (0.19 g, 1.2 mmol) in DMF (5 mL) was stirred at room temperature for 18 hours. To the mixture was added 4-(1H-imidazol-2-yl)-phenylamine (0.17 g, 1.1 mmol) at room temperature, and the mixture was stirred at 60° C. for 1 d. To the mixture was added water (25 mL) and ethyl acetate (20 mL). The mixture was stirred at room temperature for 2 h. The suspension was filtered and the solid was washed with water (20 mL), ethyl acetate (20 mL) and water (20 mL) to give a solid. The solid was purified with Prep HPLC to give 1-[2-(2,6-dioxo-piperidin-3-yl)-1-oxo-2,3-dihydro-1H-isoindol-5-ylmethyl]-3-[4-(1H-imidazol-2-yl)-phenyl]-urea as a white solid (150 mg, 30% yield): HPLC: Waters Symmetry C$_{18}$, 5 μm, 3.9×150 mm, 1 mL/min, 240 nm, 5/95 grad 95/5 in 5 min CH$_3$CN/0.1% H$_3$PO$_4$, 4.41 min (95.9%); mp: 190-192° C.; $^1$H NMR (DMSO-d$_6$) δ 1.91-2.08 (m, 1H, CHH), 2.27-2.47 (m, 1H, CHH), 2.54-2.66 (m, 1H, CHH), 2.81-3.01 (m, 1H, CHH), 4.31 (d, J=17.4 Hz, 1H, CHH), 4.38-4.52 (m, 3H, CHH, CH$_2$), 5.11 (dd, J=5.0, 13.3 Hz, 1H, NCH), 6.78 (t, J=6.0 Hz, 1H, NH), 7.33-7.76 (m, 9H, Ar), 8.17 (s, 1H, HCOOH), 8.67 (s, 1H, NH), 10.99 (s, 1H, NH); $^{13}$C NMR (DMSO-d$_6$) δ 22.41, 31.10, 42.69, 47.02, 51.49, 114.17 (br), 117.80, 121.79, 122.84, 124.55, 126.81, 126.98, 130.19, 135.46, 138.55, 142.31, 144.83, 155.14, 163.19 (HCOOH), 167.88, 170.92, 172.77; LCMS MH=459; Anal. Calcd for C$_{24}$H$_{22}$N$_6$O$_4$+2 H$_2$O+0.7 HCOOH+0.3 DMF: C, 56.04; H, 5.42; N, 16.08; Found: C, 55.84; H, 5.34; N, 16.11.

5.32 1-[3-(1H-Benzoimidazol-2-yl)-4-chloro-phenyl]-3-[2-(2,6-dioxo-piperidin-3-yl)-1-oxo-2,3-dihydro-1H-isoindol-5-ylmethyl]-urea

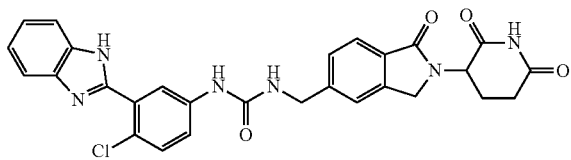

A mixture of 3-(5-aminomethyl-1-oxo-1,3-dihydro-isoindol-2-yl)-piperidine-2,6-dione methanesulfonic acid salt (0.40 g, 1.1 mmol) and CDI (0.21 g, 1.3 mmol) in DMF (5 mL) was stirred at room temperature for 18 h. To the mixture was added 3-(1H-benzoimidazol-2-yl)-4-chloro-phenylamine (0.32 g, 1.3 mmol) at room temperature, and the mixture was stirred at 100° C. for 18 hours. To the mixture was added water (25 mL) and ether (20 mL). The mixture was stirred at room temperature for 2 h. The solvent was decanted. The solid was purified with Prep HPLC to give 1-[3-(1H-benzoimidazol-2-yl)-4-chloro-phenyl]-3-[2-(2,6-dioxo-piperidin-3-yl)-1-oxo-2,3-dihydro-1H-isoindol-5-ylmethyl]-urea as a white solid (130 mg, 22% yield): HPLC: Waters Symmetry C$_{18}$, 5 μm, 3.9×150 mm, 1 mL/min, 240 nm, 20/80 CH$_3$CN/0.1% H$_3$PO$_4$, 4.44 min (99.2%); mp: 275-277° C.; $^1$H NMR (DMSO-d$_6$) δ 1.90-2.10 (m, 1H, CHH), 2.23-2.46 (m, 1H, CHH), 2.54-2.68 (m, 1H, CHH), 2.80-3.02 (m, 1H, CHH), 4.31 (d, J=17.4 Hz, 1H, CHH), 4.37-4.51 (m, 3H, CHH, CH$_2$), 5.11 (dd, J=5.0, 13.3 Hz, 1H, NCH), 6.89 (t, J=5.9 Hz, 1H, NH), 7.23 (d, J=4.5 Hz, 2H, Ar), 7.40-7.76 (m, 7H, Ar), 8.07 (d, J=2.5 Hz, 1H, Ar), 9.02 (s, 1H, NH), 10.98 (s, 1H, NH), 12.64 (br. s., 1H, NH); $^{13}$C NMR (DMSO-d$_6$) δ 22.39, 31.10, 42.75, 47.02, 51.48, 111.62, 118.88, 120.11, 120.62, 121.55, 121.83, 122.56, 122.85, 126.85, 129.79, 130.23, 130.35, 134.56, 139.56, 142.29, 143.00, 144.58, 149.12, 154.96, 162.96, 167.86, 170.91, 172.76; LCMS MH=543, 545; Anal. Calcd for C$_{28}$H$_{23}$N$_6$O$_4$Cl+3 H$_2$O; C, 56.33; H, 4.90; N, 14.08; Found: C, 56.73; H, 4.67; N, 14.09.

5.33 N-(3-Chloro-4-methyl-phenyl)-N'-[2-(2,6-dioxo-piperidin-3-yl)-1-oxo-2,3-dihydro-1H-isoindol-5-ylmethyl]-guanidine Hydrochloride

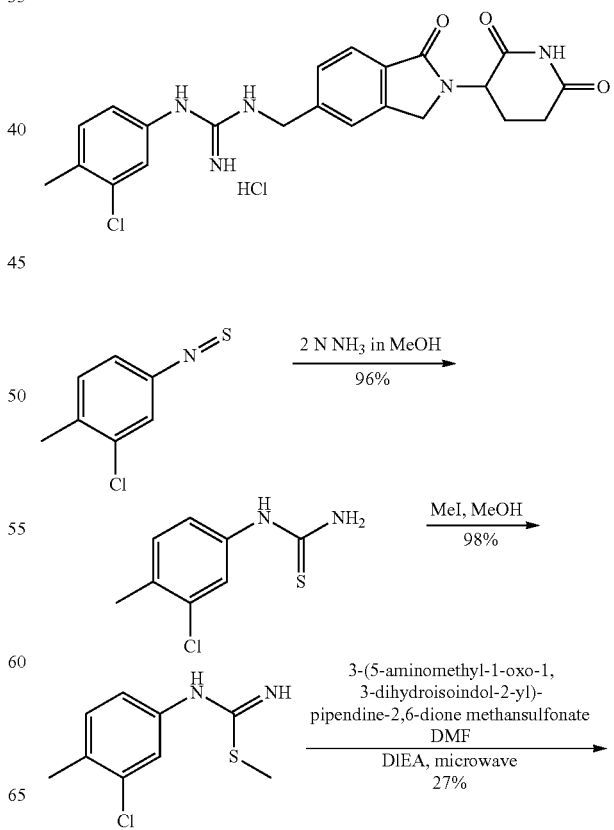

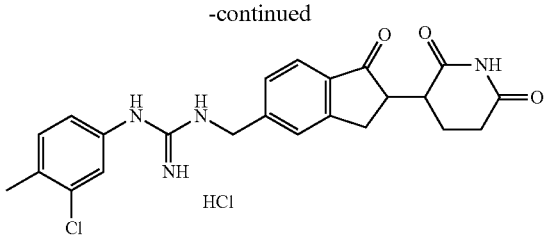

Step 1: 3-Chloro-4-methyl-phenyl)-thiourea

To a solution of 2-chloro-4-isothiocyanato-1-methyl-benzene (2 gm, 10.89 mmol) in dry acetonitrile (10 mL) was added a solution of $NH_3$ in MeOH (2 N, 6 mL) and the mixture was stirred at rt for 2 h. Water was added to the reaction mixture causing the a precipitate to form. The reaction slurry was concentrated in vacuo to ~¼ the volume and the white solid was collected by filtration and dried in a vacuum oven to give 2.1 gm (96% yield) of 3-chloro-4-methyl-phenyl)-thiourea as a white solid that was used without further purification. LCMS: MH=201.

Step 2: 1-(3-Chloro-4-methyl-phenyl)-2-methyl-isothiourea Hydroiodide

To a slurry of 3-chloro-4-methyl-phenyl)-thiourea (2.1 gm, 10.46 mmol) in MeOH (15 mL) was added methyl iodide (2.5 mL, 40 mmol) and the mixture was stirred at rt for 4 h. The reaction mixture was concentrated to dryness and to the residue, a small portion of dichloromethane was added and the volatiles removed in vacuo. This process was repeated twice more to provide a tan foam which was dried in a vacuum oven overnight to give 3.5 gm (98% yield) of crude (2×). 1-(3-chloro-4-methyl-phenyl)-2-methyl-isothiourea hydroiodide. This material was found to be highly hygroscopic and was stored in a desiccator for further use. LCMS: MH=215.

Step 3: N-(3-Chloro-4-methyl-phenyl)-N'-[2-(2,6-dioxo-piperidin-3-yl)-1-oxo-2,3-dihydro-1H-isoindol-5-ylmethyl]-guanidine Hydrochloride In a microwave vial fitted with a stir bar, 1-(3-chloro-4-methyl-phenyl)-2-methyl-isothiourea hydroiodide (597 mg, 1.74 mmol), 3-(5-aminomethyl-1-oxo-1,3-dihydro-isoindol-2-yl)-piperidine-2,6-dione methanesulfonate (560 mg, 1.52 mmol), and DIEA (1.1 mL, 6.06 mmol) were combined in anhydrous DMF (5 mL). The vial was sealed and irradiated in a microwave for 30 min at 120° C. To the reaction mixture was added an additional 100 mg of 3-(5-aminomethyl-1-oxo-1,3-dihydro-isoindol-2-yl)-piperidine-2,6-dione methanesulfonate and the reaction was irradiated for 30 min at 120° C. This process was repeated twice more to consume all of the 1-(3-chloro-4-methyl-phenyl)-2-methyl-isothiourea hydroiodide starting material as it was found co-elute with the desired product on LCMS. The reaction mixture was acidified with acetic acid and the volatiles were evaporated in vacuo. The residue was dissolved in minimal DMF, filtered, and purified using C-18 preparatory HPLC. To the combined fractions containing the desired product, 1 N HCl was added and the solvents removed in vacuo. The obtained white solid was dissolved in minimal water and lyophilized to give 180 mg (27% yield) of N-(3-chloro-4-methyl-phenyl)-N'-[2-(2,6-dioxo-piperidin-3-yl)-1-oxo-2,3-dihydro-1H-isoindol-5-yl-methyl]-guanidine hydrochloride: HPLC: Waters Symmetry $C_{18}$, 5 μm, 3.9×150 mm, 1 ml/min, 240 nm, 20/80 $CH_3CN$/ 0.1% $H_3PO_4$, 3.73 min (97.4%); mp: >400° C.; $^1$H NMR (DMSO-$d_6$) δ 1.91-2.09 (m, 1H, CHH), 2.33 (s, 3H, $CH_3$,), 2.41 (dd, J=4.3, 13.2 Hz, 1H, CHH), 2.54-2.68 (m, 1H, CHH), 2.80-3.05 (m, 1H, CHH), 4.21-4.56 (m, 2H, $CH_2$), 4.66 (d, J=5.7 Hz, 2H, $CH_2$), 5.13 (dd, J=4.9, 13.2 Hz, 1H, CH), 7.14 (dd, J=1.9, 8.1 Hz, 1H, Ar), 7.34 (d, J=1.9 Hz, 1H, Ar), 7.42 (d, J=8.1 Hz, 1H, Ar), 7.51 (d, J=7.9 Hz, 1H, Ar), 7.61 (s, 1H, Ar), 7.76 (d, J=7.7 Hz, 1H, Ar), 7.98 (br. s., 1H, NH), 8.62 (br. s., 1H, NH), 10.16 (s, 1H, NH), 11.00 (s, 1H, NH); $^{13}$C NMR (DMSO-$d_6$) δ 21.04, 24.19, 32.95, 46.33, 49.85, 54.03, 124.13, 125.48, 125.79, 127.28, 129.17, 132.57, 134.20, 135.82, 135.95, 136.64, 143.17, 144.68, 156.84, 170.94, 173.00, 175.82; LCMS: MH=440, 442; Anal Calcd for $C_{22}H_{23}Cl_2N_5O_3$+2.3 $H_2O$+1.9 HCl+0.2 HCOOH: C, 44.72; H, 5.05; N, 11.74; Cl, 23.19; Found: C, 44.55; H, 4.71; N, 11.48; Cl, 22.92.

5.34 1-((2-(2,6-Dioxopiperidin-3-yl)-1-oxoisoindolin-5-yl)methyl)-3-(3-hydroxy-4-methylphenyl)urea

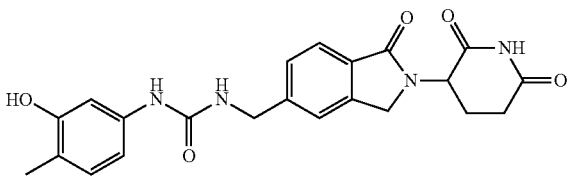

Step 1: A mixture of 2-methyl-5-nitrophenol (3.0 g, 19.6 mmol) TBS-Cl (3.0 g, 19.6 mmol), and TEA (2.2 g, 21.6 mmol) in DMF (30 mL) stirred at ambient temperature for 16 h. The mixture was evaporated under vacuum. The residue was dissolved in ethyl acetate (100 mL) and washed with water (3×100 mL) and evaporated under vacuum. The residue was chromatographed in a hexanes-ethyl acetate gradient, providing 4.7 g of tert-butyldimethyl(2-methyl-5-nitrophenoxy)silane, in 91% yield; $^1$H NMR (DMSO-$d_6$) δ 0.27 (s, 6H), 1.01 (s, 9H), 2.27 (s, 3H), 7.47 (d, J=8.5 Hz, 1H), 7.52 (d, J=2.3 Hz, 1H), 7.78 (dd, J=2.3, 8.3 Hz, 1H).

Step 2: A mixture of the product from Step 1 (4.7 g, 17.6 mmol) and 10% Pd-C (1.0 g, 50% wet) in ethyl acetate was hydrogenated under 50 psi hydrogen for 16 h. The mixture was then filtered through Celite and the filtrate was evaporated under vacuum, providing 3.9 g of -(tert-butyldimethyl-silyloxy)-4-methylaniline, in 94% yield; $^1$H NMR (DMSO-$d_6$) δ 0.17 (s, 6H), 0.97 (s, 9H), 1.96 (s, 3H), 4.81 (s, 2H), 6.00-6.21 (m, 2H), 6.74 (d, J=7.9 Hz, 1H).

Step 3: A mixture of 3-(5-(aminomethyl)-1-oxoisoindolin-2-yl)piperidine-2,6-dione methanesulfonate (0.74 g, 2.0 mmol) and CDI (0.32 g, 2.0 mmol) in DMF (30 mL) was stirred at room temperature for 3 h. and then the product from Step 2 (0.47 g, 2.0 mmol) was added. The mixture was heated to 70° C. for 16 h. Then, the mixture was cooled to room temperature and quenched with 1N HCl (30 mL). The resulting mixture was evaporated under vacuum and the residue was purified by preparative HPLC using an acetonitrile-water gradient, and providing 0.38 g of 1-((2-(2,6-dioxopiperidin-3-yl)-1-oxoisoindolin-5-yl)methyl)-3-(3-hydroxy-4-methylphenyl)urea as a white solid, in 46% yield; HPLC:Waters Symmetry $C_{18}$, 5 μm, 3.9×150 mm, 1 ml/min, 240 nm, 25/75 $CH_3CN$/0.1% $H_3PO_4$, 4.80 min (100.00%); mp 273-275° C.; $^1$H NMR (DMSO-$d_6$) δ 2.02 (s, 4H), 2.27-2.47 (m, 1H), 2.63 (m., 1H), 2.80-3.04 (m, 1H), 4.17-4.59 (m, 4H), 5.11 (dd, J=4.7, 13.0 Hz, 1H), 6.47-6.72 (m, 2H), 6.86 (d, J=7.9 Hz, 1H), 7.04 (s, 1H), 7.44 (d, J=7.7 Hz, 1H), 7.51 (s, 1H), 7.69 (d, J=7.7 Hz, 1H), 8.39 (s, 1H), 9.13 (s, 1H), 10.98 (s, 1H); $^{13}$C NMR (DMSO-$d_6$) δ 15.35, 22.49, 31.20, 42.74, 47.12, 51.58, 104.76, 108.45, 116.48, 121.86, 122.91, 126.91, 130.19, 130.26, 138.92, 142.36, 144.96, 155.18, 155.29, 167.95,

5.35 1-((2-(2,6-Dioxopiperidin-3-yl)-1-oxoisoindolin-5-yl)methyl)-3-(4-hydroxy-3-methylphenyl)urea

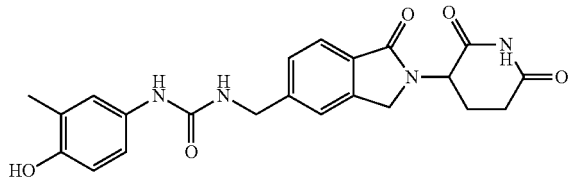

Step 1: A mixture of 2-methyl-4-nitrophenol (3.0 g, 19.6 mmol), TBS-Cl (3.0 g, 19.6 mmol), and TEA (2.2 g, 21.6 mmol) in DMF (30 mL) stirred at ambient temperature for 16 h. The mixture was partitioned between 10% aqueous sodium bicarbonate solution (100 mL) and ethyl acetate (100 mL), and the aqueous layer was extracted with ethyl acetate (100 mL). The combined organic layers were washed with 10% aqueous sodium bicarbonate (3×100 mL) and water (100 mL), and evaporated under vacuum. The residue was chromatographed in hexanes-ethyl acetate gradient, providing 3.9 g of tert-butyldimethyl(2-methyl-4-nitrophenoxy)silane, in 75% yield; $^1$H NMR (DMSO-d$_6$) δ 0.29 (s, 6H), 1.00 (s, 9H), 2.24 (s, 3H), 7.03 (d, J=8.9 Hz, 1H), 8.02 (dd, J=2.8. 8.9 Hz, 1H), 8.12 (d, J=2.5 Hz, 1H).

Step 2: A mixture of the product from step 1 (3.9 g, 14.6 mmol) and 10% Pd-C (0.5 g, 50% wet) in ethyl acetate was hydrogenated under 50 psi hydrogen for 18 h. The mixture was filtered through Celite and the filtrate was evaporated, providing 3.2 g of 4-(tert-butyldimethylsilyloxy)-3-methylaniline, in 93% yield.

Step 3: A mixture of 3-(5-(aminomethyl)-1-oxoisoindolin-2-yl)piperidine-2,6-dione methanesulfonate (0.74 g, 2.0 mmol) and CDI (0.32 g, 2.0 mmol) in DMF (30 mL) was stirred at room temperature for 3 h, and then the product from Step 2 (0.47 g, 2.0 mmol) was added. The mixture was heated to 70° C. for 30 h. Then, the mixture was cooled to room temperature and quenched with 1N HCl (30 mL), resulting in solid precipitate. This solid was purified by chromotagraphy on a silica gel column, using a methylene chloride-methanol gradient, and providing 0.59 g of 1-(4-(tert-butyldimethylsilyloxy)-3-methylphenyl)-3-((2-(2,6-dioxopiperidin-3-yl)-1-oxoisoindolin-5-yl)methyl)urea as an off-white solid, in 55% yield; $^1$H NMR (DMSO-d$_6$) δ 0.16 (s, 6H), 0.97 (s, 9H), 1.88-2.06 (m, 1H), 2.10 (s, 3H), 2.25-2.47 (m, 1H), 2.53-2.70 (m, 1H), 2.80-3.02 (m, 1H), 4.31 (d, J=17.4 Hz, 1H), 4.36-4.52 (m, 3H), 5.11 (dd, J=4.9, 13.2 Hz, 1H), 6.51-6.74 (m, 2H), 7.08 (dd, J=2.5, 8.6 Hz, 1H), 7.18 (d, J=2.3 Hz, 1H), 7.43 (d, J=7.7 Hz, 1H), 7.50 (s, 1H), 7.69 (d, J=7.7 Hz, 1H), 8.35 (s, 1H), 10.98 (s, 1H).

Step 4: To a solution of the product from Step 3 (0.5 g, 0.9 mmol) in methylene chloride (20 mL) was added 2N HCl in ether (2 mL). The mixture stirred for 16 h at ambient temperature. The precipitated product was isolted by filtration, and was rinsed with methylene chloride (20 mL) and dried under vacuum, providing 0.4 g of 1-((2-(2,6-dioxopiperidin-3-yl)-1-oxoisoindolin-5-yl)methyl)-3-(4-hydroxy-3-methylphenyl)urea as an off-white solid, in quantitaive yield; HPLC:Waters Symmetry C$_{18}$, 5 μm, 3.9×150 mm, 1 ml/min, 240 nm, 30/70 CH$_3$CN/0.1% H$_3$PO$_4$, 1.88 min (96.94%); mp 210-212° C.; $^1$H NMR (DMSO-d$_6$) δ 1.94-2.18 (m, 4H), 2.30-2.51 (m, 1H), 2.58-2.72 (m, 1H), 2.87-3.06 (m, 1H), 4.25-4.56 (m, 4H), 5.15 (dd, J=5.0, 13.3 Hz, 1H), 6.67 (d, J=8.5 Hz, 1H), 7.02 (dd, J=2.5, 8.6 Hz, 1H), 7.12 (d, J=2.3 Hz, 1H), 7.47 (d, J=7.7 Hz, 1H), 7.54 (s, 1 H), 7.73 (d, J=7.7 Hz, 1H), 8.32 (br. s., 1H), 11.02 (s, 1H); $^{13}$C NMR (DMSO-d$_6$) δ 16.15, 22.51, 31.20, 42.77, 47.12, 51.56, 114.47, 117.11, 121.32, 121.83, 122.88, 123.61, 126.86, 130.22, 131.72, 142.35, 145.17, 150.10, 155.58, 170.99, 172.85; LCMS MH=423; Anal. Calcd for C$_{22}$H$_{22}$N$_4$O$_5$+0.25 CH$_2$Cl$_2$: C, 60.23; H, 5.11; N, 12.63; Found: C, 60.14; H, 5.43; N, 12.54.

5.36 1-(4-tert-Butyl-cyclohexyl)-3-[2-(2,6-dioxopiperidin-3-yl)-1-oxo-2,3-dihydro-1H-isoindol-5-ylmethyl]-urea

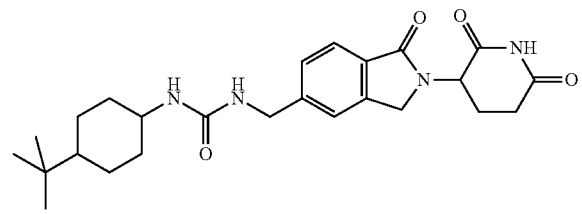

To a stirred suspension of 4-tert-butyl-cyclohexylamine (0.20 g, 1.28 mmol) in DMF (5 mL) at 40° C. was added CDI (0.23 g, 1.40 mmol). The mixture was stirred for 15 min. followed by addition of 3-(5-aminomethyl-1-oxo-1,3-dihydro-isoindol-2-yl)-piperidine-2,6-dione methanesulfonic acid salt (0.47 g, 1.28 mmol). Heating was stopped after 1.5 hrs and the mixture was stirred at RT overnight. Solvent was evaporated and the residue was purified by preparative HPLC to give the product as a white solid (0.076 g, 13% yield):

HPLC, Waters Symmetry C$_{18}$, 5 μm, 3.9×150 mm, 1 ml/min, 240 nm, 35/65 CH$_3$CN/0.1% H$_3$PO$_4$, 13.37 min (44.7%), 14.68 min (54.3%); mp, 182-184° C.; $^1$H NMR (DMSO-d$_6$) δ 0.83 (s, 9H, CH$_3$, CH$_3$, CH$_3$), 0.90-1.21 (m, 4H, CH$_2$, CH$_2$), 1.30-1.58 (m, 2H, CHH, CHH), 1.61-1.78 (m, 2H, CHH, CHH), 1.87 (br. s., 1H, CHH), 1.95-2.06 (m, 1H, CHH), 2.28-2.47 (m, 1H, CHH), 2.63 (br. s., 1H, CHH), 2.83-3.00 (m, 1H, CHH), 3.78 & 3.27 (2s, 1H, CH), 4.23-4.50 (m, 4H, CH$_2$, CH$_2$), 5.11 (dd, J=5.0, 13.1 Hz, 1H, NCH), 5.79-6.12 (m, 1H, NH), 6.25-6.44 (m, 1H, NH), 7.38 (t, J=6.8 Hz, 1H, ArH), 7.45 (d, J=6.2 Hz, 1H, ArH), 7.67 (dd, J=4.1, 7.6 Hz, 1H, ArH), 10.99 (s, 1H, NH); (Note: $^1$H NMR showed about 55% to 45% isomer ratio); $^{13}$C NMR (DMSO-d$_6$) δ 21.33, 22.49, 25.95, 27.38, 27.45, 31.02, 31.20, 32.06, 32.26, 33.76, 42.87, 43.43, 46.81, 47.10, 47.42, 48.69, 51.56, 121.76, 121.88, 122.83, 122.90, 126.81, 126.88, 130.11, 130.19, 142.29, 142.35, 145.36, 145.52, 157.35, 167.98, 170.99, 172.85. LC/MS MH$^+$=455; Anal. Calcd. For C$_{25}$H$_{34}$N$_4$O$_4$+ 0.7 H$_2$O; C, 64.27; H, 7.64; N, 11.99; Found: C, 63.98; H, 7.98; N, 11.92.

5.37 1-[2-(2,6-Dioxo-piperidin-3-yl)-1-oxo-2,3-dihydro-1H-isoindol-5-ylmethyl]-3-(4-methyl-cyclohexyl)-urea

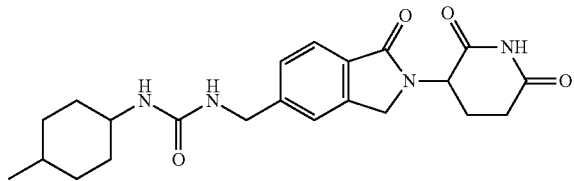

To a stirred suspension of 4-methyl-cyclohexylamine (mixture of cis/trans isomers, 0.21 g, 1.86 mmol) in DMF (10 mL) at 40° C. was added CDI (0.33 g, 2.04 mmol). The mixture was stirred for 15 min, followed by addition of 3-(5-aminomethyl-1-oxo-1,3-dihydro-isoindol-2-yl)-piperidine-2,6-dione methanesulfonic acid salt (0.69 g, 1.86 mmol). Heating was stopped after 1.5 hrs and the mixture was stirred at RT overnight. Solvent was evaporated and the residue was purified by preparative HPLC to give the product as a white solid (0.14 g, 18% yield): HPLC, Waters Symmetry $C_{18}$, 5 μm, 3.9×150 mm, 1 ml/min, 240 nm, 25/75 $CH_3CN/0.1\%$ $H_3PO_4$, 11.33 min (59.1%), 12.41 min (39.7%); mp, 223-225° C.; $^1$H NMR (DMSO-$d_6$) δ 0.81-0.93 (m, 3H, $CH_3$), 0.95-1.35 (m, 3H, CHH, CHH, CHH), 1.37-1.57 (m, 4H, CHH, CHH, CHH, CH), 1.58-1.70 (m, 1H, CHH), 1.73-1.88 (m, 1H, CHH), 1.92-2.07 (m, 1H, CHH), 2.30-2.47 (m, 1H, CHH), 2.54-2.67 (m, 1H, CHH), 2.83-3.00 (m, 1H, CHH), 3.20-3.75 (m, 1H, CH), 4.21-4.51 (m, 4H, $CH_2$, $CH_2$), 5.11 (dd, J=5.0, 13.1 Hz, 1H, NCH), 5.78-6.11 (m, 1H, NH), 6.24-6.40 (m, 1H, NH), 7.34-7.42 (m, 1H, ArH), 7.42-7.50 (m, 1H, ArH), 7.63-7.72 (m, 1H, ArH), 10.98 (s, 1H, NH); (Note: $^1$H NMR showed about 60% to 40% isomer ratio); $^{13}$C NMR (DMSO-$d_6$) δ (21.47, 22.17, 22.49, 29.42, 29.77, 30.42, 31.20, 31.50, 33.28, 33.73, 42.86, 44.54, 47.09, 48.37, 51.56, 121.78, 122.87, 126.81, 130.16, 142.33, 145.44, 145.52, 157.33, 167.98, 170.99, 172.85; LC/MS MH$^+$=413; Anal. Calcd. For $C_{22}H_{28}N_4O_4$+0.4 $H_2O$: C, 63.23; H, 6.90; N, 13.41; Found: C, 62.93; H, 6.92; N, 13.09.

5.38 1-(3-Diethylamino-propyl)-3-[2-(2,6-dioxo-piperidin-3-yl)-1-oxo-2,3-dihydro-1H-isoindol-5-ylmethyl]-urea, Formic Acid Salt

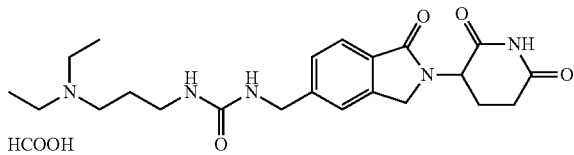

To the solution of para-nitrophenyl chloroformate (202 mg, 1 mmol) in $CH_3CN$ (5 mL) was added dropwise at 0° C. a solution of N,N-diethyl-propane-1,3-diamine (130 mg, 1 mmol) and DIPEA (0.082 mL, 1 mmol) in $CH_3CN$ (5 mL). The mixture was stirred at 0° C. for 10 min. 3-(5-Aminomethyl-1-oxo-1,3-dihydro-isoindol-2-yl)-piperidine-2,6-dione methanesulfonic acid salt (0.37 g, 1 mmol) was added, followed by additional DIPEA (0.082 mL, 1 mmol). The mixture was allowed to warm to RT and stirred overnight at RT. The mixture was added 1N HCl (15 mL) and filtered. The resulted solid was purified on preparative HPLC to give the product as an off-white solid (280 mg, 65% yield): HPLC: Waters Symmetry $C_{18}$, 5 μm, 3.9×150 mm, 1 mL/min, 240 nm, 5% gradient 100% in 5 min, $CH_3CN/0.1\%$ $H_3PO_4$, 4.46 min (97%); mp: 90-92° C.; $^1$H NMR (DMSO-$d_6$) δ 1.01 (t, J=7.1 Hz, 6H, $CH_3$, $CH_3$), 1.58 (quin, J=7.1 Hz, 2H, $CH_2$), 1.94-2.06 (m, 1H, CHH), 2.39 (qd, J=4.5, 13.2 Hz, 1H, CHH), 2.55-2.73 (m, 7H, $CH_2$, $CH_2$, $CH_2$, CHH), 2.83-2.99 (m, 1H, CHH), 3.05 (d, J=5.3 Hz, 2H, $CH_2$), 4.15-4.56 (m, 4H, $CH_2$, $CH_2$), 5.10 (dd, J=5.1, 13.4 Hz, 1H, NCH), 6.17 (br. s., 1H, NH), 6.60 (s, 1H, NH), 7.39 (d, J=7.7 Hz, 1H, Ar), 7.45 (s, 1H, Ar), 7.67 (d, J=7.9 Hz, 1H, Ar), 8.25 (br. s., 1H, HCOOH), 10.98 (br. s., 1H, NH); $^{13}$C NMR (DMSO-$d_6$) δ 10.25, 22.49, 26.14, 31.20, 37.39, 42.93, 46.11, 47.09, 51.56, 121.73, 122.81, 126.76, 130.13, 142.27, 145.54, 158.18, 167.99, 171.01, 172.86; LCMS MH$^+$=430; Anal. Calcd. for $C_{23}H_{33}N_5O_6$+2 $H_2O$: C, 54.00; H, 7.29; N, 13.69; Found: C, 54.04; H, 6.92; N, 13.63.

5.39 1-[2-(2,6-Dioxo-piperidin-3-yl)-1-oxo-2,3-dihydro-1H-isoindol-5-ylmethyl]-3-(4-methyl-tetrahydro-pyran-4-yl)-urea

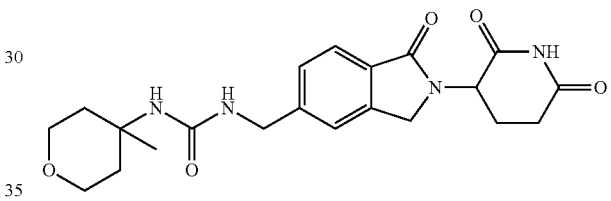

To the solution of para-nitrophenyl chloroformate (202 mg, 1 mmol) in $CH_3CN$ (5 mL) was added dropwise at 0° C. a solution of 4-methyl-tetrahydro-pyran-4-ylamine (150 mg, 1 mmol) and DIPEA (0.082 mL, 1 mmol) in $CH_3CN$ (5 mL). The mixture was stirred at 0° C. for 10 min. 3-(5-Aminomethyl-1-oxo-1,3-dihydro-isoindol-2-yl)-piperidine-2,6-dione methanesulfonic acid salt (0.37 g, 1 mmol) was added, followed by additional DIPEA (0.082 mL, 1 mmol). The mixture was allowed to warm to RT and stirred overnight at RT. The mixture was added 1N HCl (15 mL) and filtered. The resulted solid was purified on preparative HPLC to give a solid. The solid was recrystalized from DMF (1 mL) and water (1 mL) to give the product as a white solid (55 mg, 12% yield): HPLC: Waters Symmetry $C_{18}$, 5 μm, 3.9×150 mm, 1 mL/min, 240 nm, 5% gradient 100% in 5 min. $CH_3CN/0.1\%$ $H_3PO_4$, 5.02 min (98%): mp: 158-160° C.; $^1$H NMR (DMSO-$d_6$) δ 1.29 (s, 3H, $CH_3$), 1.40-1.58 (m, 2H, CHH), 1.84-1.96 (m, 2H, CHH, CHH), 1.99 (s, 1H, CHH), 2.30-2.45 (m, 1H, CHH), 2.55-2.65 (m, 1H, CHH), 2.84-2.99 (m, 1H, CHH), 3.44-3.68 (m, 4H, $CH_2$, $CH_2$), 4.22-4.58 (m, 4H, $CH_2$, $CH_2$), 4.95-5.29 (m, 1H, NCH), 5.85 (s, 1H, NH), 6.08-6.52 (m, 1H, NH), 7.33-7.42 (m, 1H, Ar), 7.45 (s, 1H, Ar), 7.68 (d, J=7.6 Hz, 1H, Ar), 10.98 (s, 1H, NH); $^{13}$C NMR (DMSO-$d_6$) δ 22.48, 27.00, 31.20, 36.93, 42.58, 47.10, 48.85, 51.56, 62.92, 120.99, 121.67, 122.88, 126.69, 142.35, 145.48, 157.22, 167.98, 171.01, 172.86; LCMS MH$^+$=415; Anal. Calcd. for $C_{21}H_{26}N_4O_5$+0.5 $H_2O$: C, 59.56; H, 6.43; N, 13.23; Found: C, 59.34; H, 6.35; N, 13.21.

5.40 1-(1-Benzyl-piperidin-4-yl)-3-[2-(2,6-dioxo-piperidin-3-yl)-1-oxo-2,3-dihydro-1H-isoindol-5-ylmethyl]-urea

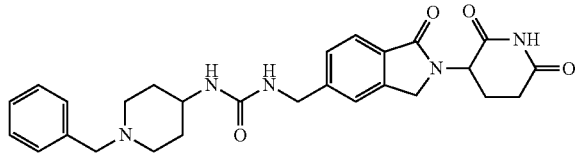

To the solution of para-nitrophenyl chloroformate (202 mg, 1 mmol) in CH$_3$CN (5 mL) was added dropwise at 0° C. a solution of 4-amino-benzyl-piperidine (190 mg, 1 mmol) and DIPEA (0.082 mL, 1 mmol) in CH$_3$CN (5 mL). The mixture was stirred at 0° C. for 10 min. 3-(5-Aminomethyl-1-oxo-1,3-dihydro-isoindol-2-yl)-piperidine-2,6-dione methanesulfonic acid salt (0.37 g, 1 mmol) was added, followed by additional DIPEA (0.082 mL, 1 mmol). The mixture was allowed to warm to RT and stirred overnight at RT. The mixture was added 1N HCl (15 mL) and filtered. The resulted solid was purified on preparative-HPLC to give a gluey solid. The solid was dissolved in DMF (1 mL) and saturated NaHCO$_3$ solution was added dropwise until precipitation started occurring. It was sat still at RT for 30 min and solid was filtered to give the product as a white solid (55 mg, 12% yield): HPLC: Waters Symmetry C$_{18}$, 5 µm, 3.9×150 mm, 1 mL/min, 240 nm, 5% gradient 100% in 5 min, CH$_3$CN/0.1% H$_3$PO$_4$, 4.64 min (99%); mp: 208-210° C.; $^1$H NMR (DMSO-d$_6$) δ 1.21-1.52 (m, 2H, CHH), 1.63-1.82 (m, 2H, CHH), 1.89-2.14 (m, 3H, CHH, CHH, CHH), 2.39 (d, J=13.6 Hz, 1H, CHH), 2.55-2.65 (m, 1H, CHH), 2.64-2.75 (m, 2H, CHH, CHH), 2.83-3.02 (m, 1H, CHH), 3.37-3.41 (m, 1H, CH), 3.43 (s, 2H, CH$_2$), 4.21-4.50 (m, 3H, CH$_2$, CH$_2$), 5.10 (dd, J=5.0, 13.3 Hz, 1H, NCH), 5.94 (d, J=7.9 Hz, 1H, NH), 6.34 (t, J=6.0 Hz, 1H, NH), 7.13-7.48 (m, 6H, Ar), 7.66 (d, J=7.6 Hz, 1H, Ar), 10.97 (s, 1H, NH); $^{13}$C NMR (DMSO-d$_6$) δ 22.49, 31.20, 32.46, 42.86, 46.43, 47.09, 51.55, 51.90, 62.19, 121.78, 122.84, 126.79, 128.10, 128.69, 130.13, 138.64, 142.29, 145.44, 157.32, 167.96, 170.99, 172.85; LCMS MH$^+$=490; Anal. Calcd. for C$_{21}$H$_{26}$N$_4$O$_5$+0.5 H$_2$O: C, 59.56; H, 6.43; N, 13.23; Found: C, 59.34; H, 6.35; N, 13.21.

5.41 1-[2-(2,6-Dioxo-piperidin-3-yl)-1-oxo-2,3-dihydro-1H-isoindol-5-ylmethyl]-3-piperidin-4-yl-urea Hydrochloride Salt

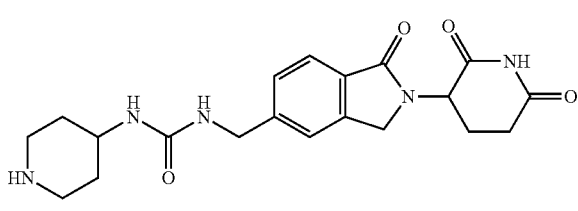

HCl

Step 1. A mixture of 3-(5-aminomethyl-1-oxo-1,3-dihydro-isoindol-2-yl)-piperidine-2,6-dione methanesulfonic acid salt (1.25 g, 3.39 mmol) and CDI (0.61 g, 3.73 mmol) in DMF (10 mL) was stirred at RT overnight. 4-Amino-piperidine-1-carboxylic acid tert-butyl ester (0.68 g, 3.39 mmol) was then added and the mixture was stirred overnight. The mixture was purified by preparative HPLC to give 4-{3-[2-(2,6-dioxo-piperidin-3-yl)-1-oxo-2,3-dihydro-1H-isoindol-5-ylmethyl]-ureido}-piperidine-1-carboxylic acid tert-butyl ester as an off-white solid (0.46 g, 27% yield). The product was used in the next step without further purification. HPLC, Waters Symmetry C$_{18}$, 5 µm, 3.9×150 mm, 1 ml/min, 240 nm, 30/70 CH$_3$CN0.1% H$_3$PO$_4$, 4.35 min (99.4%).

Step 2: A mixture of 4-{3-[2-(2,6-dioxo-piperidin-3-yl)-1-oxo-2,3-dihydro-1H-isoindol-5-ylmethyl]ureido}-piperidine-1-carboxylic acid tert-butyl ester (0.45 g, 0.90 mmol) in 2 M hydrochloride in diethyl ether (30 mL, 9.01 mmol) was stirred overnight. The white suspension was filtered and washed with diethyl ether. The resulting white solid was stirred in acetonitrile (80 mL) at 50° C. overnight. The suspension was filtered, washed with acetonitrile, and vacuum dried to give the product as a white solid (0.34 g, 86% yield): HPLC: Waters Xterra C$_{18}$, 5 µm, 3.9×150 mm, 1 ml/min, 240 nm, 5/95 CH$_3$CN/0.1% HCOONH$_4$ gradient to 95/5 in 5 min, kept 5 min, 3.10 min (95.1%); mp, 340-342° C.; $^1$H NMR (DMSO-d$_6$) δ 1.46-1.65 (m, 2H, CHH, CHH), 1.85-2.05 (m, 3H, CHH, CHH, CHH), 2.30-2.47 (m, 1H, CHH), 2.55-2.67 (m, 1H, CHH), 2.83-3.03 (m, 3H, CHH, CHH, CHH), 3.15-3.27 (m, 2H, CHH, CHH), 3.59-3.77 (m, 1H, CH), 4.23-4.51 (m, 4H, CH$_2$, CH$_2$), 5.11 (dd, J=4.9, 13.2 Hz, 1H, NCH), 6.40-6.57 (m, 2H, NH, NH), 7.39 (d, J=7.9 Hz, 1H, ArH), 7.45 (s, 1H, ArH), 7.67 (d, J=7.7 Hz, 1H, ArH), 8.75 (br. s., 2H, ClH$_2$N), 10.98 (s, 1H, NH); $^{13}$C NMR (DMSO-d$_6$) δ 22.49, 28.92, 31.20, 41.96, 42.82, 43.95, 47.09, 51.55, 121.76, 122.84, 126.76, 130.14, 142.29, 145.35, 157.32, 167.98, 171.01, 172.87; LC/MS MH$^+$=400; Anal. Calcd. For C$_{20}$H$_{26}$N$_5$O$_4$Cl+1.7 H$_2$O: C, 51.49; H, 6.35; N, 15.01; Cl, 7.60; Found: C, 51.18; H, 6.15; N, 14.90; Cl, 7.51.

5.42 Isoindolin Compounds

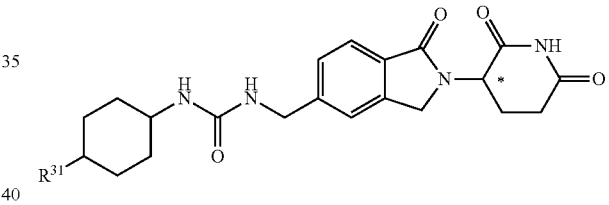

The isoindol in compounds shown above are using the procedure as described in Section 5.15.

5.43 4-{3-[2-(2,6-Dioxo-piperidin-3-yl)-1-oxo-2,3-dihydro-1H-isoindol-5-ylmethyl]-ureido}-cyclohexanecarboxylic Acid Amide

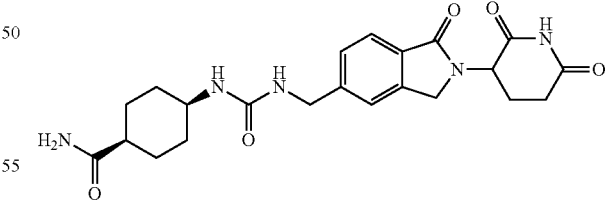

To the solution of para-nitro-phenyl chloroformate (200 mg, 1 mmol) in CH$_3$CN (5 mL), was added the CH$_3$CN solution (5 mL) of 4-Amino-cyclohexanecarboxylic acid amide (210 mg, 1 mmol) and DIPEA (0.3 mL, 2 mmol) dropwise at room temperature. The mixture was stirred at room temperature for 10 min. 3-(5-Aminomethyl-1-oxo-1,3-dihydro-isoindol-2-yl)-piperidine-2,6-dione methanesulfonic acid salt (0.37 g, 1 mmol) was added followed by additional DIPEA (0.15 mL, 1 mmol). The mixture was stirred overnight at ambient temperature. The mixture was then filtered. The filtrate was purified on prep-HPLC to give 4-{3-[2-(2,6-dioxo-piperidin-3-yl)-1-oxo-2,3-dihydro-1H-isoindol-5-ylmethyl]-ureido}-cyclohexanecarboxylic acid amide as a white solid (130 mg, 30% yield). HPLC: Waters Symmetry $C_{18}$, 5 µm, 3.9×150 mm, 1 mL/min, 240 nm, 5% grad 95% in 5 min, $CH_3CN/0.1\%$ $H_3PO_4$,: $t_R$=4.78 min (92%); mp: 195-197° C.; $^1H$ NMR (DMSO-$d_6$) δ 1.32-1.73 (m, 8H, CHH+CHH+CHH+CHH), 1.97 (br. S., 1H, CHH), 2.09-2.21 (m, 1H, CHH), 2.40 (d, J=13.4 Hz, 1H, CHH), 2.62 (br. S., 1H, CHH), 2.80-3.03 (m, 1H, CHH), 3.70 (br. S., 1H, CHH), 4.18-4.58 (m, 4H, $CH_2$+$CH_2$), 5.11 (dd, 1H, CHN), 6.15 (d, J=7.9 Hz, 1H, NH), 6.38 (t, J=5.9 Hz, 1H, NH), 6.67 (br. S., 1H, NH), 7.19 (br. S., 1H, NH), 7.38 (d, J=7.7 Hz, 1H, Ar), 7.45 (s, 1H, Ar), 7.67 (d, J=7.9 Hz, 1H, Ar), 10.98 (br. S., 1H, NH); $^{13}C$ NMR (DMSO-$d_6$) δ 0.03, 22.42, 24.06, 24.19, 29.73, 41.73, 42.79, 44.16, 47.03, 51.49, 121.68, 122.80, 126.71, 130.09, 142.26, 145.37, 157.28, 163.37, 167.89, 170.92, 172.78, 176.83; LC-MS: 442; Anal Calcd for $C_{22}H_{27}N_5O_5$+0.5 HCOOH+1 $H_2O$+0.2 $CH_3CN$: C, 56.05; H, 6.21; N, 14.84; Found: C, 55.70; H, 6.46; N, 14.78.

5.44 1-(6-Chloro-pyridin-3-yl)-3-[2-(2,6-dioxo-piperidin-3-yl)-1-oxo-2,3-dihydro-1H-isoindol-5-ylmethyl]-urea

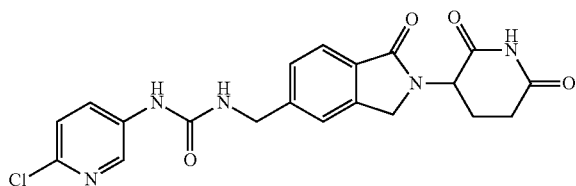

To a suspension of 3-(5-aminomethyl-1-oxo-1,3-dihydro-isoindol-2-yl)-piperidine-2,6-dione methanesulfonic acid salt (0.37 g, 1 mmol) in DMF (3 mL) was added carbonyl diimidazole (162 mg, 1 mmol). The mixture was stirred at room temperature overnight. 5-Amino-2-chloro-pyridine (128.5 mg, 1 mmol) was added to the mixture and the mixture was heated at 80° C. for 6 hours. The mixture was then concentrated under reduced pressure and the resulted mixture was purified on silica gel column eluted with methylene chloride and methanol to give 11-(6-chloro-pyridin-3-yl)-3-[2-(2,6-dioxo-piperidin-3-yl)-1-oxo-2,3-dihydro-1H-isoindol-5-ylmethyl]-urea as an off-white solid (20 mg, 5% yield): HPLC: Waters Symmetry $C_{18}$, 5 µm, 3.9×150 mm, 1 mL/min, 240 nm, 5% grad 95% in 5 min, $CH_3CN/0.1\%$ $H_3PO_4$, $t_R$=5.43 min (97%); mp: 224-226° C.; $^1H$ NMR (DMSO-$d_6$) δ 1.89-2.09 (m, 1H, CHH), 2.29-2.44 (m, 1H, CHH), 2.54-2.66 (m, 1H, CHH), 2.83-3.04 (m, 1H, CHH), 4.20-4.57 (m, 4H, $CH_2,CH_2$), 5.11 (dd, J=5.0, 13.3 Hz, 1H, NCH), 6.99 (t, J=6.2 Hz, 1H, NH), 7.37 (d, J=8.5 Hz, 1H, Ar), 7.45 (d, J=7.7 Hz, 1H, Ar), 7.52 (s, 1H, Ar), 7.70 (d, J=7.7 Hz, 1H, Ar), 7.95 (dd, J=2.8, 8.7 Hz, 1H, Ar), 8.42 (d, J=2.3 Hz, 1H, Ar), 9.03 (s, 1H, NH), 1098 (s, 1H, NH); $^{13}C$ NMR (DMSO-$d_6$) δ 22.49, 31.18, 42.86, 47.12, 51.58, 121.91, 122.94, 123.89, 126.92, 128.37, 130.42, 136.75, 139.04, 142.39, 144.50, 154.97, 167.93, 171.01, 172.86, 215.61; LC-MS: 428; Anal Calcd for $C_{20}H_{18}N_5O_4Cl$+0.1 $H_2O$ C, 55.91; H, 4.27; N, 16.30; Cl, 8.25; Found: C, 56.31; H, 4.51; N, 15.92; Cl, 8.47.

5.45 1-[4-(2,4-Difluoro-phenyl)-thiazol-2-yl]-3-[2-(2,6-dioxo-piperidin-3-yl)-1-oxo-2,3-dihydro-1H-isoindol-5-ylmethyl]-urea

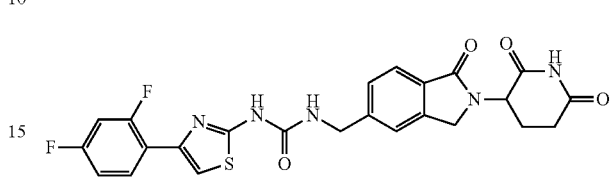

A mixture of 3-(5-aminomethyl-1-oxo-1,3-dihydro-isoindol-2-yl)-piperidine-2,6-dione methanesulfonic acid salt (0.40 g, 1.1 mmol) and CDI (0.18 g, 1.1 mmol) in DMF (5 mL) was stirred at room temperature for 18 h. To the mixture was added 4-(2,4-difluoro-phenyl)-thiazol-2-ylamine (0.23 g, 1.1 mmol) at room temperature, and the mixture was stirred at 100° C. for 2 days. To the mixture was added water (25 mL) and ethyl acetate (20 mL). The mixture was stirred at room temperature for 2 h. The suspension was filtered and the solid was washed with water (20 mL), ethyl acetate (20 mL) and water (20 mL) to give a solid. The solid was purified with Prep HPLC to give 1-[4-(2,4-difluoro-phenyl)-thiazol-2-yl]-3-[2-(2,6-dioxo-piperidin-3-yl)-1-oxo-2,3-dihydro-1H-isoindol-5-ylmethyl]-urea as a white solid (70 mg, 13% yield): HPLC: Waters Symmetry C18, 5 µm, 3.9×150 mm, 1 mL/min, 240 nm, 40/60 CH3CN/0.% H3PO4, 6.43 min (97.7%); mp: 264-266° C.; 1H NMR (DMSO-d6) 1.93-2.05 (m, 1H, CHH), 2.30-2.45 (m, 1H, CHH), 2.55-2.68 (m, 1H, CHH), 2.82-3.00 (m, 1H, CHH), 4.32 (d, J=17.4 Hz, 1H, CHH), 4.41-4.54 (m, 3H, CH2, CHH), 5.11 (dd, J=5.1, 13.2 Hz, 1H, NCH), 7.09-7.24 (m, 2H, Ar, NH), 7.28-7.41 (m, 2H, Ar), 7.46 (d, J=7.7 Hz, 1H, Ar), 7.53 (s, 1H, Ar), 7.71 (d, J=7.9 Hz, 1H, Ar), 7.93-8.10 (m, 1H, Ar), 10.85 (s, 1H, NH), 10.98 (s, 1H, NH); 13C NMR (DMSO-d6) 22.48, 31.18, 42.94, 47.12, 51.57, 104.54 (t, JC-F=26.4 Hz), 110.67 (d, JC-F=14.3 Hz), 111.81 (dd, JC-F=3.3, 20.9 Hz), 118.91 (dd, JC-F=2.8. 11.6 Hz), 121.95, 123.03, 126.95, 130.29 (dd, JC-F=4.4, 9.9 Hz), 130.49, 141.44, 142.45, 143.95, 154.02, 159.48 (dd, JC-F=252.2, 12.1 Hz), 159.36, 161.24 (dd, JC-F=246.9, 13.2 Hz), 167.88, 170.98, 172.85; LCMS MH=512; Anal. Calcd for C24H19N5O4F2S: C, 56.36; H, 3.74; N, 13.69; Found: C, 56.16; H, 3.80; N, 14.07.

5.46 6-{3-[2-(2,6-Dioxo-piperidin-3-yl)-1-oxo-2,3-dihydro-1H-isoindol-5-ylmethyl]-ureido}-3,4-dihydro-1H-isoquinoline-2-carboxylic Acid Tert-Butyl Ester

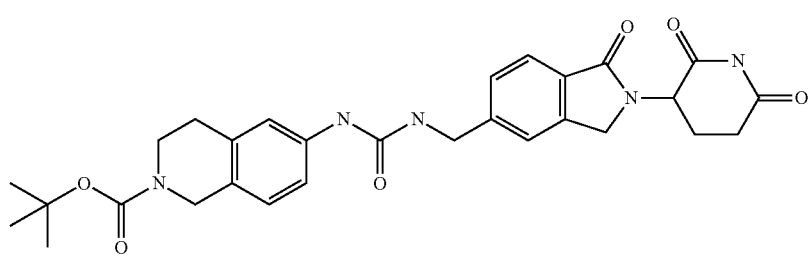

3-(5-aminomethyl-1-oxo-1,3-dihydro-isoindol-2-yl)-piperidine-2,6-dione methanesulfonate (1.11 g, 3.0 mmol) and 1,1'-Carbonyldiimidazole (535 mg, 3.3 mmol) were suspended in dry DMF (20 mL) and the mixture was stirred at rt for 24 h. While stirring, a portion of the reaction mixture (6.7 mL, ~1 mmol) was transferred to a vial containing tert-butyl 6-amino-3,4-dihydroisoquinoline-2(1H)-carboxylate (273 mg, 1.1 mmol). The resulting mixture was stirred at rt overnight and the reaction progress was monitored by LCMS. After 48 h, additional tert-butyl 6-amino-3,4-dihydroisoquinoline-2(1H)-carboxylate (50 mg, 0.2 mmol) was transferred to the reaction mixture and stirring continued for another 24 h. The reaction mixture was acidified with acidic acid and water. The volatiles were removed in vacuo and the residue was dissolved in DMF and purified using C-18 preparatory HPLC to give 6-{3-[2-(2,6-dioxo-piperidin-3-yl)-1-oxo-2,3-dihydro-1H-isoindol-5-ylmethyl]-ureido}-3,4-dihydro-1H-isoquinoline-2-carboxylic acid tert-butyl ester as a white solid (290 mg, 53% yield): HPLC: Waters Symmetry $C_{18}$, 5 μm, 3.9×150 mm, 1 ml/min, 240 nm, 40/60 $CH_3CN$/0.1% $H_3PO_4$, 5.02 min (96.5%): mp: 230-232° C.; $^1H$ NMR (DMSO-$d_6$) δ 1.42 (s, 9H, $(CH_3)_3$), 1.90-2.11 (m, 1H, CHH), 2.23-2.47 (m, 1H, CHH), 2.60 (d, J=17.9 Hz, 1H, CHH), 2.70 (t, J=5.6 Hz, 2H, $CH_2$), 2.81-3.06 (m, 1H, CHH), 3.51 (t, 5.7 Hz, 2H, $CH_2$), 4.18-4.58 (m, 6H, $CH_2$, $CH_2$, $CH_2$), 5.11 (dd, J=4.9, 13.2 Hz, 1H, CH), 6.72 (t, J=5.9 Hz, 1H, NH), 7.00 (d, J=8.3 Hz, 1H, Ar), 7.17 (d, J=8.1 Hz, 1H, Ar), 7.27 (br. s., 1H, Ar), 7.44 (d, J=7.9 Hz, 1H, Ar), 7.51 (s, 1H, Ar), 7.69 (d, J=7.9 Hz, 1H, Ar), 8.56 (s, 1H, NH), 10.98 (s, 1H, NH); $^{13}C$ NMR (DMSO-$d_6$) δ 22.46, 28.07, 28.44, 31.16, 41.51, 42.75, 45.04, 47.08, 51.55, 78.81, 116.01, 117.49, 121.87, 122.90, 126.20, 126.36, 126.88, 130.25, 134.70, 138.56, 142.35, 144.86, 153.97, 155.21, 167.93, 170.96, 172.83; LCMS: MH=548: Anal Calcd for $C_{29}H_{33}N_5O_6$+1.1 $H_2O$: C, 61.39; H, 6.25; N, 12.34. Found: C, 61.38; H, 6.11; N, 12.29.

5.47 Isoindolin Compounds of Formula III

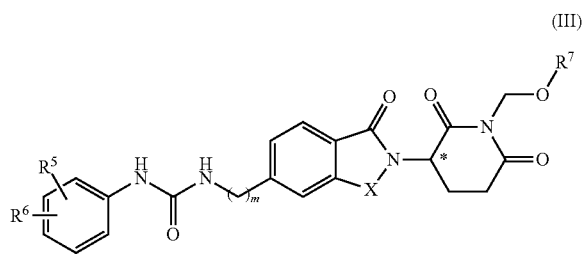

(III)

The isoindolin compounds of Formula III are made as shown in Scheme 1.

Scheme 1

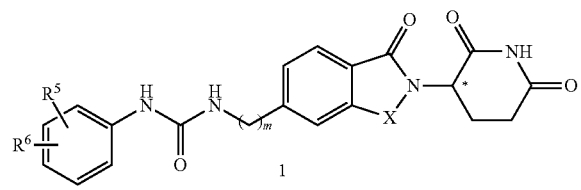

1

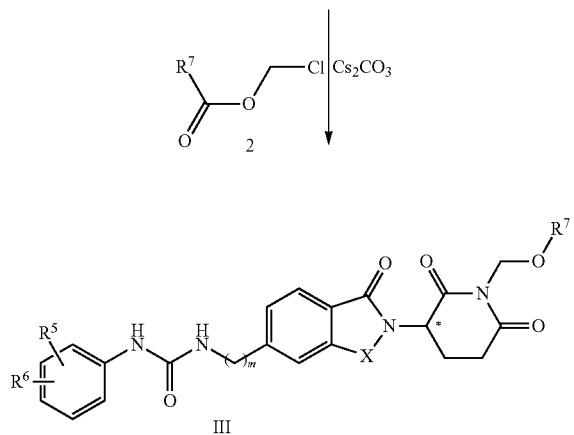

2

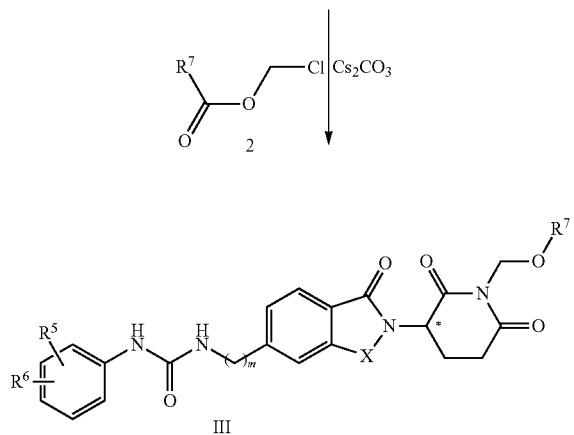

III

To a solution of the 5-aminomethylisoindolinone glutarimide 1 (1.134 mmol) in dry DMF (10 mL) is added $Cs_2CO_3$ (406 mg, 1.248 mmol). After 5 minutes of stirring, an appropriate chloromethoxycarbonyl reagent 2 (1.248 mmol) is added and the resulting mixture is stirred at 50° C. overnight. The reaction mixture is neutralized with 0.5N HCl and then concentrated to dryness in vacuo. The residue is purified by preparative HPLC, followed by the removal of protecting groups, if necessary, under standard conditions to yield a compound of Formula III.

5.48 2,2-Dimethyl-propionic acid 3-{5-[3-(3-chloro-4-methyl-phenyl)-ureidomethyl]-1-oxo-1,3-dihydro-isoindol-2-yl}-2,6-dioxo-piperidin-1-ylmethyl Ester

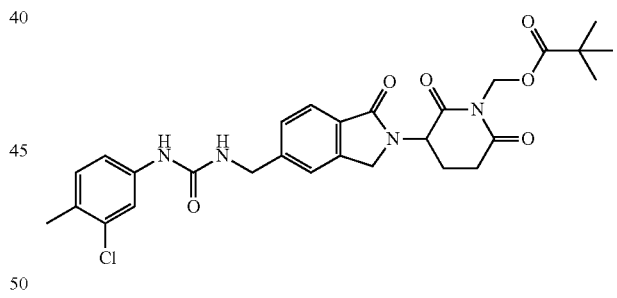

To a solution of 1-(3-chloro-4-methyl-phenyl)-3-[2-(2,6-dioxo-piperidin-3-yl)-1-oxo-2,3-dihydro-1H-isoindol-5-ylmethyl]-urea (500 mg, 1.134 mmol) in dry DMF (10 mL) was added $Cs_2CO_3$ (406 mg, 1.248 mmol). After 5 min of stirring, chloromethyl pivalate (188 mg, 1.248 mmol) was added and the resulting mixture was stirred at 50° C. overnight. The reaction mixture was neutralized with 0.5N HCl and then concentrated to dryness in vacuo. The residue was dissolved in acetonitrile and water was added slowly resulting in a precipitate to form. The solid was collected by filtration and dissolved in DMF for purification on a C-18 preparative HPLC column (50/50 $CH_3CN$/water). Fractions containing the desired product were combined, concentrated in vacuo to remove most of the CH$_3$CN, and then lyophilized to provide the product as a white solid (81 mg, 13% yield):HPLC: Waters Symmetry C$_{18}$, 5 μm, 3.9×150 mm, 1 mL/min, 240 nm, 55/45 CH$_3$CN/0.1% H$_3$PO$_4$, 4.58 min (97.2%); mp: 155-157° C.; $^1$H NMR (DMSO-d$_6$) δ 0.95-1.23 (m, 9H, $^t$Bu), 1.96-2.15 (m, 1H, CH), 2.23 (s, 3H, CH$_3$), 2.31-2.47 (m, 1H, CH), 2.83 (d, J=16.6 Hz, 1H, CH), 3.00-3.22 (m, 1H, CH), 4.17-4.60 (m, 4H, CH$_2$, CH$_2$), 5.30 (dd, J=5.0, 13.3 Hz, 1H, CH), 5.47-5.83 (m, 2H, CH$_2$), 6.79 (t, J=5.9 Hz, 1H, CH$_2$NH), 7.02-7.28 (m, 2H, Ar), 7.36-7.60 (m, 2H, Ar), 7.60-7.86 (m, 2H, Ar), 8.74 (s, 1H, NH); $^{13}$C NMR (DMSO-d$_6$) δ 18.73, 21.56, 26.62, 31.21, 38.21, 42.79, 47.04, 52.01, 63.39, 116.45, 117.66, 121.95, 123.01, 126.98, 127.42, 130.11, 131.00, 132.99, 139.58, 142.36, 144.87, 155.07, 167.96, 170.13, 171.23, 176.51; LCMS: MH$^+$=555, 557; Anal. Calcd. for C$_{28}$H$_{31}$ClN$_4$O$_6$+0.2 H$_2$O: C, 60.20; H, 5.67; N, 10.03; Cl, 6.35; Found: C, 60.20; H, 5.74; N, 9.94; Cl, 6.39.

5.49 (3-(5-((3-(3-Chloro-4-methylphenyl)ureido) methyl)-1-oxoisoindolin-2-yl)-2,6-dioxopiperidin-1-yl)methyl piperidine-4-carboxylate Hydrochloride 4-methylphenyl)ureido)methyl)-1-oxoisoindolin-2-yl)-2,6-dioxopiperidin-1-yl)methyl piperidine-4-carboxylate Hydrochloride as a white solid (285 mg, 105% yield): HPLC: Waters Symmetry C$_{18}$, 5 μm, 3.9×150 mm, 1 ml/min, 240 nm, 30/70 CH$_3$CN/0.1% H$_3$PO$_4$, 3.26 min (98.2%); mp: 234-236° C.; $^1$H NMR (DMSO-d$_6$) δ 1.62-1.81 (m, 2H, CHH, CHH), 1.87-2.01 (m, 2H, CHH, CHH), 2.02-2.16 (m, 1H, CHH), 2.16-2.29 (m, 3H, CH$_3$), 2.32-2.47 (m, 1H, CHH), 2.59-2.76 (m, 1H, CHH), 2.77-2.99 (m, 3H, CHH, CHH, CHH), 3.00-3.28 (m, 3H, CHH, CHH, CHH), 4.15-4.66 (m, 4H, CH$_2$, CH$_2$), 5.26 (dd, J=4.9, 13.2 Hz, 1H, CH), 5.55-5.80 (m, 2H, CH$_2$O), 7.02 (t, J=5.9 Hz, 1H, NH), 7.09-7.29 (m, 2H, Ar), 7.45 (d, J=7.9 Hz, 1H, Ar), 7.53 (s, 1H, Ar), 7.62-7.82 (m, 2H, Ar), 8.41-8.96 (m, 2H, NH, NH), 9.09 (s, 1H, NH); $^{13}$C NMR (DMSO-d$_6$) δ 18.73, 21.46, 24.31, 31.24, 37.30, 42.00, 42.73, 47.20, 52.09, 63.40, 116.31, 117.50, 121.91, 122.99, 126.97, 127.27, 130.09, 130.99, 132.96, 139.69, 142.38, 144.94, 155.21, 167.96, 170.19, 171.29, 172.20; LCMS: MH=582, 584; Anal Calcd for C$_{29}$H$_{33}$Cl$_2$N$_5$O$_6$+1.6 H$_2$O+0.6

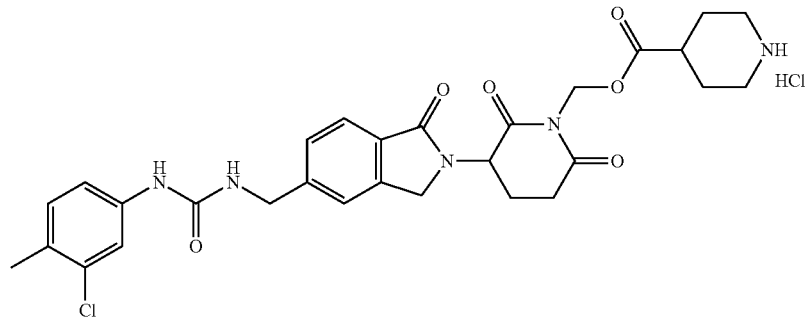

To 1-tert-butyl 4-(3-(5-((3-(3-chloro-4-methylphenyl)ureido)methyl)-1-oxoisoindolin-2-yl)-2,6-dioxopiperidin-1-yl) methyl piperidine-1,4-dicarboxylate (300 mg, 0.44 mmol, obtained as described in previous example) was added 2 N HCl in Et$_2$O (15 mL). The slurry was vigorously stirred for 2 h at rt. The solid was filtered, washed with copious Et$_2$O, and dried in a vacuum oven overnight to give (3-(5-((3-(3-chloro- HCl+0.2 Et$_2$O+0.4 $^t$BuCl: C, 53.35; H, 6.05; N, 9.91; Cl, 13.04. Found: C, 53.13; H, 6.06; N, 9.70; Cl, 13.25.

5.50 1-tert-Butyl 4-(3-(5-((3-(3-chloro-4-methylphenyl)ureido)methyl)-1-oxoisoindolin-2-yl)-2,6-dioxopiperidin-1-yl)methyl piperidine-1,4-dicarboxylate

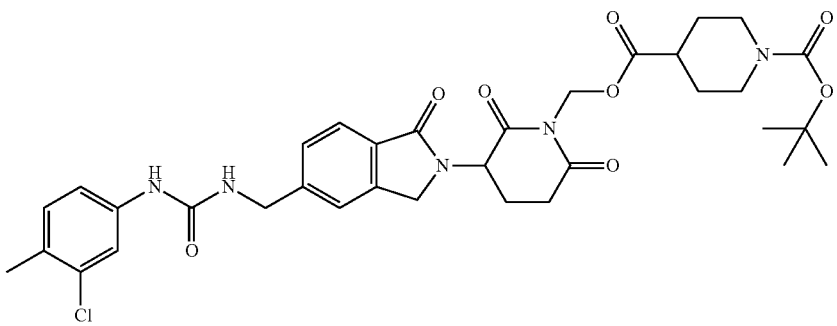

Step 1: 1-tert-Butyl 4-chloromethyl piperidine-1,4-dicarboxylate

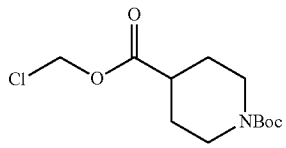

To a mixture of 1-(tert-butoxycarbonyl)piperidine-4-carboxylic acid (3 g, 13.1 mmol) in dichloromethane (40 mL) and water (50 mL) was added NaHCO$_3$ (4.4 g, 52.3 mmol) and tetrabutylammonium hydrogen sulfate (444 mg, 1.3 mmol). After stirring the mixture in an ice bath at 0° C. for ~10 min, chloromethyl chlorosulfate (2.59 g, 15.7 mmol) in 10 mL of dichloromethane was added dropwise. The reaction mixture was allowed to warm up to rt and stirred vigorously overnight. The mixture was transferred to a separatory funnel with dichloromethane and water (200 mL, each). The organic layer was washed with additional water and brine, dried (Na$_2$SO$_4$), and concentrated in vacuo to give 1-tert-butyl 4-chloromethyl piperidine-1,4-dicarboxylate as a clear oil (3.5 g, 96% yield). This material was used without further purification. $^1$H NMR (DMSO-d$_6$) δ 1.26-1.48 (m, 11H, CHH, CHH, tertBu), 1.83 (dd, J=3.0, 13.2 Hz, 2H, CHH, CHH), 2.58-2.75 (m, 1H, CH), 2.74-2.99 (m, 2H, CHH, CHH), 3.61-4.02 (m, 2H, CHH, CHH), 5.87 (s, 2H, CH$_2$O); $^{13}$C NMR (DMSO-d$_6$) δ 27.16, 27.98, 39.58, 42.35, 69.41, 78.67, 153.75, 172.25; LCMS: MH=278.

Step 2: 1-tert-Butyl 4-iodomethyl piperidine-1,4-dicarboxylate

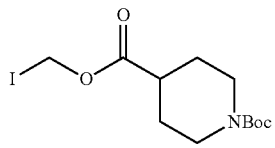

To a solution of NaI (1.6 g, 11.09 mmol) in dry acetonitrile (8 mL) was added dropwise 1-tert-butyl 4-chloromethyl piperidine-1,4-dicarboxylate (2.8 g, 10.08 mmol) in 2 mL of acetonitrile. The mixture turned dark orange and was stirred at rt in the dark for 24 h. The reaction mixture was filtered to remove NaCl and the filtrate was concentrated in vacuo. The remaining residue was partitioned between DCM and 5% aq NaHSO$_3$ solution. The organic layer was washed with water and brine, dried (Na$_2$SO$_4$), and concentrated in vacuo to give 1-tert-butyl 4-iodomethyl piperidine-1,4-dicarboxylate as a pale yellow oil (3.5 g, 94%). Attempts to characterize by NMR in DMSO-d$_6$ resulted in rapid decomposition. The material was stored in the dark at −20° C. to minimize decomposition before further use. LCMS: MH=370.

Step 3: 1-tert-Butyl 4-(3-(5-((3-(3-chloro-4-methylphenyl)ureido)methyl)-1-oxoisoindolin-2-yl)-2,6-dioxopiperidin-1-yl)methylpiperidine-1,4-dicarboxylate

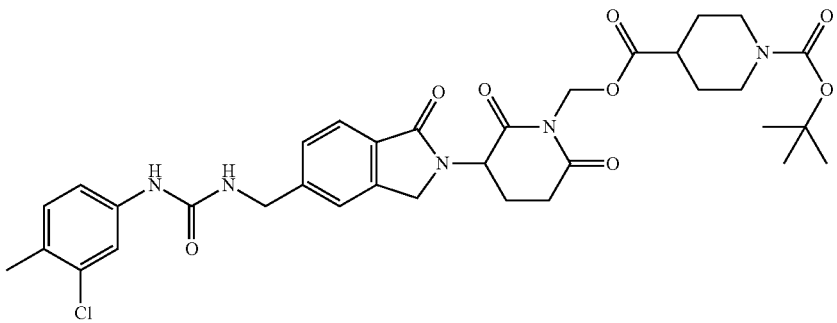

1-(3-Chloro-4-methyl-phenyl)-3-[2-(2,6-dioxo-piperidin-3-yl)-1-oxo-2,3-dihydro-1H-isoindol-5-ylmethyl]-urea (400 mg, 0.907 mmol) and NaH (43.5 mg, 1.82 mmol) were stirred in dry DMF (15 mL) for ~10 min. To the mixture was added 1-tert-butyl 4-iodomethyl piperidine-1,4-dicarboxylate (402 mg, 1.09 mmol) and the reaction stirred in the dark at rt for 2 h. The reaction was quenched with acetic acid (5 mL) and concentrated in vacuo. The residue was partitioned in water and EtOAc (100 mL, each). The separated organic layer was washed with additional water and brine, dried (Na$_2$SO$_4$), and concentrated in vacuo to give 1.4 gm of a yellowish solid which was dissolved in DMF for purification on a C-18 prep HPLC column. Fractions containing the desired product were combined, concentrated in vacuo to remove most of the CH$_3$CN, and then lyophilized to provide 1-tert-butyl 4-(3-(5-((3-(3-chloro-4-methylphenyl)ureido)methyl)-1-oxoisoindolin-2-yl)-2,6-dioxopiperidin-1-yl)methyl piperidine-1,4-dicarboxylate as a white solid (380 mg, 49% of theoretical yield from two separate runs that were combined before prep HPLC). HPLC:Waters Symmetry C$_{18}$, 5 μm, 3.9×150 mm, 1 ml/min, 240 nm, 55/45 CH$_3$CN/0.1% H$_3$PO$_4$, 5.82 min (99.4%); mp: 157-159° C.; $^1$H NMR (DMSO-d$_6$) δ 1.23-1.51 (m, 11H, (CH$_3$)$_3$, CHH, CHH), 1.68-1.84 (m, 2H, CHH, CHH), 1.97-2.13 (m, 1H, CHH), 2.15-2.31 (m, 4H, CH$_3$, CH), 2.32-2.46 (m, 1H, CHH), 2.68-2.94 (m, 3H, CHH, CHH, CHH), 2.98-3.21 (m, 1H, CHH), 3.69-3.89 (m, 2H, CHH, CHH), 4.20-4.57 (m, 4H, CH$_2$, CH$_2$), 5.27 (dd, J=5.0, 13.3 Hz, 1H, CH), 5.53-5.73 (m, 2H, CH$_2$O), 6.81 (t, J=5.9 Hz, 1H, NH), 7.06-7.24 (m, 2H, Ar), 7.45 (d, J=7.9 Hz, 1H, Ar), 7.53 (s, 1H, NH), 7.67 (d, J=1.9 Hz, 1H, Ar), 7.71 (d, J=7.7 Hz, 1H, Ar), 8.76 (s, 1H, NH); $^{13}$C NMR (DMSO-d$_6$) δ 18.66, 21.39, 27.38, 27.97, 31.16, 42.72, 47.08, 51.98, 63.15, 78.60, 116.37, 117.60, 121.88, 122.93, 126.91, 127.34, 130.06, 130.94, 132.91, 139.52, 142.32, 144.82, 153.74, 155.01, 167.90, 170.11, 171.18, 172.97 (two $^{13}$C signals arising from the piperidine ring are not observed due to overlap with DMSO-d$_6$); LCMS: MH=682, 684; Anal Calcd for C$_{34}$H$_{40}$ClN$_5$O$_8$+1.0 H$_2$O: C, 58.32; H, 6.05; N, 10.00; Cl, 5.06. Found: C, 58.41; H, 5.93; N, 9.96; Cl, 5.22.

5.51 N-[2-(2,6-Dioxo-piperidin-3-yl)-1-oxo-2,3-dihydro-1H-isoindol-5-ylmethyl]-4-imidazol-1-yl-benzamide

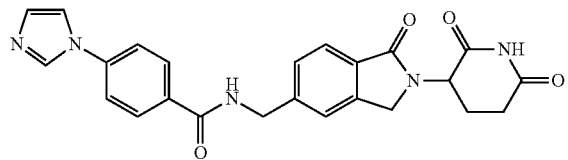

A mixture of 4-imidazol-1-yl-benzoic acid (0.21 g, 1.1 mmol) and CDI (0.19 g, 1.2 mmol) in DMF (14 mL) was stirred at 40° C. for 2 hrs. To the suspension was added 3-(5-aminomethyl-1-oxo-1,3-dihydro-isoindol-2-yl)-piperidine-2,6-dione methanesulfonic acid salt (0.40 g, 1.1 mmol) and the mixture was stirred at 40° C. for 20 hrs. Water (20 mL) was added to the reaction mixture and the mixture was stirred at RT for 30 min. The suspension was filtered and the solid was washed with water (20 mL), ethyl acetate (20 mL), and water (20 mL) to give the product as a white solid (340 mg, 71% yield): HPLC: Waters Xterra C$_{18}$, 5 µm, 3.9×150 mm, 1 mL/min, 240 nm, 5% gradient 95% in 5 min, CH$_3$CN/0.1% NH$_4$OOCH, 3.92 min (99.0%); mp: 268-270° C.; $^1$H NMR (DMSO-d$_6$) δ 1.90-2.08 (m, 1 H, CHH), 2.24-2.47 (m, 1H, CHH), 2.54-2.67 (m, 1H, CHH), 2.82-3.02 (m, 1H, CHH), 4.31 (d, J=17.4 Hz, 1H, CHH), 4.45 (d, J=17.4 Hz, 1H, CHH), 4.62 (d, J=5.7 Hz, 2H, CH$_2$), 5.11 (dd, J=5.1, 13.2 Hz, 1H, NCH), 7.14 (s, 1H, Ar), 7.49 (d, J=7.9 Hz, 1H, Ar), 7.56 (s, 1H, Ar), 7.71 (d, J=7.7 Hz, 1H, Ar), 7.77-7.91 (m, 3H, Ar), 8.05 (d, J=8.7 Hz, 2H, Ar), 8.39 (s, 1H, Ar), 9.24 (t, J=5.9 Hz, 1H, NH), 10.98 (br. s., 1H, NH); $^{13}$C NMR (DMSO-d$_6$) δ 22.49, 31.20, 42.79, 47.13, 51.58, 117.78, 119.59, 122.10, 122.97, 127.08, 129.02, 130.20, 130.39, 132.07, 135.60, 138.99, 142.40, 143.83, 165.25, 167.92, 170.99, 172.86; LCMS: MH$^+$=444; Anal. Calcd. for C$_{24}$H$_{21}$N$_5$O$_4$+1.5 H$_2$O; C, 61.27; H, 5.14; N, 14.89; Found: C, 61.03; H, 4.93; N, 14.75.

5.52 N-[2-(2,6-Dioxo-piperidin-3-yl)-1-oxo-2,3-dihydro-1H-isoindol-5-ylmethyl]-4-morpholio-4-yl-benzamide

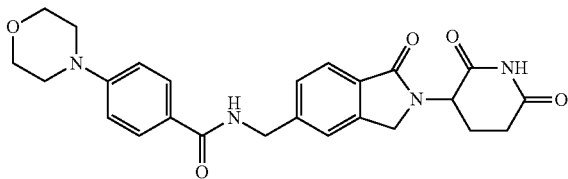

A mixture of 4-morpholin-4-yl-benzoic acid (0.22 g, 1.1 mmol) and CDI (0.19 g, 1.2 mmol) in DMF (4 mL) was stirred at 40° C. for 2 hrs. To the suspension was added 3-(5-aminomethyl-1-oxo-1,3-dihydro-isoindol-2-yl)-piperidine-2,6-dione methanesulfonic acid salt (0.40 g, 1.1 mmol), and the mixture was stirred at 40° C. for 2 hrs. Water (20 mL) was added to the reaction mixture and the mixture was stirred at RT for 30 min. The suspension was filtered and the solid was washed with water (20 mL), ethyl acetate (20 mL), and water (20 mL) to give the product as a white solid (370 mg, 74% yield): HPLC: Waters Xterra C$_{18}$, 5 µm, 3.9×150 mm, 1 mL/min, 240 nm, 5% gradient 95% in 5 min, CH$_3$CN/0.1% NH4OOCH, 1.10 min (96.5%); mp: 275-277° C.; $^1$H NMR (DMSO-d$_6$) δ 2.00 (d, J=5.1 Hz, 1H, CHH), 2.38 (m, 1H, CHH), 2.54-2.66 (m, 1H, CHH), 2.81-3.01 (m, 1H, CHH), 3.15-3.28 (m, 4H, CH$_2$, CH$_2$), 3.65-3.80 (m, 4H, CH$_2$, CH$_2$), 4.30 (d, J=17.4 Hz, 1H, CHH), 4.44 (d, J=17.6 Hz, 1H, CHH), 4.56 (d, J=5.9 Hz, 2H, CH$_2$), 5.10 (dd, J=5.1, 13.2 Hz, 1H, NCH), 6.98 (d, J=9.1 Hz, 2H, Ar), 7.45 (d, J=7.9 Hz, 1H, Ar), 7.51 (s, 1H, Ar), 7.68 (d, J=7.9 Hz, 1H, Ar), 7.81 (d, J=8.9 Hz, 2H, Ar), 8.88 (s, 1H, NH), 10.98 (s, 1H, NH); $^{13}$C NMR (DMSO-d$_6$) δ 22.46, 31.15, 42.54, 47.07, 47.33, 51.53, 65.86, 113.40, 121.96, 122.86, 123.72, 126.99, 128.50, 130.24, 142.31, 144.38, 152.95, 165.87, 167.91, 170.96, 172.83; LCMS: MH$^+$=463; Anal. Calcd. for C$_{25}$H$_{26}$N$_4$O$_5$+0.6 H$_2$O: C, 63.44; H, 5.79; N, 11.84; Found: C, 63.19; H, 5.42; N, 12.09.

5.53 2-Amino-2-(4-chlorophenyl)-N-((2-(2,6-dioxopiperidin-3-yl)-1-oxoisoindolin-5-yl)methyl)acetamide Hydrochloride

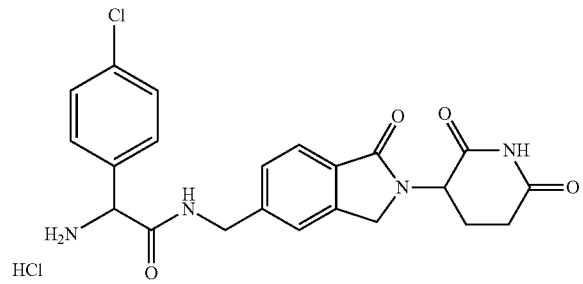

Step 1: To a stirred solution of N-Boc-(4'-chlorophenyl) glycine (1.16 g, 4.10 mmol) in DMF (20 mL) was added CDI (0.69 g, 4.30 mmol). The reaction mixture was heated to 40° C. for 2 hrs. 3-(5-Aminomethyl-1-oxo-1,3-dihydro-isoindol-2-yl)-piperidine-2,6-dione hydrochloride (1.50 g, 4.10 mmol) was then added. After 3.5 hrs at 40° C. water (70 mL) was added. Solid precipitated was isolated by filtration, washed with water (3×20 mL), and dried in vacuo to afford tert-butyl 1-(4-chlorophenyl)-2-((2-(2,6-dioxopiperidin-3-yl)-1-oxoisoindolin-5-yl)methylamino)-2-oxoethylcarbamate as a white solid (1.77 g, 80% yield). The crude product was used in the next step without further purification.

Step 2: To a stirred solution of tert-butyl 1-(4-chlorophenyl)-2-((2-(2,6-dioxopiperidin-3-yl)-1-oxoisoindolin-5-yl) methylamino)-2-oxoethylcarbamate (0.84 g, 1.50 mmol) in EtOAc (35 mL) was added a solution of diluted HCl (2N in ether, 30 mL). After 3 days, solid was isolated by filtration, washed with ether (3×10 mL), and dried in vacuo. The solid was then dissolved in water (100 mL) and extracted with EtOAc (2×50 mL). The aqueous phase was concentrated and the residue was triturated with ether for 1 hr. The product was isolated by filtration and dried in vacuo to give the product as a white solid (0.65 g, 88% yield): HPLC: Waters Symmetry C$_{18}$, 5 µm, 3.9×150 mm, 1 mL/min, 240 nm, gradient: CH$_3$CN/0.1% H$_3$PO$_4$: 10/90 to 90/10 in 10 min, 90/10 (5 min): 4.91 min (98.00%); mp: 255-257° C.; $^1$H NMR (DMSO-$_6$) δ 1.93-2.09 (m, 1H, CHH), 2.39 (qd, J=4.4, 13.1

Hz, 1H, CHH), 2.54-2.69 (m, 1H, CHH), 2.82-3.03 (m, 1H, CHH), 4.24 (d, J=17.4 Hz, 1H, CHH), 4.30-4.54 (m, 3H, CH₂, CHH), 5.02-5.19 (m, 2H, CH, CH), 7.22-7.41 (m, 2H, Ar), 7.47-7.71 (m, 5H, Ar), 9.35 (t, J=5.9 Hz, 1H, NH), 10.99 (s, 1H, NH); $^{13}$C NMR (DMSO-d₆) δ 22.48, 31.20, 42.26, 47.03, 51.59, 54.80, 121.89, 121.96, 122.85, 126.97, 128.80, 129.81, 130.49, 133.02, 133.99, 142.27, 142.70, 167.22, 167.82, 170.98, 172.85; LCMS: MH⁺=441/443; Anal. Calcd. for $C_{22}H_{22}N_4O_4Cl_2$+0.6 H₂O: C, 54.13; H, 4.79; N, 11.48; Found: C, 53.89; H, 4.82; N, 11.60.

5.54 2-Amino-5-chloro-N-[2-(2,6-dioxo-piperidin-3-yl)-1-oxo-2,3-dihydro-1H-isoindol-5-ylmethyl]-benzamide

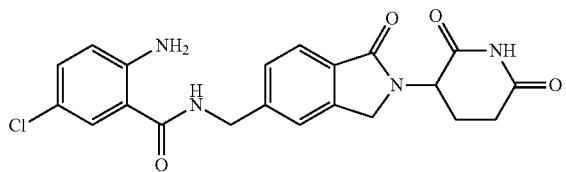

DIPEA (1.46 mL, 8.12 mmol) was added to a stirred mixture of 3-(5-aminomethyl-1-oxo-1,3-dihydro-isoindol-2-yl)-piperidine-2,6-dione methanesulfonate (1.0 g, 2.71 mmol) and 5-chloro-isatoic anhydride 3 (0.535 g, 2.71 mmol) in acetonitrile (10 mL) under nitrogen. The reaction mixture was refluxed for 14 hrs, at which time LCMS indicated the reaction was complete. Water was added to the slurry and the solid was collected by filtration, washed with additional water, and dried in vacuo to provide the product as a white solid (860 mg, 74% yield): HPLC: Waters Symmetry $C_{18}$, 5 μm, 3.9×150 min, 1 mL/min, 240 nm, 30/70 CH₃CN/0.1% H₃PO₄, 6.30 min (98.7%); mp: 242-244° C.; $^1$H NMR (DMSO-d₆) δ 1.79-2.16 (m, 1H, CHH), 2.29-2.46 (m, 1H, CHH), 2.60 (d, J=16.6 Hz, 1H, CHH), 2.74-3.08 (m, 1H, CHH), 4.08-4.69 (m, 4H, CH₂, CH₂), 5.11 (dd, J=4.9, 13.2 Hz, 1H, CH), 6.60 (s, 2H, NH₂), 6.73 (d, J=8.7 Hz, 1H, Ar), 7.18 (dd, J=2.4, 8.8 Hz, 1H, Ar), 7.46 (d, J=7.9 Hz, 1H, Ar), 7.53 (s, 1H, Ar), 7.59-7.76 (m, 2H, Ar), 9.01 (t, J=5.8 Hz, 1H, NH), 10.98 (s, 1H, NH); $^{13}$C NMR (DMSO-d₆) δ 22.51, 31.20, 42.44, 47.12, 51.56, 114.81, 117.71, 118.12, 122.07, 122.91, 127.07, 127.33, 130.35, 131.60, 142.38, 143.92, 148.78, 167.67, 167.92, 170.98, 172.85; LCMS: MH⁺=427, 429; Anal. Calcd. for $C_{21}H_{19}ClN_4O_4$+0.2 H₂O: C, 58.73; H, 4.32; N, 13.05; Found: C, 58.68; H, 4.26; N, 12.80.

5.55 Isoindolin Compounds

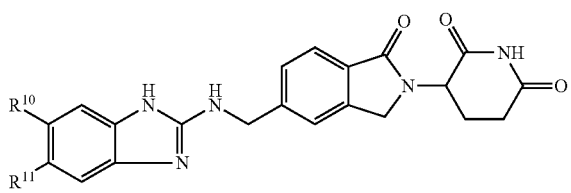

The isoindolin compounds shown above are made as shown in Scheme 2.

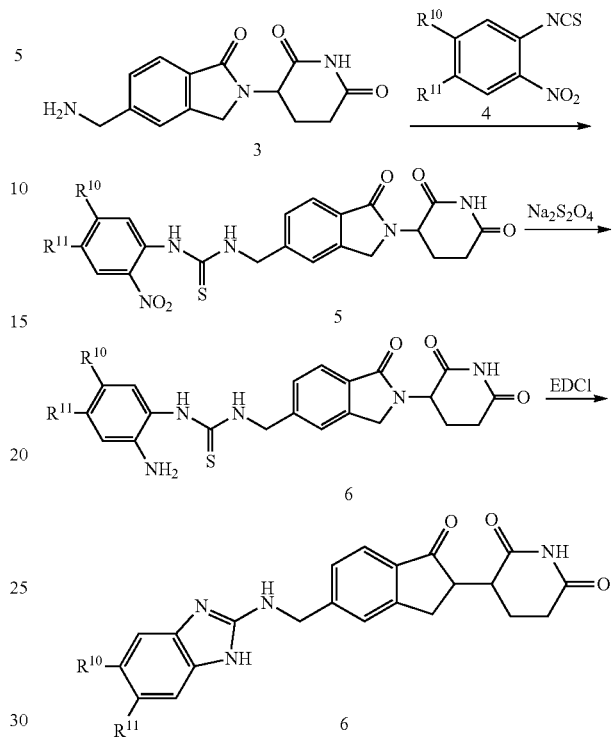

Scheme 2

Step 1: DIPEA (2.0 mmol, 2 eq.) is added to a stirred mixture of 3-(5-aminomethyl-1-oxo-1,3-dihydro-isoindol-2-yl)-piperidine-2,6-dione methanesulfonate 3 (0.26 g, 1.0 mmol) and an appropriate nitrophenylisothiocyanate 4 (1.1 mmol) in acetonitrile (10 mL) under nitrogen. The mixture is stirred at RT for 12 hrs. 1N HCl solution (10 mL) is added and the solid formed is filtered, washed with additional water, and dried to provide substituted 1-((2-(2,6-dioxopiperidin-3-yl)-1-oxoisoindolin-5-yl)methyl)-3-(2-nitrophenyl)thiourea 5.

Step 2: To a stirred mixture this intermediate 5 (1.0 mmol) in EtOH (10 mL) is added a solution of sodium dithionite (1.74 g, 10 mmol) in water (10 mL). The mixture is heated to 60° C. for 1 hr. The reaction mixture is concentrated to dryness to yield compound 6, which is used directly in the next step without further purification.

Step 3: Compound 6 is suspended in DMF and EDCI (0.19 g, 1.0 mmol) is added. The mixture is stirred overnight and the reaction mixture is quenched by addition of acetic acid (2 mL). The crude product is purified using preparative HPLC to provide a compound 7.

5.56 Isoindoline Compounds

According to the procedures provided in Sections 5.34-5.35, 1-((2-(2,6-dioxopiperidin-3-yl)-1-oxoisoindolin-5-yl)methyl)-3-(2-hydroxy-4,5-dimethylphenyl)urea are prepared starting from 4,5-dimethyl-2-nitrophenol.

General Procedure A: A mixture of the appropriate carboxylic acid starting material (2.0 mmol) and CDI (0.32 g, 2.0 mmol) in DMF (30 mL) is stirred for 2 hours at 40° C., and then 3-(5-(aminomethyl)-1-oxoisoindolin-2-yl)piperidine-2,6-dione methanesulfonate (0.74 g, 2.0 mmol) is added, and stirring proceeds for 24 hours. The mixture is evaporated under vacuum and the residue is purified by preparative HPLC.

Using the General Procedure A, the following compounds are prepared:

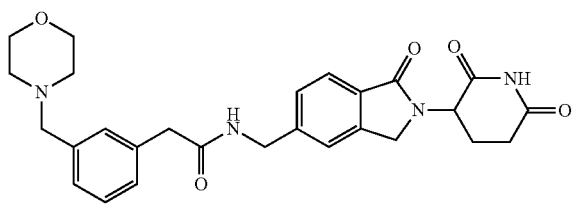

N-((2-(2,6-dioxopiperidin-3-yl)-1-oxoisoindolin-5-yl)methyl)-2-(3-(morpholinomethyl)phenyl)acetamide;

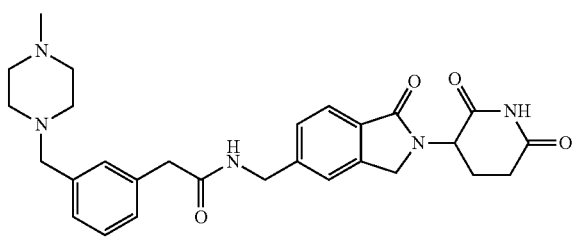

N-((2-(2,6-dioxopiperidin-3-yl)-1-oxoisoindolin-5-yl)methyl)-2-(3-((4-methylpiperazin-1-yl)methyl)phenyl)acetamide;

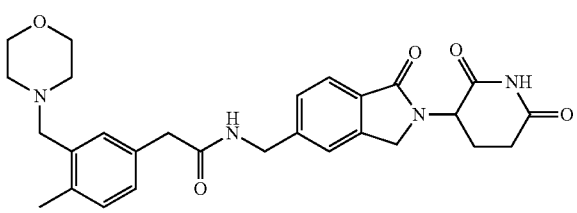

N-((2-(2,6-dioxopiperidin-3-yl)-1-oxoisoindolin-5-yl)methyl)-2-(4-methyl-3-(morpholinomethyl)phenyl)acetamide;

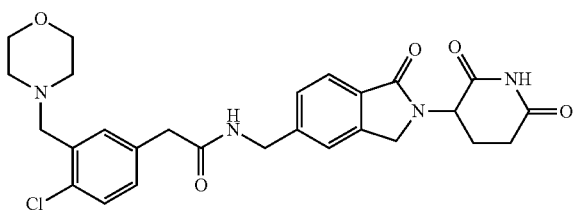

2-(4-chloro-3-(morpholinomethyl)phenyl)-N-((2-(2,6-dioxopiperidin-3-yl)-1-oxoisoindolin-5-yl)methyl)acetamide;

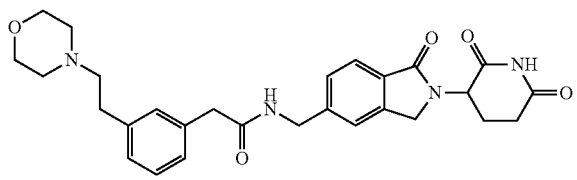

N-((2-(2,6-dioxopiperidin-3-yl)-1-oxoisoindolin-5-yl)methyl)-2-(3-(2-morpholinoethyl)phenyl)acetamide;

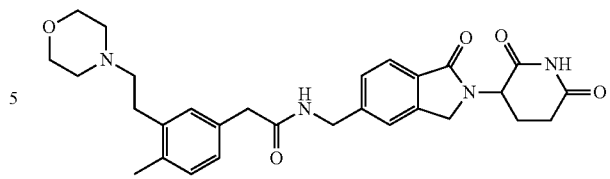

N-((2-(2,6-dioxopiperidin-3-yl)-1-oxoisoindolin-5-yl)methyl)-2-(4-methyl-3-(2-morpholinoethyl)phenyl)acetamide;

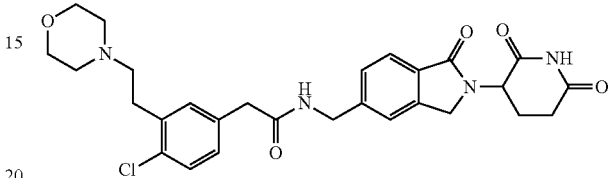

2-(4-chloro-3-(2-morpholinoethyl)phenyl)-N-((2-(2,6-dioxopiperidin-3-yl)-1-oxoisoindolin-5-yl)methyl)acetamide;

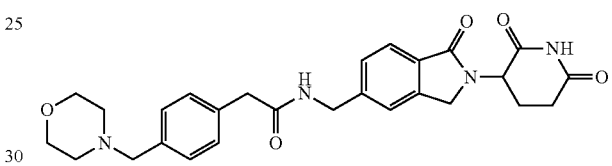

N-((2-(2,6-dioxopiperidin-3-yl)-1-oxoisoindolin-5-yl)methyl)-2-(4-(morpholinomethyl)phenyl)acetamide;

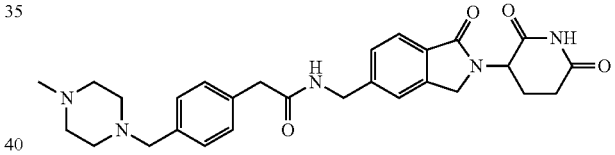

N-((2-(2,6-dioxopiperidin-3-yl)-1-oxoisoindolin-5-yl)methyl)-2-(4-((4-methylpiperazin-1-yl)methyl)phenyl)acetamide;

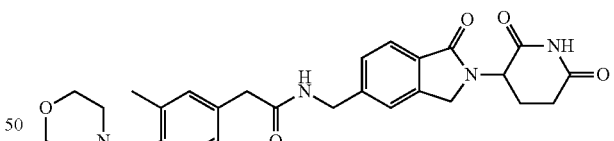

N-((2-(2,6-dioxopiperidin-3-yl)-1-oxoisoindolin-5-yl)methyl)-2-(3-methyl-4-(morpholinomethyl)phenyl)acetamide;

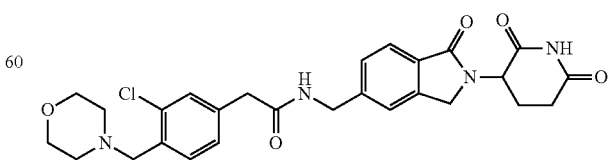

2-(3-chloro-4-(morpholinomethyl)phenyl)-N-((2-(2,6-dioxopiperidin-3-yl)-1-oxoisoindolin-5-yl)methyl)acetamide;

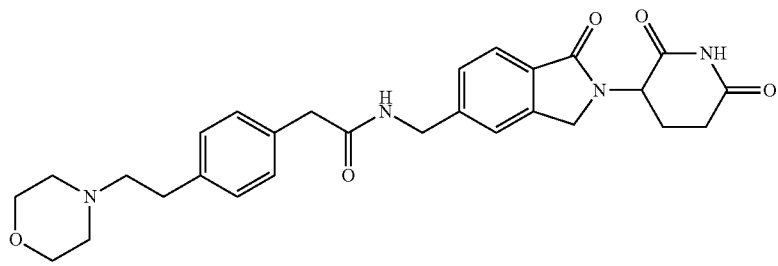
N-((2-(2,6-dioxopiperidin-3-yl)-1-oxoisoindolin-5-yl)methyl)-2-(4-(2-morpholinoethyl)phenyl)acetamide;
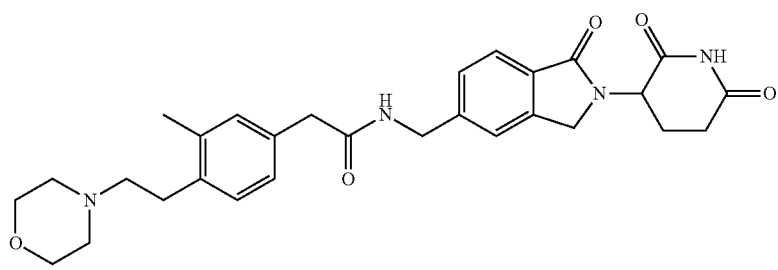
N-((2-(2,6-dioxopiperidin-3-yl)-1-oxoisoindolin-5-yl)methyl)-2-(3-methyl-4-(2-morpholinoethyl)phenyl)acetamide;
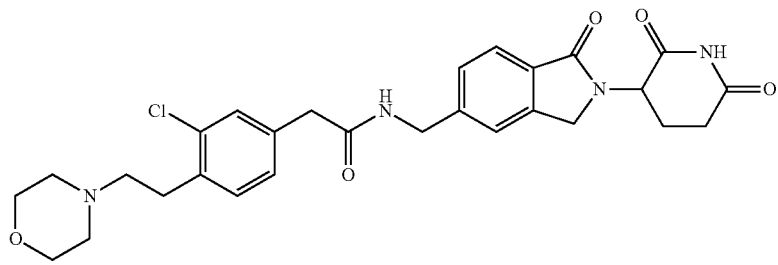
2-(3-chloro-4-(2-morpholinoethyl)phenyl)-N-((2-(2,6-dioxopiperidin-3-yl)-1-oxoisoindolin-5-yl)methyl)acetamide;
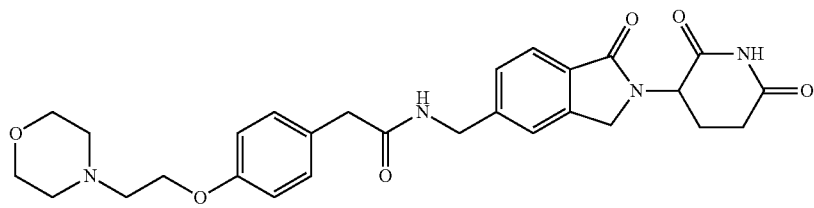
N-((2-(2,6-dioxopiperidin-3-yl)-1-oxoisoindolin-5-yl)methyl)-2-(4-(2-morpholinoethoxy)phenyl)acetamide;

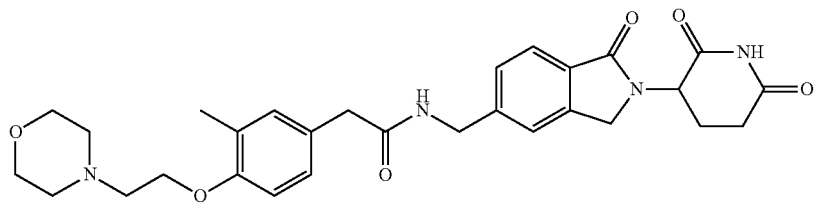

N-((2-(2,6-dioxopiperidin-3-yl)-1-oxoisoindolin-5-yl)
methyl)-2-(3-methyl-4-(2-morpholinoethoxy)phenyl)aceta-
mide;

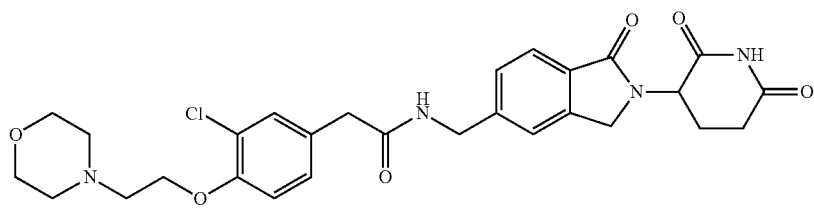

2-(3-chloro-4-(2-morpholinoethoxy)phenyl)-N-((2-(2,6-
dioxopiperidin-3-yl)-1-oxoisoindolin-5-yl)methyl)aceta-
mide;

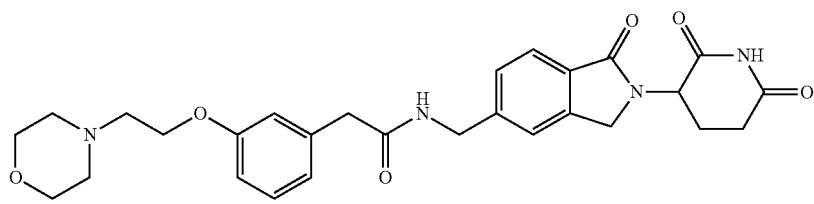

N-((2-(2,6-dioxopiperidin-3-yl)-1-oxoisoindolin-5-yl)
methyl)-2-(3-(2-morpholinoethoxy)phenyl)acetamide;

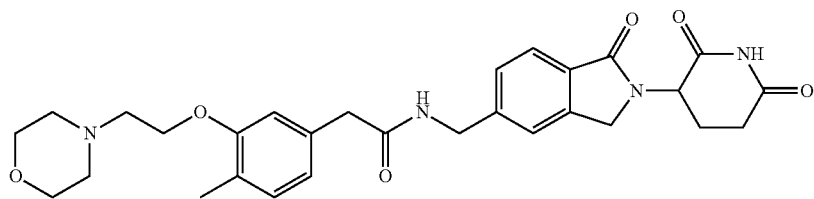

N-((2-(2,6-dioxopiperidin-3-yl)-1-oxoisoindolin-5-yl)
methyl)-2-(4-methyl-3-(2-morpholinoethoxy)phenyl)aceta-
mide;

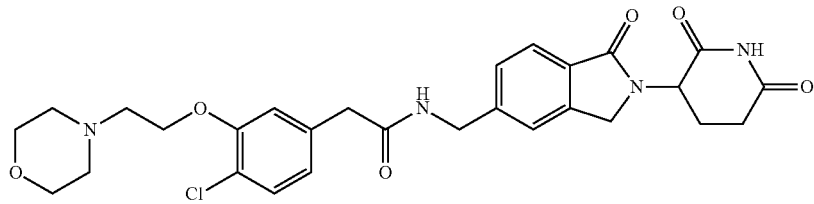

2-(4-chloro-3-(2-morpholinoethoxy)phenyl)-N-((2-(2,6-
dioxopiperidin-3-yl)-1-oxoisoindolin-5-yl)methyl)aceta-
mide;

121

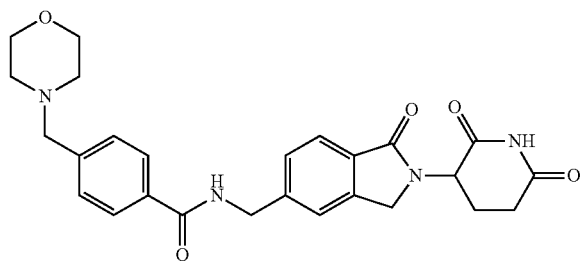

N-((2-(2,6-dioxopiperidin-3-yl)-1-oxoisoindolin-5-yl)methyl)-4-(morpholinomethyl)benzamide;

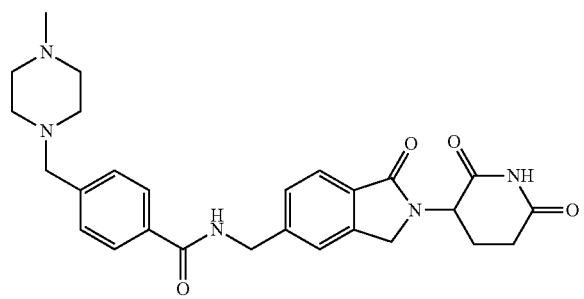

N-((2-(2,6-dioxopiperidin-3-yl)-1-oxoisoindolin-5-yl)methyl)-4-((4-methylpiperazin-1-yl)methyl)benzamide;

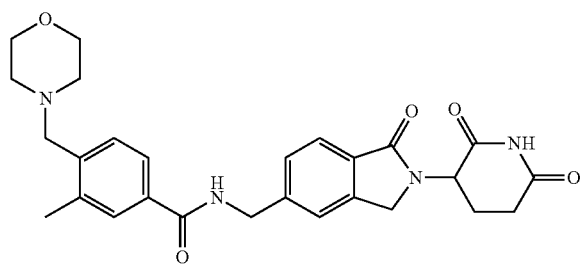

N-((2-(2,6-dioxopiperidin-3-yl)-1-oxoisoindolin-5-yl)methyl)-3-methyl-4-(morpholinomethyl)benzamide;

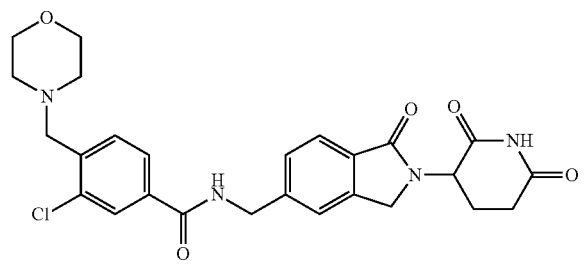

3-chloro-N-((2-(2,6-dioxopiperidin-3-yl)-1-oxoisoindolin-5-yl)methyl)-4-(morpholinomethyl)benzamide;

122

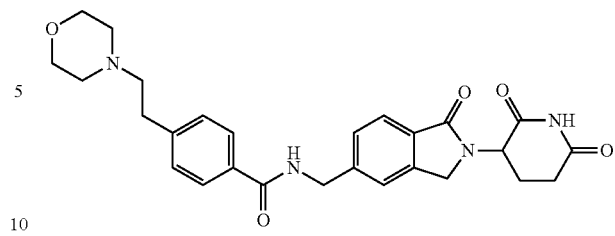

N-((2-(2,6-dioxopiperidin-3-yl)-1-oxoisoindolin-5-yl)methyl)-4-(2-morpholinoethyl)benzamide;

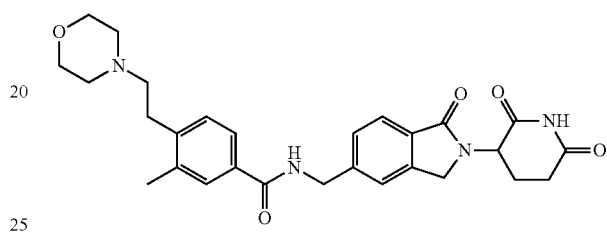

N-((2-(2,6-dioxopiperidin-3-yl)-1-oxoisoindolin-5-yl)methyl)-3-methyl-4-(2-morpholinoethyl)benzamide;

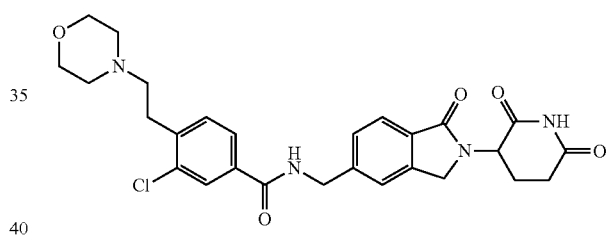

3-chloro-N-((2-(2,6-dioxopiperidin-3-yl)-1-oxoisoindolin-5-yl)methyl)-4-(2-morpholinoethyl)benzamide;

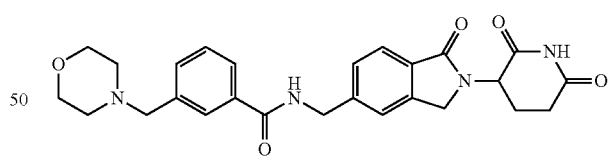

N-((2-(2,6-dioxopiperidin-3-yl)-1-oxoisoindolin-5-yl)methyl)-3-(morpholinomethyl)benzamide;

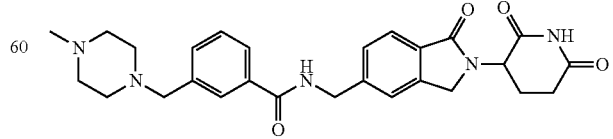

N-((2-(2,6-dioxopiperidin-3-yl)-1-oxoisoindolin-5-yl)methyl)-3-((4-methylpiperazin-1-yl)methyl)benzamide;

123

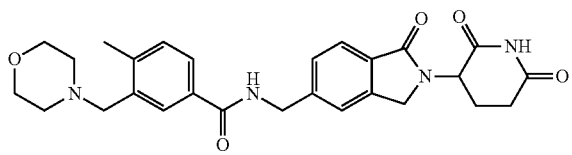

N-((2-(2,6-dioxopiperidin-3-yl)-1-oxoisoindolin-5-yl)
methyl)-4-methyl-3-(morpholinomethyl)benzamide;

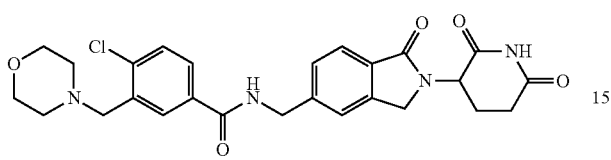

4-chloro-N-((2-(2,6-dioxopiperidin-3-yl)-1-oxoisoindo-
lin-5-yl)methyl)-3-(morpholinomethyl)benzamide;

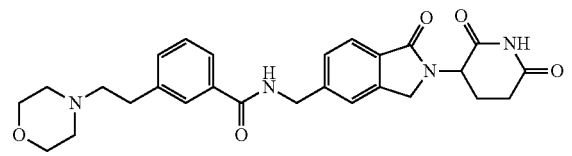

N-((2-(2,6-dioxopiperidin-3-yl)-1-oxoisoindolin-5-yl)
methyl)-3-(2-morpholinoethyl)benzamide;

124

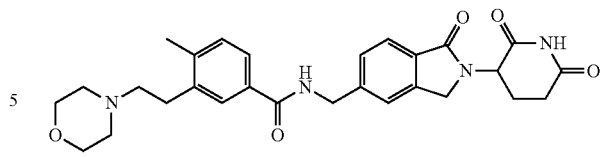

N-((2-(2,6-dioxopiperidin-3-yl)-1-oxoisoindolin-5-yl)
methyl)-4-methyl-3-(2-morpholinoethyl)benzamide;

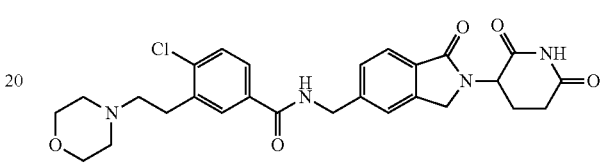

4-chloro-N-((2-(2,6-dioxopiperidin-3-yl)-1-oxoisoindo-
lin-5-yl)methyl)-3-(2-morpholinoethyl)benzamide;

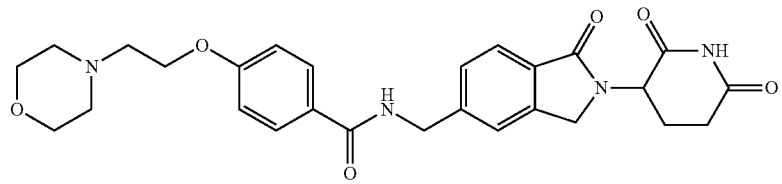

N-((2-(2,6-dioxopiperidin-3-yl)-1-oxoisoindolin-5-yl)
methyl)-4-(2-morpholinoethoxy)benzamide;

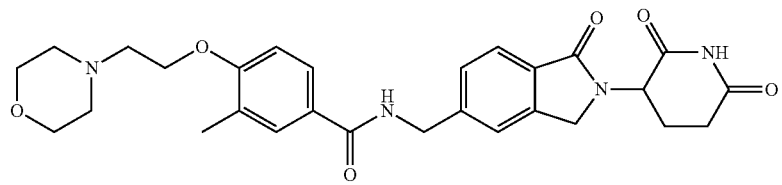

N-((2-(2,6-dioxopiperidin-3-yl)-1-oxoisoindolin-5-yl)
methyl)-3-methyl-4-(2-morpholinoethoxy)benzamide;

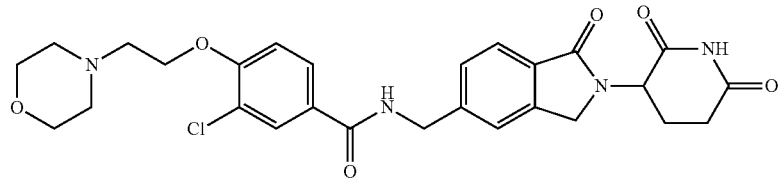

3-chloro-N-((2-(2,6-dioxopiperidin-3-yl)-1-oxoisoindo-
lin-5-yl)methyl)-4-(2-morpholinoethoxy)benzamide;

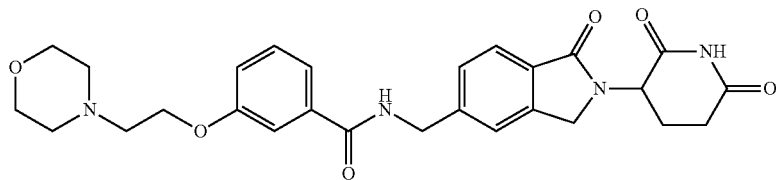

N-((2-(2,6-dioxopiperidin-3-yl)-1-oxoisoindolin-5-yl)methyl)-3-(2-morpholinoethoxy)benzamide;

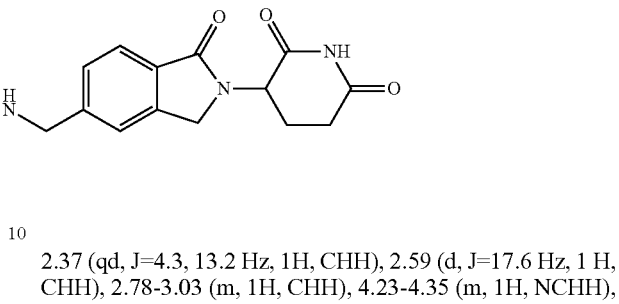

N-((2-(2,6-dioxopiperidin-3-yl)-1-oxoisoindolin-5-yl)methyl)-4-methyl-3-(2-morpholinoethoxy)benzamide; and

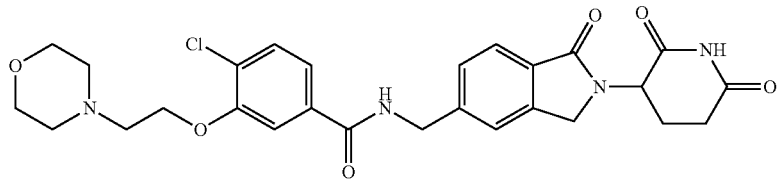

4-chloro-N-((2-(2,6-dioxopiperidin-3-yl)-1-oxoisoindolin-5-yl)methyl)-3-(2-morpholinoethoxy)benzamide.

5.57 3-[5-(6-Chloro-4-ozo-4H-quinazolin-3-ylmethyl)-1-oxo-1,3-dihydro-isoindol-2-yl]-piperidine-2,6-dione

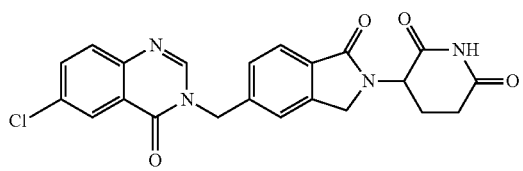

2-Amino-5-chloro-N-[2-(2,6-dioxo-piperidin-3-yl)-1-oxo-2,3-dihydro-1H-isoindol-5-ylmethyl]-benzamide (250 mg, 0.586 mmol) was suspended in trimethyl orthoformate (3 mL) and the mixture was heated to 85° C. overnight. Formic acid (100 L) was added to the reaction and the mixture was heated for 1 hr. Water was added to the reaction resulting in a white precipitate. The solid was filtered, washed with additional water, and dried in a vacuum oven to provide the product as a white solid (140 mg, 55% yield): HPLC: Waters Symmetry $C_{18}$, 5 μm, 3.9×150 mm, 1 mL/min, 240 nm, 30/70 CH$_3$CN/0.1% H$_3$PO$_4$, 7.20 min (97.9%); mp: 308-310° C.; $^1$H NMR (DMSO-d$_6$) δ 1.90-2.08 (m, 1H, CHH), 2.37 (qd, J=4.3, 13.2 Hz, 1H, CHH), 2.59 (d, J=17.6 Hz, 1 H, CHH), 2.78-3.03 (m, 1H, CHH), 4.23-4.35 (m, 1H, NCHH), 4.38-4.51 (m, 1H, NCHH), 5.10 (dd, J=5.0, 13.1 Hz, 1H, NCH), 5.33 (s, 2H, NCH$_2$), 7.52 (d, J=7.7 Hz, 1H, Ar), 7.59 (s, 1H, Ar), 7.67-7.80 (m, 2H, Ar), 7.88 (dd, J=2.5, 8.7 Hz, 1H, Ar), 8.09 (d, J=2.3 Hz, 1H, Ar), 8.66 (s, 1H, NCHN), 10.98 (s, 1H, CONH); $^{13}$C NMR (DMSO-d$_6$) δ 22.45, 31.17, 47.13, 49.20, 51.59, 122.68, 122.91, 123.23, 125.11, 127.56, 129.59, 131.14, 131.50, 134.59, 140.45, 142.59, 146.68, 148.47, 159.20, 167.63, 170.92, 172.82; LCMS: MH$^+$=437, 439; Anal. Calcd. for $C_{22}H_{17}ClN_4O_4$+0.4 H$_2$O: C, 59.51; H, 4.04; N, 12.62; 7.98, Cl; Found: C, 59.29; H, 3.66; N, 12.39; 7.82, Cl.

5.58 6-Chloro-3-[2-(2,6-dioxo-piperidin-3-yl)-1-oxo-2,3-dihydro-1H-isoindol-5-ylmethyl]-1H-quinazoline-2,4-dione To a slurry of 2-amino-5-chloro-N-[2-(2,6-dioxo-piperidin-3-yl)-1-oxo-2,3-dihydro-1H-isoindol-5-ylmethyl]-benzamide (250 mg, 0.586 mmol) in acetonitrile (5 mL) was added DIPEA (0.204 mL, 1.171 mmol), followed by phosgene (0.62 mL, 1.171 mmol). The reaction mixture was warmed up to 60° C. After 4 hrs, additional phosgene was added (0.31 mL) and stirring was continued for 1 hr, at which time LC-MS indicated reaction completion. The reaction slurry was quenched with dilute HCl, and the white solid was collected by filtration and washed with additional water and copious Et$_2$O. The cake was dried in a vacuum oven to afford the product as a white solid (185 mg, 84% yield): HPLC: Waters Symmetry C$_{18}$, 5 μm, 3.9×150 mm, 1 mL/min, 240 nm, 30/70 CH$_3$CN/0.1% H$_3$PO$_4$, 7.97 min (97.6%); mp: 358-360° C.; $^1$H NMR (DMSO-d$_6$) δ 1.88-2.07 (m, 1H, CHH), 2.24-2.45 (m, 1H, CHH), 2.53-2.68 (m, 1H, CHH), 2.79-3.01 (m, 1H, CHH), 4.17-4.36 (m, 1H, CHH), 4.36-4.54 (m, 1H, CHH), 5.09 (dd, J=4.9, 13.2 Hz, 1H, CH), 5.19 (s, 2H, PhCH$_2$), 7.24 (d, J=8.7 Hz, 1H, Ar), 7.47 (d, J=7.9 Hz, 1H, Ar), 7.54 (s, 1H, Ar), 7.68 (d, J=7.7 Hz, 1H, Ar), 7.74 (dd, J=8.8 Hz, 1H, Ar), 7.89 (d, J=2.3 Hz, 1H, Ar), 10.98 (s, 1H, NH), 11.72 (s, 1H, NH); $^{13}$C NMR (DMSO-d$_6$) δ 22.46, 31.18, 43.50, 47.12, 51.58, 115.11, 117.49, 122.29, 122.96, 126.37, 126.54, 127.29, 130.65, 135.04, 138.38, 141.17, 142.39, 149.90, 161.08, 167.79, 170.94, 172.83. LCMS: MH=453, 455; Anal. Calcd. for C$_{22}$H$_{17}$ClN$_4$O$_5$+0.3 H$_2$O: C, 57.66; H, 3.87: N, 12.23; Cl, 7.74; Found: C, 57.60; H, 3.90; N, 11.97; Cl, 7.72.

5.59 [2-(2,6-Dioxo-piperidin-3-yl)-1-oxo-2,3-dihydro-1H-isoindol-5-ylmethyl]-carbamic Acid 4-chloro-3-methyl-phenyl Ester

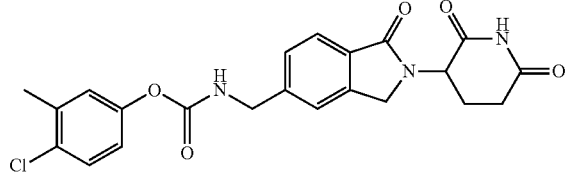

To the solution of para-nitro-phenyl chloroformate (1000 mg, 0.5 mmol) in CH$_3$CN (5 mL), was added the CH$_3$CN solution (5 mL) of 4-chloro-m-cresol (71.3 mg, 0.5 mmol) and DIPEA (0.24 mL, 1.5 mmol) dropwise at room temperature. The mixture was stirred at room temperature for 10 min. 3-(5-Aminomethyl-1-oxo-1,3-dihydro-isoindol-2-yl)-piperidine-2,6-dione methanesulfonic acid salt (0.37 g, 1 mmol) was added followed by additional DIPEA (0.24 mL, 1.5 mmol). The mixture was stirred overnight at ambient temperature. The mixture was then filtered. The resulted solid was purified on silica gel column eluted using methanol and methylene chloride to give [2-(2,6-dioxo-piperidin-3-yl)-1-oxo-2,3-dihydro-1H-isoindol-5-ylmethyl]-carbamic acid 4-chloro-3-methyl-phenyl ester as a white solid (30 mg, 14% yield). HPLC: Waters Symmetry C$_{18}$, 5 μm, 3.9×150 mm, 1 mL/min, 240 nm, 50/50, CH$_3$CN/0.1% H$_3$PO$_4$,: t$_R$=3.0 min (97%); mp 225-227° C.; $^1$H NMR (DMSO-d$_6$) δ 1.91-2.08 (m, 1H, CHH), 2.32 (s, 3H, CH$_3$), 2.40 (dd, J=4.3, 12.8 Hz, 1H, CHH), 2.63 (br. s., 1H, CHH), 2.83-3.02 (m, 1H, CHH), 4.22-4.56 (m, 4H, CH$_2$, CH$_2$), 5.12 (dd, J=5.1, 13.2 Hz, 1H, NCH), 7.01 (dd, J=2.3, 8.7 Hz, 1H, Ar), 7.17 (d, J=2.3 Hz, 1H, Ar), 7.40 (d, J=8.7 Hz, 1H, Ar), 7.46 (d, J=7.4 Hz, 1H, Ar), 7.55 (s, 1H, Ar), 7.72 (d, J=7.9 Hz, 1H, Ar), 8.47 (t, J=6.0 Hz, 1H, NH), 10.99 (s, 1H, NH). $^{13}$C NMR (DMSO-d$_6$) δ 19.52, 22.49, 31.20, 44.04, 47.15, 51.59, 121.03, 122.04, 123.04, 124.43, 127.01, 129.33, 130.58, 136.54, 142.45, 143.35, 145.35, 149.62, 154.43, 167.87, 170.99, 172.86; LC-MS: 442; Anal Calcd for C$_{22}$H$_{20}$ClN$_3$O$_6$ C, 59.80; H, 4.56; N, 9.51; Found: C, 59.74; H, 4.45; N, 9.58.

5.60 1-[1-(3,4-Dichloro-phenyl)-ethyl]-3-[2-(2,6-dioxo-piperidin-3-yl)-1-oxo-2,3-dihydro-1H-isoindol-5-ylmethyl]-urea

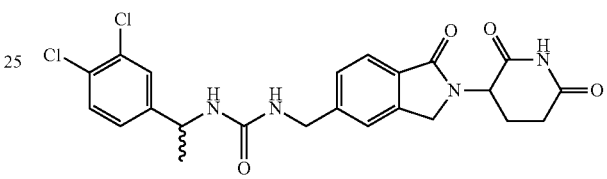

A stirred mixture of 3-(5-aminomethyl-1-oxo-1,3-dihydro-isoindol-2-yl)-piperidine-2,6-dione methane sulfonate (0.37 g, 1.00 mmol) and CDI (0.18 g, 1.10 mmol) in N,N-dimethylformamide (10 mL) was heated to 40° C. under nitrogen overnight. 1-(3,4-Dichloro-phenyl)-ethylamine (0.19 g, 1.00 mmol) was then added and the mixture was heated at 40° C. overnight. Water (60 mL) was added, solid precipitated, was filtered, washed with water (30 mL) and was purified by preparative HPLC (gradient: CH$_3$CN/H$_2$O: 10/90 for 5 min, to 100/0 in 10 min, 100/0 for 5 min). Solvent was evaporated and the residue was triturated in ether (20 mL) for 1 h. The product was then isolated by filtration and dried in vacuo to give 1-[1-(3,4-Dichloro-phenyl)-ethyl]-3-[2-(2,6-dioxo-piperidin-3-yl)-1-oxo-2,3-dihydro-1H-isoindol-5-ylmethyl]-urea as a white solid (0.084 g, 17% yield): HPLC: Waters Symmetry C$_{18}$, 5 μm, 3.9×150 mm, 1 mL/min, 240 nm, gradient: CH$_3$CN/0.1% H$_3$PO$_4$: 10/90 to 90/10 in 10 min, 90/10 (5 min); 8.57 min (96.68%); mp: 200-202° C.; $^1$H NMR (DMSO-d$_6$) δ 1.32 (d, J=7.0 Hz, 3H, CH$_3$), 1.88-2.13 (m, 1H, CHH), 2.28-2.47 (m, 1H, CHH), 2.55-2.70 (m, 1H, CHH), 2.79-3.04 (m, 1H, CHH), 4.18-4.55 (m, 4H, CH$_2$, CH$_2$), 4.74 (quin, J=7.0 Hz, 1H, CH), 5.11 (dd, J=4.9, 13.2 Hz, 1H, CH), 6.51 (s, 1H, NH), 6.66 (d, J=7.9 Hz, 1H, NH), 7.20-7.46 (m, 3H, Ar), 7.48-7.62 (m, 2H, Ar), 7.65 (d, J=7.7 Hz, 1H, Ar), 10.99 (s, 1H, NH); $^{13}$C NMR (DMSO-d$_6$) δ 22.51, 22.80, 31.20, 42.86, 47.07, 48.18, 51.55, 121.61, 122.81, 126.28, 126.70, 127.78, 128.79, 130.14, 130.38, 130.77, 142.26, 145.29, 147.41, 157.20, 167.95, 170.98, 172.85; LCMS: MH=489, 491; Anal Calcd for C$_{23}$H$_{22}$N$_4$O$_4$Cl$_2$+0.9 H$_2$O: C, 54.64, H, 4.75, N, 11.08; Found: C, 54.27, H, 4.66, N, 10.98.

5.61 1-(3-Chloro-4-(2-(2-methoxyethoxy)ethoxy)phenyl)-3-((2-(2,6-dioxopiperidin-3-yl)-1-oxoisoindolin-5-yl)methyl)urea

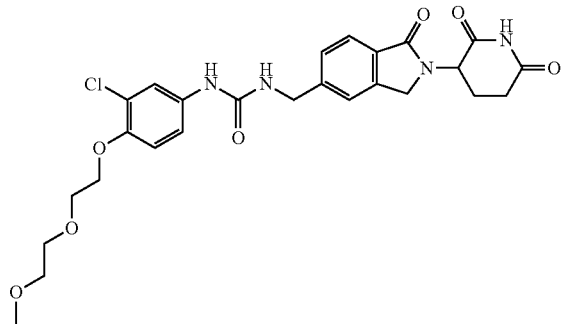

3-(5-aminomethyl-1-oxo-1,3-dihydro-isoindol-2-yl)-piperidine-2,6-dione methanesulfonate (1.11 g, 3.0 mmol) and 1,1'-Carbonyldiimidazole (535 mg, 3.3 mmol) were suspended in dry DMF (20 mL) and the mixture was stirred at rt for 24 h. While stirring, a portion of the reaction mixture (6.7 mL, ~1 mmol) was transferred to a vial containing 3-chloro-4-(2-(2-methoxyethoxy)ethoxy)aniline hydrochloride (310 mg, 1.1 mmol). The resulting mixture was stirred at rt overnight and the reaction progress was monitored by LCMS. After 48 h, additional 3-chloro-4-(2-(2-methoxyethoxy)ethoxy)aniline hydrochloride (56 mg, 0.2 mmol) was transferred to the reaction mixture and stirring continued for another 24 h. The reaction mixture was acidified with 1 N HCl and water was added with stirring until a precipitate formed. The solid was collected by filtration, suction dried, then dissolved in DMF and purified using C-18 preparatory HPLC to give 1-(3-chloro-4-(2-(2-methoxyethoxy)ethoxy)phenyl)-3-((2-(2,6-dioxopiperidin-3-yl)-1-oxoisoindolin-5-yl)methyl) urea as a white solid (390 mg, 72% yield): HPLC: Waters Symmetry $C_{18}$, 5 µm, 3.9×150 mm, 1 ml/min, 240 nm, 30/70 $CH_3CN/0.1\%$ $H_3PO_4$, 5.40 min (99.8%); mp: 188-190° C.; $^1H$ NMR (DMSO-$d_6$) δ 1.92-2.10 (m, 1H, CHH), 2.29-2.47 (m, 1H, CHH), 2.60 (dd, J=2.2, 15.4 Hz, 1H, CHH), 2.82-3.01 (m, 1H, CHH), 3.25 (s, 3H, $CH_3$), 3.46 (dd, J=3.7, 5.6 Hz, 2H, $CH_2$), 3.61 (dd, J=3.8, 5.7 Hz, 2H, $CH_2$), 3.73 (d, J=4.7 Hz, 2H, $CH_2$), 4.09 (t, J=4.9 Hz, 2H, $CH_2$), 4.24-4.55 (m, 4H, $CH_2$, $CH_2$), 5.11 (dd, J=5.1, 13.2 Hz, 1H, CH), 6.77 (t, J=5.9 Hz, 1H, NH), 7.04 (d, J=9.1 Hz, 1H, Ar), 7.19 (dd, J=2.5, 9.0 Hz, 1H, Ar), 7.38-7.49 (m, 1H, Ar), 7.51 (s, 1H, Ar), 7.64 (d, 2.6 Hz, 1H, Ar), 7.69 (d, J=7.7 Hz, 1H, Ar), 8.65 (s, 1H, NH), 10.98 (s, 1H, NH); $^{13}C$ NMR (DMSO-$d_6$) δ 22.51, 31.20, 42.80, 47.12, 51.56, 58.05, 68.80, 68.85, 69.84, 71.29, 114.66, 117.58, 119.49, 121.24, 121.88, 122.91, 126.89, 130.29, 134.53, 142.38, 144.84, 148.40, 155.25, 167.95, 171.01, 172.86; LCMS: MH=545, 547; Anal Calcd for $C_{26}H_{29}ClN_4O_7$+0.4 $H_2O$: C, 56.55; H, 5.44; N, 10.15. Found: C, 56.64; H, 5.34; N, 10.15.

5.62 Assays

5.62.1 TNFα Inhibition Assay in PMBC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+ human serum (Gemini Bio-products, Woodland, Calif., USA), 2 mM L-glutamine, 100 U/ml penicillin, and 100 µg/mL streptomycin (Life Technologies).

PBMC ($2\times10^5$ cells) are plated in 96-well flat-bottom Costar tissue culture plates (Corning, N.Y., USA) in triplicate. Cells are stimulated with LPS (from *Salmonella abortus* equi, Sigma cat.no. L-1887, St.Louis, Mo., USA) at 1 ng/mL final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hr before LPS stimulation. Cells are then incubated for 18-20 hrs at 37° C. in 5% $CO_2$, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

5.62.2 IL-2 and MIP-3α Production by T Cells

PBMC are depleted of adherent monocytes by placing $1\times10^8$ PBMC in 10 mL complete medium (RPMI 1640 supplemented with 10% heat-inactivated fetal bovine serum, 2 mM L-glutamine, 100 U/mL penicillin, and 100 µg/mL streptomycin) per 10 cm tissue culture dish, in 37° C., 5% $CO_2$ incubator for 30-60 min. The dish is rinsed with medium to remove all non-adherent PBMC. T cells are purified by negative selection using the following antibody (Pharmingen) and Dynabead (Dynal) mixture for every $1\times10^8$ non-adherent PBMC: 0.3 mL Sheep anti-mouse IgG heads, 15 µL anti-CD16, 15 µL anti-CD33, 15 µL anti-CD56, 0.23 mL anti-CD19 beads, 0.23 mL anti-HLA class II beads, and 56 µL anti-CD14 beads. The cells and bead/antibody mixture is rotated end-over-end for 30-60 min at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 µg/mL in PBS, 100 µL per well, incubated at 37° C. for 3-6 hrs, then washed four times with complete medium 100 µL/well just before T cells are added. Compounds are diluted to 20 times of final in a round bottom tissue culture 96-well plate. Final concentrations are about 10 µM to about 0.00064 µM. A 10 mM stock of compounds provided herein is diluted 1:50 in complete for the first 20× dilution of 200 µM in 2% DMSO and serially diluted 1:5 into 2% DMSO. Each compound is added at 10 µL per 200 µL culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3α levels are normalized to the amount produced in the presence of an amount of a compound provided herein, and $EC_{50}$s are calculated using non-linear regression, sigmoidal dose-response, constraining the top to 100% and bottom to 0%, allowing variable slope (GraphPad Prism v3.02).

5.62.3 Cell Proliferation Assay

Cell lines Namalwa, MUTZ-5, and UT-7 are obtained from the Deutsche Sammlung von Mikroorganismen and Zellkulturen GmbH (Braunschweig, Germany). The cell line KG-1 is obtained from the American Type Culture Collection (Manassas, Va., USA). Cell proliferation as indicated by $^3H$-thymidine incorporation is measured in all cell lines as follows.

Cells are plated in 96-well plates at 6,000 cells per well in media. The cells are pre-treated with compounds at about 100, 10, 1, 0.1, 0.01, 0.001, 0.0001 and 0 μM in a final concentration of about 0.25% DMSO in triplicate at 37° C. in a humidified incubator at 5% $CO_2$ for 72 hrs. One microcurie of $^3$H-thymidine (Amersham) is then added to each well, and cells are incubated again at 37° C. in a humidified incubator at 5% $CO_2$ for 6 hrs. The cells are harvested onto UniFilter GF/C filter plates (Perkin Elmer) using a cell harvester (Tomtec), and the plates are allowed to dry overnight. Microscint 20 (Packard) (25 μL/well) is added, and plates are analyzed in TopCount NXT (Packard). Each well is counted for one min. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope, (GraphPad Prism v3.02).

5.62.4 Immunoprecipitation and Immunoblot

Namalwa cells are treated with DMSO or an amount of a compound provided herein for 1 hr, then stimulated with 10 U/mL of Epo (R&D Systems) for 30 min. Cell lysates are prepared and either immunoprecipitated with Epo receptor Ab or separated immediately by SDS-PAGE. Immunoblots are probed with Akt, phospo-Akt (Ser473 or Thr308), phospho-Gab1 (Y627), Gab1, IRS2, actin, and IRF-1 Abs and analyzed on a Storm 860 Imager using ImageQuant software (Molecular Dynamics).

5.62.5 Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

5.62.6 Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 min. Samples are analyzed using flow cytometry.

5.62.7 Luciferase Assay

Namalwa cells are transfected with 4 μg of AP1-luciferase (Stratagene) per 1×10$^6$ cells and 3 μL Lipofectamine 2,000 (Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

5.62.8 Anti-Proliferation Assays

Day 1: The cells are seeded to 96-well plate with 50 ul/well in 10% FBS RPMI (w/Glutamine, w/o pen-strip) for overnight. The following cells are used:

Colorectal cancer cell: Colo 205 3200 cells/well; positive control irinotecan

Pancreatic cancer cell: BXPC-3 1200 cells/well; positive control gemcitabine

Prostate cancer cell: PC3 1200 cells/well; positive control docetaxel

Breast cancer cell: MDA-MB-231 2400 cells/well; positive control paclitaxel

Day 2: The compounds are serially diluted from 0.00001 μm~10 μm (or 0.000001~1 μM) with 50 μl/well (of 2×) and added to the plates in duplicate with relative positive control. The plates were then incubated at 37° C. for 72 hours.

Day 5: The results are detected by CellTiter Glo method. 100 μl/well of CellTiter Glo reagent is added to the plates and incubated for 10 minutes at room temperature, and then analyzed on the Top Count reader. The $IC_{50}$ of each compound is typically based on the result of two or more individually experiments.

5.63 TNFα Inhibition

The properties of certain compounds provided herein in ibhibiting TNFα were assessed using procedures substantially similar to those described in Section 6.62.1 above. Tested compounds included: 1-[2-(2,6-dioxo-piperidin-3-yl)-1-oxo-2,3-dihydro-1H-isoindol-5-ylmethyl]-3-(4-pyridin-4-ylmethyl-phenyl)-urea; 1[2-(2,6-dioxo-piperidin-3-yl)-1-oxo-2,3-dihydro-1H-isoindol-5-ylmethyl]-3-(4-hydroxymethyl-phenyl)-urea; 1-[2-(2,6-dioxo-piperidin-3-yl)-1-oxo-2,3-dihydro-1H-isoindol-5-ylmethyl]-3-[3-(2-methyl-2H-pyrazol-3-yl)-phenyl]-urea; 1-[2-(2,6-dioxo-piperidin-3-yl)-1-oxo-2,3-dihydro-1H-isoindol-5-ylmethyl]-3-[3-(2-methyl-imidazol-1-yl)-phenyl]-urea; 1-[2-(2,6-dioxo-piperidin-3-yl)-1-oxo-2,3-dihydro-1H-isoindol-5-ylmethyl]-3-[4-(4-methyl-4H-[1,2,4]triazol-3-yl)-phenyl]-urea; 1-[2-(2,6-dioxo-piperidin-3-yl)-1-oxo-2,3-dihydro-1H-isoindol-5-ylmethyl]-3-[3-(2-methyl-thiazol-4-yl)-phenyl]-urea; 1-[2-(2,6-dioxo-piperidin-3-yl)-1-oxo-2,3-dihydro-1H-isoindol-5-ylmethyl]-3-[3-(1-methyl-1H-pyrazol-3-yl)-phenyl]-urea; 1-((2-(2,6-dioxopiperidin-3-yl)-1-oxoisoindolin-5-yl)methyl)-3-(3-(morpholinomethyl)phenyl)urea; 1-((2-(2,6-dioxopiperidin-3-yl)-1-oxoisoindolin-5-yl)methyl)-3-(4-methyl-3-nitrophenyl)urea; 1-(3-amino-4-methylphenyl)-3-((2-(2,6-dioxopiperidin-3-yl)-1-oxoisoindolin-5-yl)methyl)urea; 1-[2-(2,6-dioxopiperidin-3-yl)-1-oxo-2,3-dihydro-1H-isoindol-5-ylmethyl]-3-(3-phenoxy-phenyl)-urea; 1-((2-(2,6-dioxopiperidin-3-yl)-1-oxoisoindolin-5-yl)methyl)-3-(4-nitrophenyl)urea; N-(4-{3-[2-(2,6-dioxopiperidin-3-yl)-1-oxo-2,3-dihydro-1H-isoindol-5-ylmethyl]-ureido}-phenyl)-acetamide; 1-((2-(2,6-dioxopiperidin-3-yl)-1-oxoisoindolin-5-yl)methyl)-3-(3-hydroxy-4-methylphenyl)urea; 1-[3-(1H-benzoimidazol-2-yl)-4-chloro-phenyl]-3-[2-(2,6-dioxo-piperidin-3-yl)-1-oxo-2,3-dihydro-1H-isoindol-5-ylmethyl]-urea; 1-(4-tert-butyl-cyclohexyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-cyclohexyl)-urea; 1-(6-chloro-pyridin-3-yl)-3-[2-(2,6-dioxopiperidin-3-yl)-1-oxo-2,3-dihydro-1H-isoindol-5-ylmethyl]-urea; 1-[4-(2,4-difluoro-phenyl)-thiazol-2-yl]-3-[2-(2,6-dioxo-piperidin-3-yl)-1-oxo-2,3-dihydro-1H-isoindol-5-ylmethyl]-urea; and 2,2-dimethyl-propionic acid 3-{5[3-(3-chloro-4-methyl-phenyl)-ureidomethyl]-1-oxo-1,3-dihydro-isoindol-2-yl}-2,6-dioxo-piperidin-1-ylmethyl ester. The $IC_{50}$ values for all of the tested compounds were determined to be in the range of about 0.2 to 300 nM.

5.64 Antiproliferation—Namalwa

The antiproliferation of certain compounds provided herein were assessed using Namalwa cells by following procedures substantially similar to those described in Section 5.62.3 above. The tested compounds included: 1-[2-(2,6-dioxo-piperidin-3-yl)-1-oxo-2,3-dihydro-1H-isoindol-5-ylmethyl]-3-(4-pyridin-4-ylmethyl-phenyl)-urea; 1-[2-(2,6-dioxo-piperidin-3-yl)-1-oxo-2,3-dihydro-1H-isoindol-5-ylmethyl]-3-(4-hydroxymethyl-phenyl)-urea; 1-[2-(2,6-dioxo-piperidin-3-yl)-1-oxo-2,3-dihydro-1H-isoindol-5-ylmethyl]-3-[3-(2-methyl-2H-pyrazol-3-yl)-phenyl]-urea; 1-[2-(2,6-dioxo-piperidin-3-yl)-1-oxo-2,3-dihydro-1H-isoindol-5-ylmethyl]-3-[3-(2-methyl-imidazol-1-yl)-phenyl]-urea; 1-[2-(2,6-dioxo-piperidin-3-yl)-1-oxo-2,3-dihydro-1H-isoindol-5-ylmethyl]-3-[3-(2-methyl-thiazol-4-yl)-phenyl]-urea; 1-[2-(2,6-dioxo-piperidin-3-yl)-1-oxo-2,3-dihydro-1H-isoindol-5-ylmethyl]-3-[3-(1-methyl-1H-pyrazol-3-yl)-phenyl]-urea; 1-((2-(2,6-dioxopiperidin-3-yl)-1-oxoisoindolin-5-yl)methyl)-3-(3-(morpholinomethyl)phenyl)urea; 1-((2-(2,6-dioxopiperidin-3-yl)-1-oxoisoindolin-5-yl)methyl)-3-(4-methyl-3-nitrophenyl)urea; 1-(3-amino-4-methylphenyl)-3-((2-(2,6-dioxopiperidin-3-yl)-1-oxoisoindolin-5-yl)methyl)urea; 1-[2-(2,6-dioxo-piperidin-3-yl)-1-oxo-2,3-dihydro-1H-isoindol-5-ylmethyl]-3-(3-phenoxy-phenyl)-urea; 1-((2-(2,6-dioxopiperidin-3-yl)-1-oxoisoindolin-5-yl)methyl)-3-(4-nitrophenyl)urea; 1-[2-(2,6-dioxo-piperidin-3-yl)-1-oxo-2,3-dihydro-1H-isoindol-5-ylmethyl]-3-[3-(3-methyl-[1,2,4]oxadiazol-5-yl)-phenyl]-urea; 1-(4-tert-butyl-cyclohexyl)-3-[2-(2,6-dioxo-piperidin-3-yl)-1-oxo-2,3-dihydro-1H-isoindol-5-ylmethyl]urea; 1-[2-(2,6-dioxo-piperidin-3-yl)-1-oxo-2,3-dihydro-1H-isoindol-5-ylmethyl]-3-(4-methyl-cyclohexyl)-urea; and 2,2-dimethyl-propionic acid 3-{5-[3-(3-chloro-4-methyl-phenyl)-ureidomethyl]-1-oxo-1,3-dihydro-isoindol-2-yl}-2,6-dioxo-piperidin-1-ylmethyl ester. The $IC_{50}$ values for all of the tested compounds were determined to be in the range of about 0.02 to 40 nM.

5.65 Antiproliferation—PC3

The antiproliferation of certain compounds provided herein were assessed using PC3 cells by following procedures substantially similar to those described in Section 5.62.8 above. The tested compounds included: 1-[2-(2,6-dioxo-piperidin-3-yl)-1-oxo-2,3-dihydro-1H-isoindol-5-ylmethyl]-3-(4-pyridin4-ylmethyl-phenyl)-urea; 1-[2-(2,6-dioxo-piperidin-3-yl)-1-oxo-2,3-dihydro-1H-isoindol-5-ylmethyl]-3-[3-(2-methyl-2H-pyrazol-3-yl)-phenyl]-urea: 1-[2-(2,6-dioxo-piperidin-3-yl)-1-oxo-2,3-dihydro-1H-isoindol-5-ylmethyl]-3[3-(2-methyl-thiazol-4-yl)-phenyl]-urea; 1-[2-(2,6-dioxo-piperidin-3-yl)-1-oxo-2,3-dihydro-1H-isoindol-5-ylmethyl]-3-[3-(1-methyl-1H-pyrazol-3-yl)-phenyl]-urea: 1-((2-(2,6-dioxopiperidin-3-yl)-1-oxoisoindolin-5-yl)methyl)-3-(3-(morpholinomethyl)phenyl)urea; 1-((2-(2,6-dioxopiperidin-3-yl)-1-oxoisoindolin-5-yl)methy)-3-(4-methyl-3-nitrophenyl)urea; 1-(3-amino-4-methylphenyl)-3-((2-(2,6-dioxopiperidin-3-yl)-1-oxoisoindolin-5-yl)methyl)urea; 1-[2-(2,6-dioxo-piperidin-3-yl)-1-oxo-2,3-dihydro-1H-isoindol-5-ylmethyl]-3-(3-phenoxy-phenyl)-urea; 1-((2-(2,6-dioxopiperidin-3-yl)-1-oxoisoindolin-5-yl)methyl)-3-(4-nitrophenyl)urea; 1-((2-(2,6-dioxopiperidin-3-yl)-1-oxoisoindolin-5-yl)methyl)-3-(3-hydroxy-4-methylphenyl)urea; 1-[3-(1H-benzoimidazol-2-yl)-4-chloro-phenyl]-3-[2-(2,6-dioxo-piperidin-3-yl)-1-oxo-2,3-dihydro-1H-isoindol-5-ylmethyl]-urea; 1-(4-tert-butyl-cyclohexyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-cyclohexyl)-urea; 1-(6-chloro-pyridin-3-yl)-3-[2-(2,6-dioxo-piperidin-3-yl)-1-oxo-2,3-dihydro-1H-isoindol-5-ylmethyl]-urea; 1-[4-(2,4-difluoro-phenyl)-thiazol-2-yl]-3-[2-(2,6-dioxo-piperidin-3-yl)-1-oxo-2,3-dihydro-1H-isoindol-5-ylmethyl]-urea; 2,2-dimethyl-propionic acid 3-{5-[3-(3-chloro-4-methyl-phenyl)-ureidomethyl]-1-oxo-1,3-dihydro-isoindol-2-yl}-2,6-dioxo-piperidin-1-ylmethyl ester; and 1-[1-(3,4-dichloro-phenyl)-ethyl]-3-[2-(2,6-dioxo-piperidin-3-yl)-1-oxo-2,3-dihydro-1H-isoindol-5-ylmethyl]-urea. The $IC_{50}$ values for all of the tested compounds were determined to be in the range of about 0.001 to 0.74 µM.

5.66 Antiproliferation—BxPC3

The antiproliferation of certain compounds provided herein were assessed using BxPC3 cells by following procedures substantially similar to those described in Section 5.62.8 above. The tested compounds included: 1-[2-(2,6-dioxo-piperidin-3-yl)-1-oxo-2,3-dihydro-1H-isoindol-5-ylmethyl]-3-(4-pyridin-4-ylmethyl-phenyl)-urea; 1-[2-(2,6-dioxo-piperidin-3-yl)-1-oxo-2,3-dihydro-1H-isoindol-5-ylmethyl]-3-[3-(2-methyl-2H-pyrazol-3-yl)-phenyl]-urea; 1-[2-(2,6-dioxo-piperidin-3-yl)-1-oxo-2,3-dihydro-1H-isoindol-5-ylmethyl]-3-[3-(2-methyl-thiazol-4-yl)-phenyl]-urea; 1-[2-(2,6-dioxo-piperidin-3-yl)-1-oxo-2,3-dihydro-1H-isoindol-5-ylmethyl]-3-[3-(1-methyl-1H-pyrazol-3-yl)-phenyl]-urea; 1-((2-(2,6-dioxopiperidin-3-yl)-1-oxoisoindolin-5-yl)methyl)-3-(3-(morpholinomethyl)phenyl)urea; 1-((2-(2,6-dioxopiperidin-3-yl)-1-oxoisoindolin-5-yl)methyl)-3-(4-methyl-3-nitrophenyl)urea; 1-(3-amino-4-methylphenyl)-3-((2-(2,6-dioxopiperidin-3-yl)-1-oxoisoindolin-5-yl)methyl)urea; 1-[2-(2,6-dioxo-piperidin-3-yl)-1-oxo-2,3-dihydro-1H-isoindol-5-ylmethyl]-3-(3-phenoxy-phenyl)-urea; 1-((2-(2,6-dioxopiperidin-3-yl)-1-oxoisoindolin-5-yl)methyl)-3-(4-nitrophenyl)urea; 1-((2-(2,6-dioxopiperidin-3-yl)-1-oxoisoindolin-5-yl)methyl)-3-(3-hydroxy-4-methylphenyl)urea; 1-[3-(1H-benzoimidazol-2-yl)-4-chloro-phenyl]-3-[2-(2,6-dioxo-piperidin-3-yl)-1-oxo-2,3-dihydro-1H-isoindol-5-ylmethyl]-urea; 1-(4-tert-butyl-cyclohexyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-cyclohexyl)-urea; 1-[4-(2,4-difluoro-phenyl)-thiazol-2-yl]-3-[2-(2,6-dioxo-piperidin-3-yl)-1-oxo-2,3-dihydro-1H-isoindol-5-ylmethyl]-urea; 2,2-dimethyl-propionic acid 3-{5-[3-(3-chloro-4-methyl-phenyl)-ureidomethyl]-1-oxo-1,3-dihydro-isoindol-2-yl}-2,6-dioxo-piperidin-1-ylmethyl ester; and 1-[1-(3,4-dichloro-phenyl)-ethyl]-3-[2-(2,6-dioxo-piperidin-3-yl)-1-oxo-2,3-dihydro-1H-isoindol-5-ylmethyl]-urea.

The IC$_{50}$ values for all of the tested compounds were determined to be in the range of about 0.01 to 0.94 µM.

5.67 Antiproliferation—MDAMB321

The antiproliferation of certain compounds provided herein were assessed using MDAMB321 cells by following procedures substantially similar to those described in Section 5.62.8 above. The tested compounds included: 1-[2-(2,6-dioxo-piperidin-3-yl)-1-oxo-2,3-dihydro-1H-isoindol-5-ylmethyl]-3-(4-pyridin-4-ylmethyl-phenyl)-urea; 1-[2-(2,6-dioxo-piperidin-3-yl)-1-oxo-2,3-dihydro-1H-isoindol-5-ylmethyl]-3-[3-(2-methyl-2H-pyrazol-3-yl)-phenyl]-urea; 1-[2-(2,6-dioxo-piperidin-3-yl)-1-oxo-2,3-dihydro-1H-isoindol-5-ylmethyl]-3-[3-(2-methyl-thiazol-4-yl)-phenyl]-urea; 1-[2-(2,6-dioxo-piperidin-3-yl)-1-oxo-2,3-dihydro-1H-isoindol-5-ylmethyl]-3-[3-(1-methyl-1H-pyrazol-3-yl)-phenyl]-urea; 1-((2-(2,6-dioxopiperidin-3-yl)-1-oxoisoindolin-5-yl)methyl)-3-(3-(morpholinomethyl)phenyl)urea; 1-((2-(2,6-dioxopiperidin-3-yl)-1-oxoisoindolin-5-yl)methyl)-3-(4-methyl-3-nitrophenyl)urea; 1-(3-amino-4-methylphenyl)-3-((2-(2,6-dioxopiperidin-3-yl)-1-oxoisoindolin-5-yl)methyl)urea; 1-[2-(2,6-dioxo-piperidin-3-yl)-1-oxo-2,3-dihydro-1H-isoindol-5-ylmethyl]-3-(3-phenoxy-phenyl)-urea; 1-((2-(2,6-dioxopiperidin-3-yl)-1-oxoisoindolin-5-yl)methyl)-3-(4-nitrophenyl)urea; 1-[2-(2,6-Dioxo-piperidin-3-yl)-1-oxo-2,3-dihydro-1H-isoindol-5-ylmethyl]-3-[3-(3-methyl-[1,2,4]oxadiazol-5-yl)-phenyl]-urea; 1-((2-(2,6-dioxopiperidin-3-yl)-1-oxoisoindolin-5-yl)methyl)-3-(3-hydroxy-4-methylphenyl)urea; 1-[3-(1H-benzoimidazol-2-yl)-4-chloro-phenyl]-3-[2-(2,6-dioxo-piperidin-3-yl)-1-oxo-2,3-dihydro-1H-isoindol-5-ylmethyl]-urea; 1-(4-tert-butyl-cyclohexyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-cyclohexyl)-urea; 1-(6-chloro-pyridin-3-yl)-3-[2-(2,6-dioxo-piperidin-3-yl)-1-oxo-2,3-dihydro-1H-isoindol-5-ylmethyl]-urea; 1-[4-(2,4-difluoro-phenyl)-thiazol-2-yl]-3-[2-(2,6-dioxo-piperidin-3-yl)-1-oxo-2,3-dihydro-1H-isoindol-5-ylmethyl]-urea; 2,2-dimethyl-propionic acid 3-{5-[3-(3-chloro-4-methyl-phenyl)-ureidomethyl]-1-oxo-1,3-dihydro-isoindol-2-yl}-2,6-dioxo-piperidin-1-ylmethyl ester; and 1-[1(3,4-dichloro-phenyl)-ethyl]-3-[2-(2,6-dioxo-piperidin-3-yl)-1-oxo-2,3-dihydro-1H-isoindol-5-ylmethyl]-urea. The IC$_{50}$ values for all of the tested compounds were determined to be in the range of about 0.4 to 380 nM.

5.68 Antiproliferation—Colo205

The antiproliferation of certain compounds provided herein were assessed using Colo205 cells by following procedures substantially similar to those described in Section 5.62.8 above. The tested compounds included: 1-[2-(2,6-dioxo-piperidin-3-yl)-1-oxo-2,3-dihydro-1H-isoindol-5-ylmethyl]-3-(4-pyridin-4-ylmethyl-phenyl)-urea; 1-[2-(2,6-dioxo-piperidin-3-yl)-1-oxo-2,3-dihydro-1H-isoindol-5-ylmethyl]-3-[3-(2-methyl-2H-pyrazol-3-yl)-phenyl]-urea; 1-[2-(2,6-dioxo-piperidin-3-yl)-1-oxo-2,3-dihydro-1H-isoindol-5-ylmethyl]-3-[3-(2-methyl-thiazol-4-yl)-phenyl]-urea; 1-[2-(2,6-dioxo-piperidin-3-yl)-1-oxo-2,3-dihydro-1H-isoindol-5-ylmethyl]-3-[3-(1-methyl-1H-pyrazol-3-yl)-phenyl]-urea; 1-((2-(2,6-dioxopiperidin-3-yl)-1-oxoisoindolin-5-yl)methyl)-3-(3-(morpholinomethyl)phenyl)urea; 1-((2-(2,6-dioxopiperidin-3-yl)-1-oxoisoindolin-5-yl)methyl)-3-(4-methyl-3-nitrophenyl)urea; 1-(3-amino-4-methylphenyl)-3-((2-(2,6-dioxopiperidin-3-yl)-1-oxoisoindolin-5-yl)methyl)urea; 1-[2-(2,6-dioxo-piperidin-3-yl)-1-oxo-2,3-dihydro-1H-isoindol-5-ylmethyl]-3-(3-phenoxy-phenyl)-urea; 1((2-(2,6-dioxopiperidin-3-yl)-1-oxoisoindolin-5-yl)methyl)-3-(4-nitrophenyl)urea; 1-[2-(2,6-Dioxo-piperidin-3-yl)-1-oxo-2,3-dihydro-1H-isoindol-5-ylmethyl]-3-[3-(3-methyl-[1,2,4]oxadiazol-5-yl)-phenyl]-urea; 1-((2-(2,6-dioxopiperidin-3-yl)-1-oxoisoindolin-5-yl)methyl)-3-(3-hydroxy-4-methylphenyl)urea; 1-[3-(1H-benzoimidazol-2-yl)-4-chloro-phenyl]-3-[2-(2,6-dioxo-piperidin-3-yl)-1-oxo-2,3-dihydro-1H-isoindol-5-ylmethyl]-urea; 1-(4-tert-butyl-cyclohexyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-cyclohexyl)-urea; 1-(6-chloro-pyridin-3-yl)-3-[2-(2,6-dioxo-piperidin-3-yl)-1-oxo-2,3-dihydro-1H-isoindol-5-ylmethyl]-urea; 1-[4-(2,4-difluoro-phenyl)-thiazol-2-yl]-3-[2-(2,6-dioxo-piperidin-3-yl)-1-oxo-2,3-dihydro-1H-isoindol-5-ylmethyl]-urea; 2,2-dimethyl-propionic acid 3-{5-[3-(3-chloro-4-methyl-phenyl)-ureidomethyl]-1-oxo-1,3-dihydro-isoindol-2-yl}-2,6-dioxo-piperidin-1-ylmethyl ester; and 1-[1(3,4-dichloro-phenyl)-ethyl]-3-[2-(2,6-dioxo-piperidin-3-yl)-1-oxo-2,3-dihydro-1H-isoindol-5-ylmethyl]-urea. The IC$_{50}$ values for all of the tested compounds were determined to be in the range of about 0.15 to 130 nM.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference in their entireties as if each such publication, patent or patent application were specifically and individually indicated to be incorporated herein by reference.

What is claimed is:
1. A compound of Formula (VI):

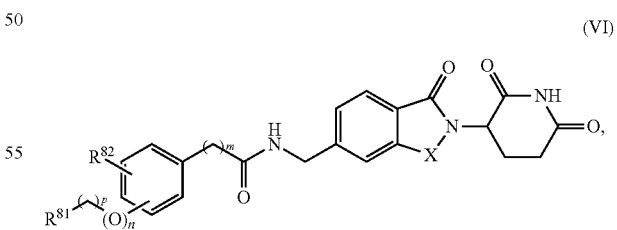

(VI)

or a pharmaceutically acceptable salt, prodrug, or stereoisomer thereof, wherein:
X is CH$_2$ or C=O;
m and n are each independently 0 or 1;
p is 0, 1, 2, or 3;
R$^{81}$ is 5 to 6 membered heterocyclyl, optionally substituted with C$_{1-6}$ alkyl; and
R$^{82}$ is hydrogen, C$_{1-6}$ alkyl, or halogen.

2. The compound of claim 1, which is:
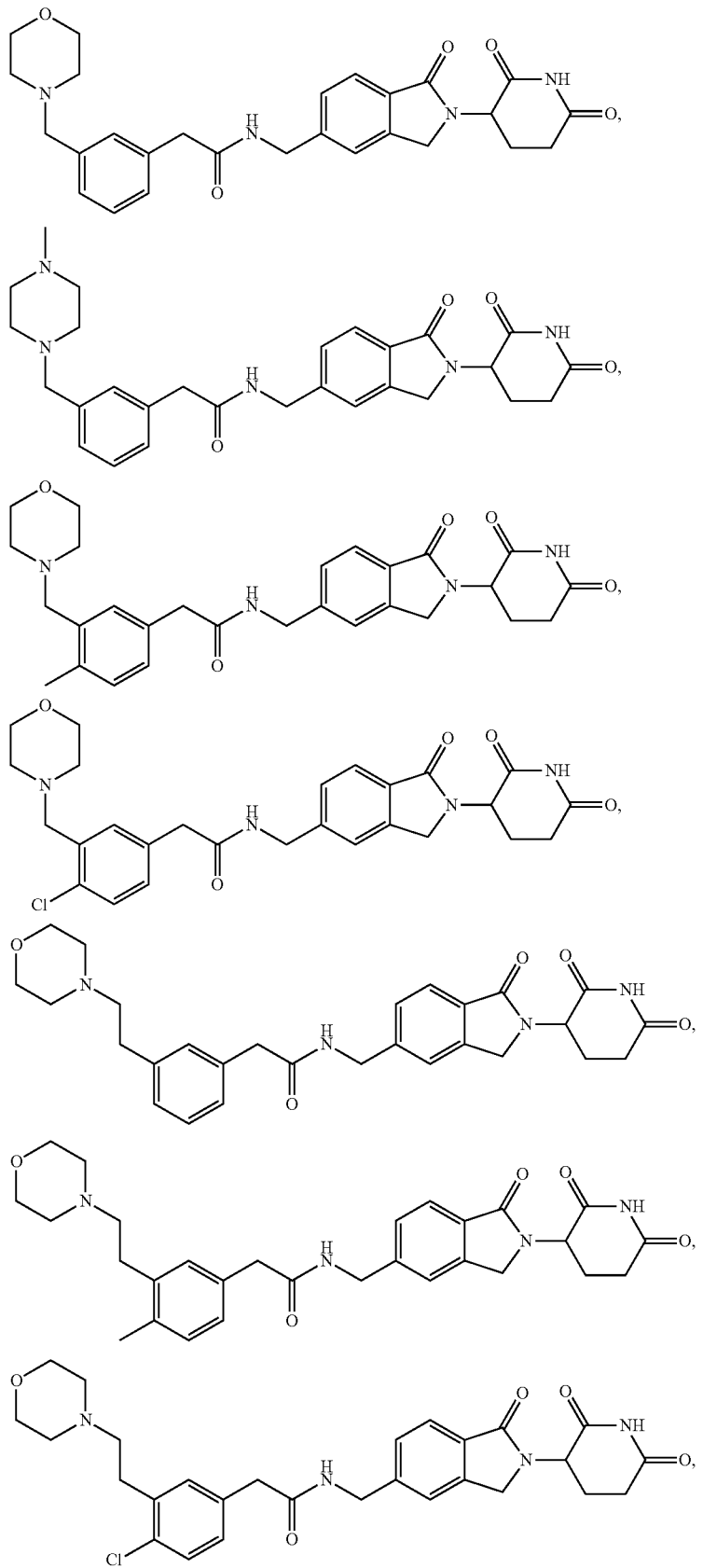

-continued
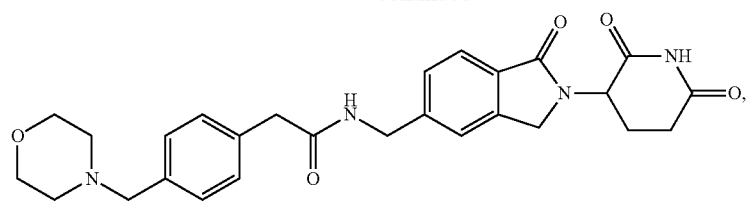
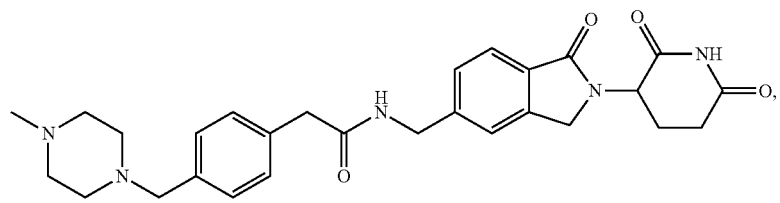
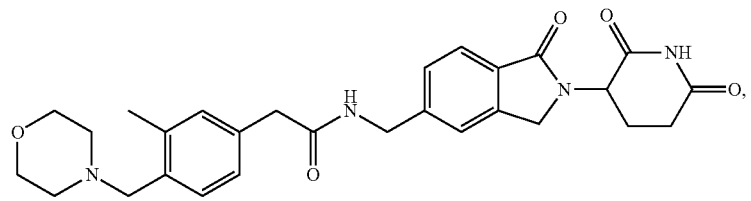
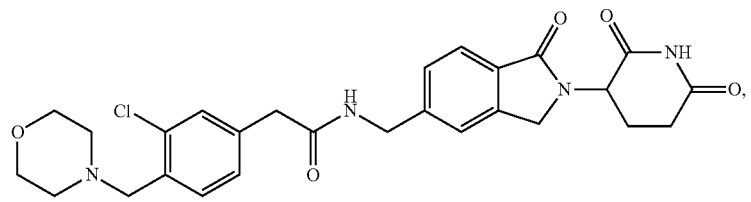
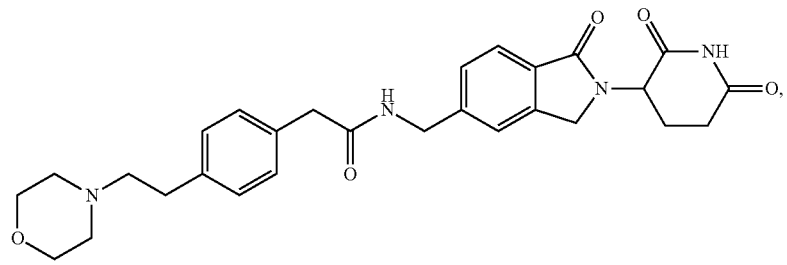
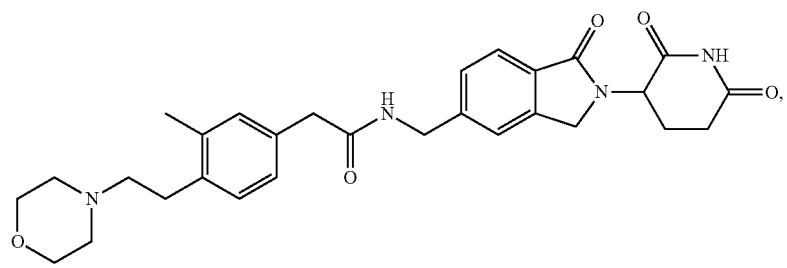
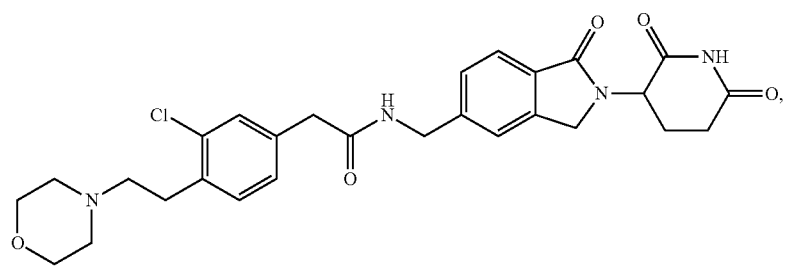

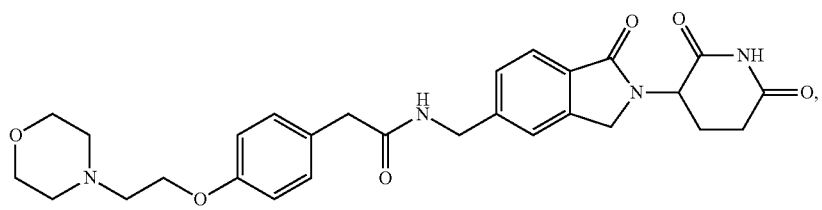
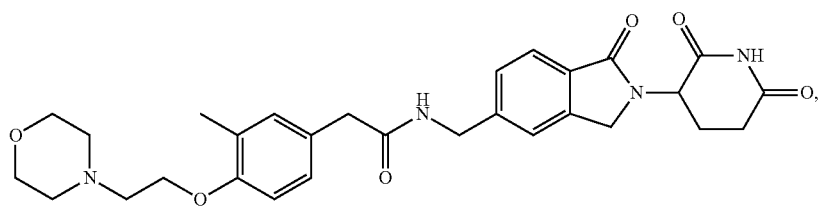
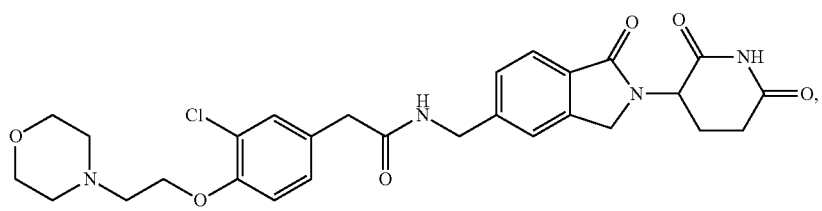
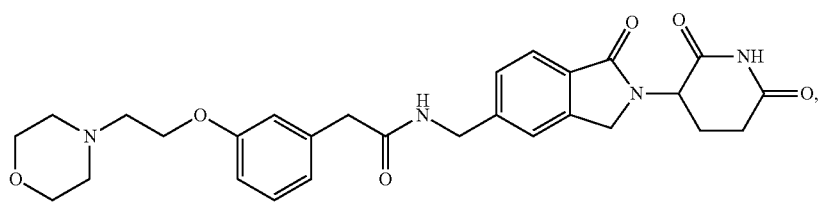
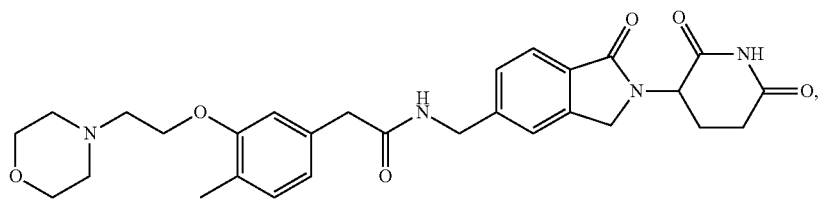
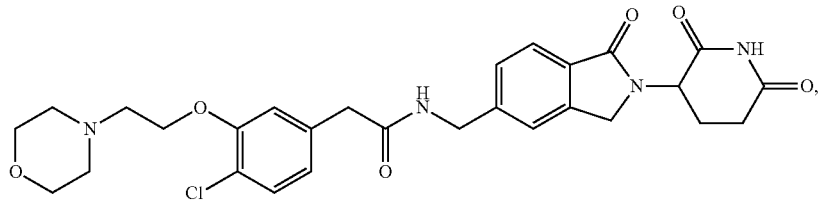
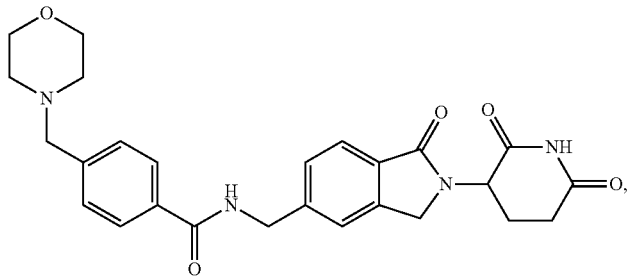

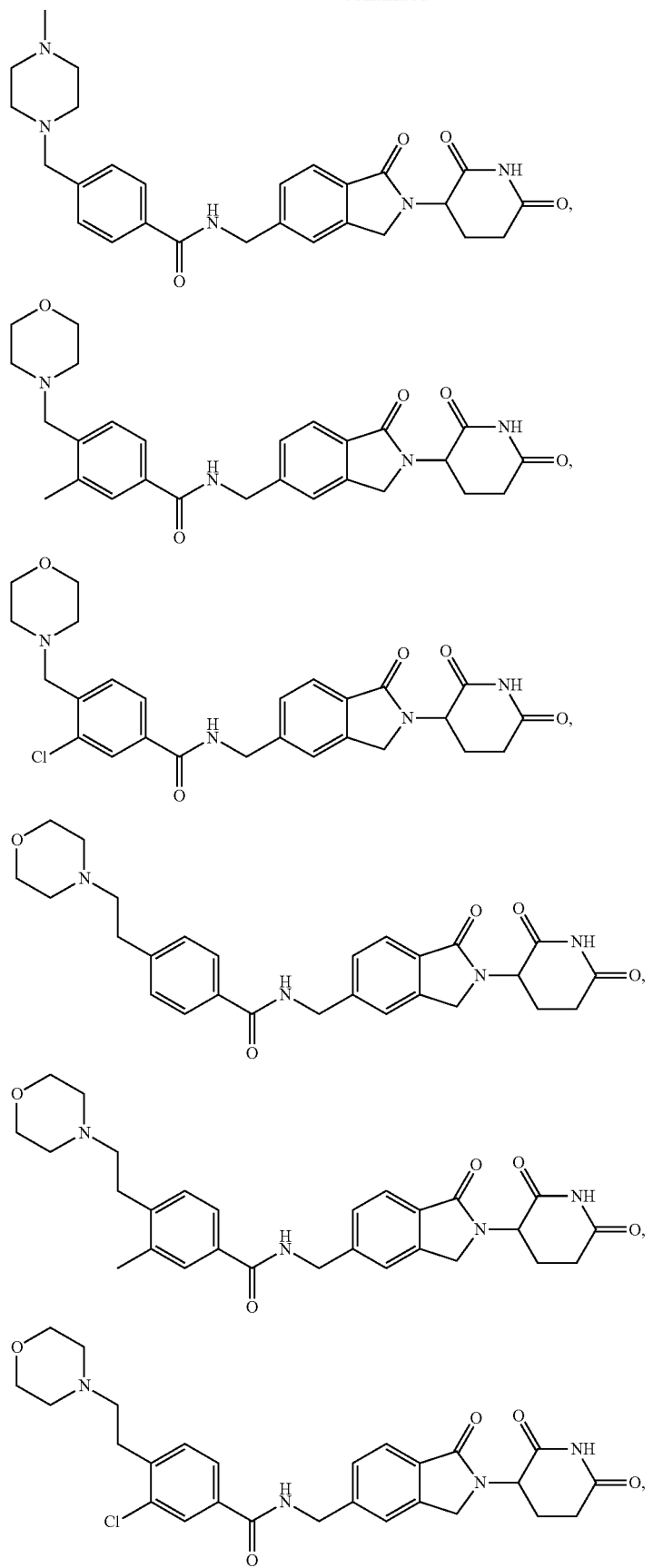

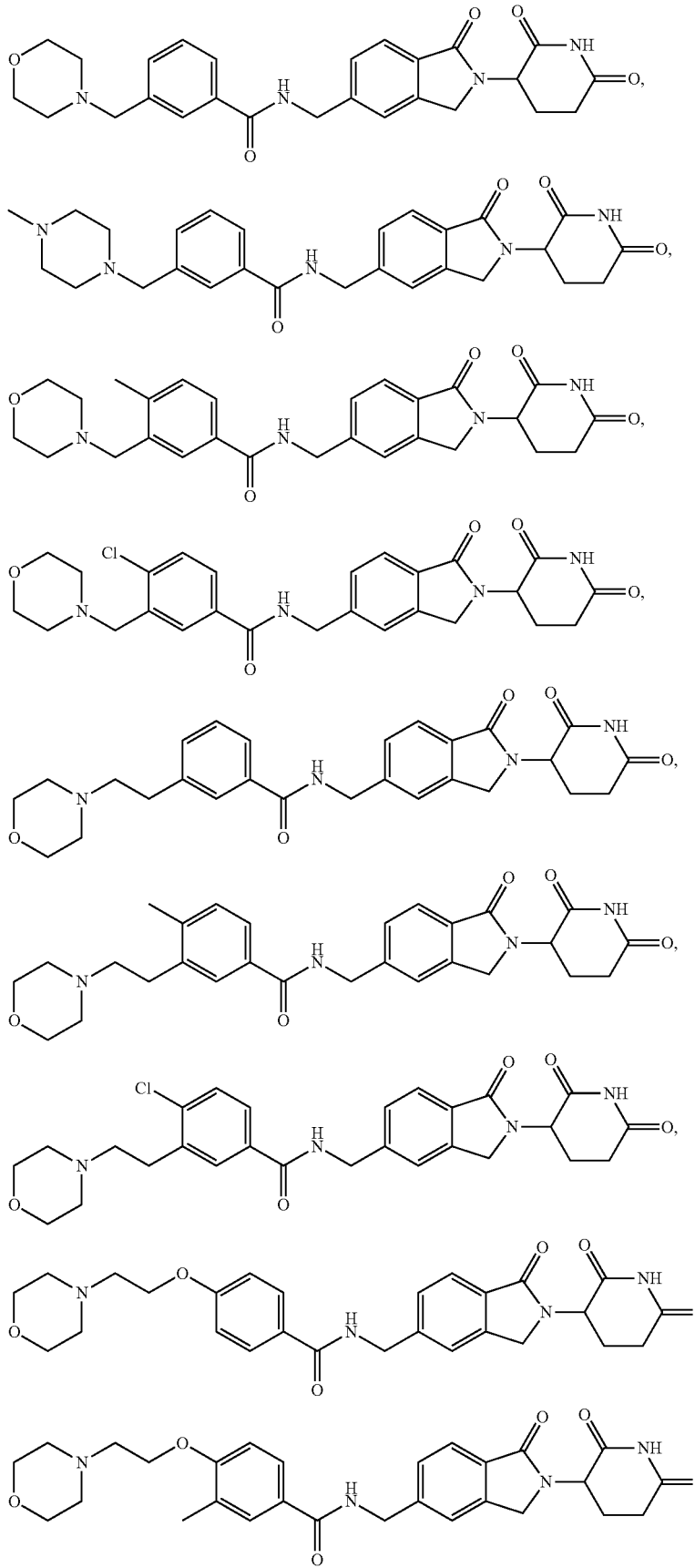

-continued

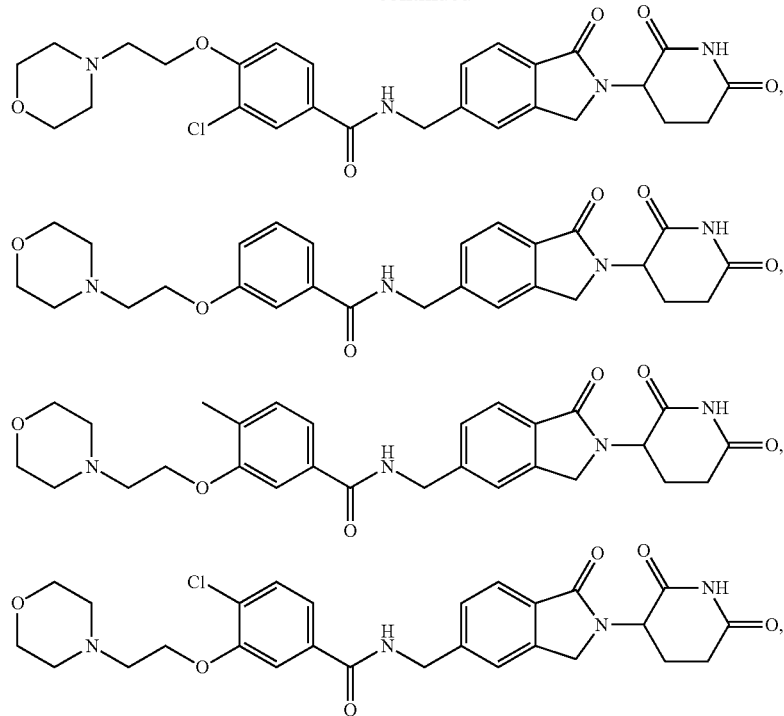

or a pharmaceutically acceptable salt, prodrug, or stereoisomer thereof.

3. A pharmaceutical composition comprising the compound of claim 1, and one or more pharmaceutically acceptable excipients or carriers.

4. The pharmaceutical composition of claim 3, further comprising a second therapeutic agent.

5. The pharmaceutical composition of claim 3, wherein the composition is formulated for single dose administration.

6. The pharmaceutical composition of claim 3, wherein the composition is formulated as oral, parenteral, or intravenous dosage form.

7. The pharmaceutical composition of claim 6, wherein the oral dosage form is a tablet or capsule.

8. A method of treating or managing cancer comprising administering to a subject a therapeutically effective amount of a compound of claim 1, wherein the cancer is Non-Hodgkin's lymphoma, Hodgkin's lymphoma, diffuse large B-cell lymphoma, Burkitt's lymphoma, or cutaneous T-cell lymphoma.

9. The method of claim 8, which further comprises administration of one or more additional agents.

10. The method of claim 8, wherein the compound is administered orally or parenterally.

11. A method of treating or managing cancer comprising administering to a subject a therapeutically effective amount of a compound of claim 1, wherein the cancer is prostate cancer, pancreatic cancer, breast cancer or colorectal cancer.

12. The method of claim 11, which further comprises administration of one or more additional agents.

13. The method of claim 11, wherein the compound is administered orally or parenterally.

* * * * *